United States Patent
Morey et al.

(10) Patent No.: US 11,780,902 B1
(45) Date of Patent: Oct. 10, 2023

(54) RECEPTOR/HISTIDINE KINASE FUSION CONSTRUCTS AND USES THEREOF

(71) Applicant: COLORADO STATE UNIVERSITY RESEARCH FOUNDATION, Fort Collins, CO (US)

(72) Inventors: Kevin J. Morey, Fort Collins, CO (US); June I. Medford, Fort Collins, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 410 days.

(21) Appl. No.: 16/517,107

(22) Filed: Jul. 19, 2019

Related U.S. Application Data

(60) Provisional application No. 62/701,396, filed on Jul. 20, 2018.

(51) Int. Cl.
| | |
|---|---|
| *C07K 14/705* | (2006.01) |
| *G01N 33/50* | (2006.01) |
| *C12N 9/12* | (2006.01) |
| *C12N 15/62* | (2006.01) |

(52) U.S. Cl.
CPC .............. *C07K 14/705* (2013.01); *C12N 9/12* (2013.01); *C12N 15/62* (2013.01); *G01N 33/5097* (2013.01); *C07K 2319/035* (2013.01)

(58) Field of Classification Search
CPC ......... C07K 14/705; C12N 9/12; C12N 15/62
See application file for complete search history.

(56) References Cited

U.S. PATENT DOCUMENTS

| | | |
|---|---|---|
| 7,153,685 B2 | 12/2006 | Mao et al. |
| 8,148,605 B2 | 4/2012 | Medford et al. |
| 9,062,320 B2 | 6/2015 | Medford et al. |
| 9,766,255 B2 | 9/2017 | Church et al. |
| 2016/0202256 A1 | 7/2016 | Church et al. |
| 2017/0198363 A1 | 7/2017 | Medford et al. |
| 2018/0105825 A1 | 4/2018 | Medford et al. |

FOREIGN PATENT DOCUMENTS

| | | |
|---|---|---|
| WO | 2002024899 | 3/2002 |
| WO | 2014159947 | 10/2014 |

OTHER PUBLICATIONS

Ohlendorf et al., "Library-Aided Probing of Linker Determinants in Hybrid Photoreceptors", ACS Synthetic Biology, 2016, vol. 5, pp. 1117-1126. DOI: 10.1021/acssynbio.6b00028.*
Simm et al., "Critical assessment of coiled-coil predictions based on protein structure data", Nature Scientific Reports, 2021, 11: 12439. 18 pages. doi.org/10.1038/s41598-021-91886-w.*
Adase et al., "The residue composition of the aromatic anchor of the second transmembrane helix determines the signaling properties of the aspartate/maltose chemoreceptor Tar of *Escherichia coli*," Biochemistry 51(9):1925-1932, 2012.
Antunes et al., "Programmable ligand detection system in plants through a synthetic signal transduction pathway,". PLoS One 6: e16292, 2011.
Banaszynski et al., "A rapid, reversible, and tunable method to regulate protein function in living cells using synthetic small molecules," Cell 126:995-1004, 2006.
Barbieri & Stock, "Universally applicable methods for monitoring response regulator aspartate phosphorylation both in vitro and in vivo using Phos-tag-based reagents," Anal Biochem 376: 73-82, 2008.
Baumberger et al., "Whole-genome comparison of leucine-rich repeat extensins in *Arabidopsis* and Rice. a conserved family of cell wall proteins form a vegetative and a reproductive clade," Plant Physiol. 131:1313-1326, 2003.
Baumgartner et al., "Transmembrane signalling by a hybrid protein: communication from the domain of chemoreceptor Trg that recognizes sugar-binding proteins to the kinase/phosphatase domain of osmosensor EnvZ," J. Bacteriol. 176:1157-1163, 1994.
Bick et al., "Computational design of environmental sensors for the potent opioid fentanyl," eLife 6:e28909, 2017.
Boyken et al., "De novo design of tunable, pH-driven conformational changes," Science 364, 658-664, 2019.
Capra & Laub, "Evolution of two-component signal transduction systems," Annu Rev Microbiol 66: 325-347, 2012.
Chatterjee et al., "A cell-cell signaling sensor is required for virulence and insect transmission of Xylella Fastidiosa," Proc. Natl. Acad. Sci. USA 105:2670-2675, 2008.
Chevalier et al., "Massively parallel de novo protein design for targeted therapeutics," Nature 550, 74, 2017.
Chen et al., "Programmable design of orthogonal protein heterodimers," Nature 565, 106-111, 2019.
Cheung & Hendrickson, "Sensor domains of two-component regulatory systems," Curr Opin Microbiol 13: 116-123, 2010.
Day et al., "Unintended specificity of an engineered ligand-binding protein facilitated by unpredicted plasticity of the protein fold," Protein Engineering, Design and Selection 31, 375-387, 2018.
Dou et al., "De novo design of a fluorescence-activating β-barrel," Nature 561, 485-491, 2018.
Dwyer & Hellinga, Periplasmic binding proteins: a versatile superfamily for protein engineering. Curr Opin Struct Biol 14, 495-504, 2004.
Feng et al., "A general strategy to construct small molecule biosensors in eukaryotes," eLife 4:e10606, 2015.
Ferris et al., "Mechanism of regulation of receptor histidine kinases," Structure 20(1):56-66, 2012.
Ganesh et al., "Engineered fumarate sensing *Escherichia coli* based on novel chimeric two-component system," J Biotechnol 168(4):560-566, 2013.
Groisman, "The pleiotropic two-component regulatory system PhoP-PhoQ," J. Bacteriol. 183:1835-1842, 2001.

(Continued)

*Primary Examiner* — Suzanne M Noakes
(74) *Attorney, Agent, or Firm* — Dentons US LLP

(57) ABSTRACT

The present disclosure provides compositions and methods for sensing a target substance of interest in the environment and inducing gene expression in response thereto, useful for detection of biological and chemical agents and environmental pollutants.

11 Claims, 22 Drawing Sheets

Specification includes a Sequence Listing.

(56) References Cited

OTHER PUBLICATIONS

Haldimann et al., "Altered recognition mutants of the response regulator PhoB: a new genetic strategy for studying protein-protein interactions," Proc Natl Acad Sci U S A 93(25):14361-14366, 1996.
International Search Report and Written Opinion for PCT/US16/68930 dated May 19, 2017.
Kortemme et al., "Computational redesign of protein-protein interaction specificity," Nat. Struct. Mol. Biol. 11, 371-379, 2004.
Levskaya et al., "Engineering *Escherichia coli* to see light," Nature 438(7067):441-442, 2005.
Looger et al., "Computational design of receptor and sensor proteins with novel functions," Nature 423:185-190, 2003.
Lu et al., "Accurate computational design of multipass transmembrane proteins," Science 359, 1042-1046, 2018.
Marcos et al., "Principles for designing proteins with cavities formed by curved β sheets," Science 355, 201-206, 2017.
Morey et al, "Developing a Synthetic Signal Transduction System in Plants," Method Enzymol 497:581-602, 2011.
Strauch et al., "Computational design of trimeric influenza-neutralizing proteins targeting the hemagglutinin receptor binding site," Nat. Biotechnol. 35(7):667-671, 2017.
Singh et al., "Computational learning reveals coiled coil-like motifs in histidine kinase linker domains," Proc. Natl. Acad. Sci. USA 95:2738-2743, 1998.
Skerker et al., "Rewiring the specificity of two-component signal transduction systems," Cell 133:1043-1054, 2008.
Utsumi et al, "Activation of bacterial porin gene expression by a chimeric signal transducer in response to aspartate," Science 245(4923):1246-1249, 1989.
Wang et al., "*Arabidopsis ovate* family proteins, a novel transcriptional repressor family, control multiple aspects of plant growth and development," PLoS One 6:e23896, 2011.
Wuichet et al., "Evolution and phyletic distribution of two-component signal transduction systems," Curr Opin Microbiol 13: 219-225, 2010.
Johnson et al., "Degradation signal masking by heterodimerization of MATalpha2 and MATa1 blocks their mutual destruction by the ubiquitin-proteasome pathway," Cell 94:217-227, 1998.
Zetsche et al., "A split-Cas9 architecture for inducible genome editing and transcription modulation," Nat Biotechnol 33:139-142, 2015.
Regulatory protein GAL4, UniProt ID P04386, Available at http://www.uniprot.org/uniprot/P04386, Retrieved Jan. 4, 2017.
Tegument protein VP16, UniProt ID P06492, Available at http://www.uniprot.org/uniprot/P06492, Retrieved Jan. 4, 2017.
Tinberg et al., "Computational design of ligand-binding proteins with high affinity and selectivity," Nature 501:212-216, 2013.

\* cited by examiner

--PRIOR ART--

--PRIOR ART--

```
              4        3        2        1     heptad repeats
           ABCDEFGABCDEFGABCDEFGABCDEFG Coiled coil
TRZ        SRHLQHMAAGVKQLADDRTLLMAGVS D
PHOR       LLMVARDVTQMHQLEGARRNFFANVS E
```

FIG. 4

```
                   abcdefgabcdefgabcdefgabcdefg   coiled coil
Trz                SRHLQHMAAGRQLADDRTLLMAGVSHD
Trg                SRHLQQMQHSGMTVGTVRQGAEEIYRG
PhoR               LMVAHDVTGHQLEGARRNFFANVSH
TrzHAMP+M          SRHLQHMAAGHQLEGARRNFFANVSH    high basal
TrzHAMP+V          SRHLQHMAAGHQLEGARRNFFANVSH    inducible
TrgHAMP+V          SRHLQQMQHSHQLEGARRNFFANVSH    inducible
TrgHAMP+G          SRHLQQMQHSHQLEGARRNFFANVSH    high basal
TrgHAMP+A          SRHLQQMQHSHQLEGARRNFFANVSH    high basal
TrgHAMP+L          SRHLQQMQHSHQLEGARRNFFANVSH    high basal
TrgHAMP+I          SRHLQQMQHSHQLEGARRNFFANVSH    high basal
TrgHAMP+E          SRHLQQMQHSHQLEGARRNFFANVSH    high basal
TrgHAMP+T          SRHLQQMQHSHQLEGARRNFFANVSH    high basal
```

FIG. 8

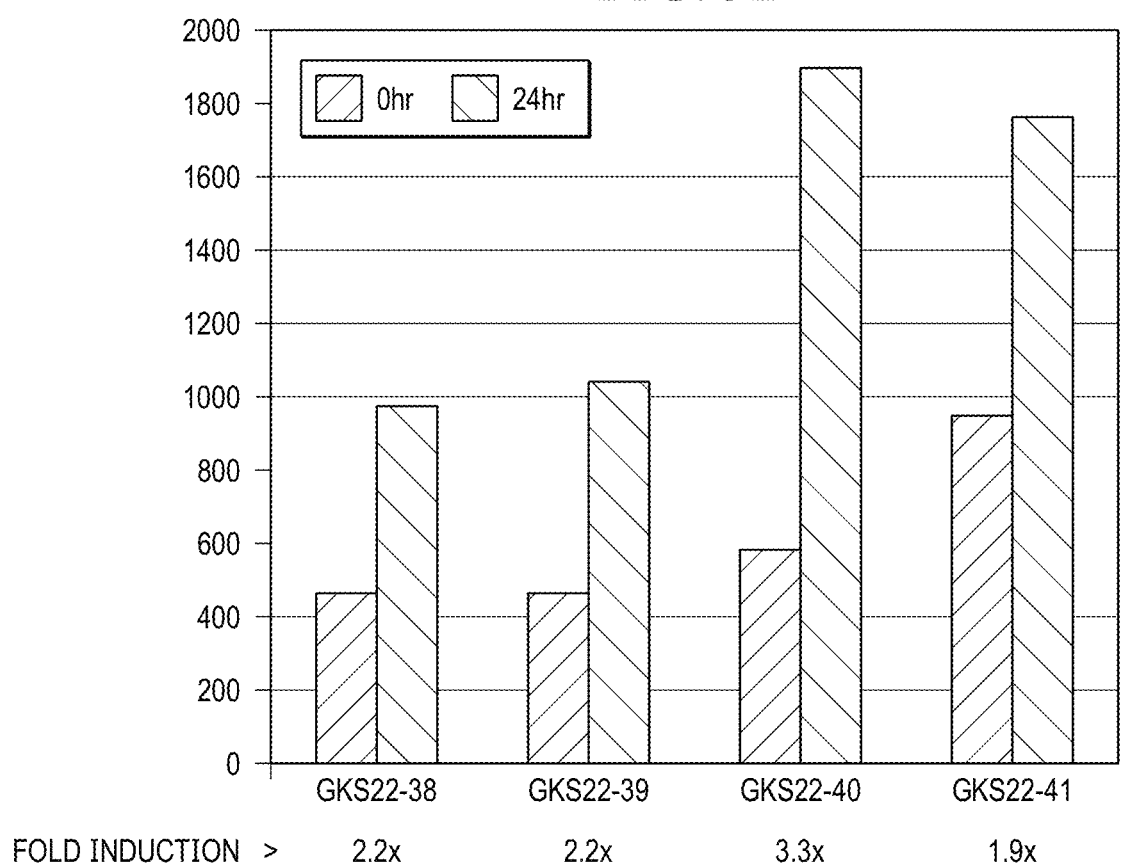

```
      ABCDEFGABCDEFGABCDEFGABCDEFG Coiled Coil
                     275
EnvZ  TRAFNHMAAGVKQLADDRTLLMAGVSHD
PhoR  LLMVARDVTQMHQLEGARRNFFANVSHE
```

FIG. 14

FIG. 17A
FIG. 17B
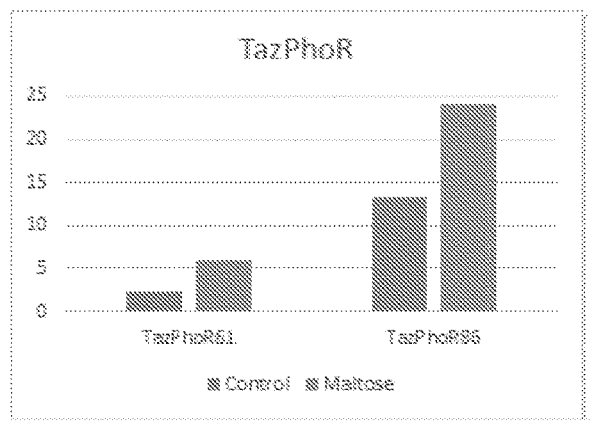
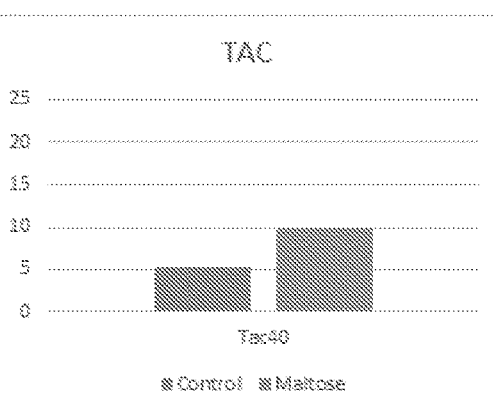

SEQUENCE LISTING

<160> NUMBER OF SEQ ID NOS: 76

<210> SEQ ID NO 1
<211> LENGTH: 1518
<212> TYPE: DNA
<213> ORGANISM: Artificial Sequence
<220> FEATURE:
<223> OTHER INFORMATION: Fusion protein coding sequence

<400> SEQUENCE: 1

```
atgaatacaa ctccctcaca gcgattaggt tttttgcatc acatcaggtt ggttccgtta      60
tttgcctgca ttctaggcgg tatcttagtt ctattcgcat taagttcagc cctggctggc     120
tatttcctct ggcaggccga tcgcgatcag cgtgatgtta ctgcggagat tgagattcgg     180
accgggttag cgaacagttc agatttttg cgttcagccc ggatcaatat gattcaggcc      240
ggggctgcga gtcgtattgc ggaaatggaa gcaatgaagc gaaatattgc gcaagccgaa     300
tcggagatta aacagtcgca gcaaggttat cgtgcttatc agaatcgacc ggtgaaaaca     360
cctgctgatg aagccctcga cactgaatta aatcaacgct ttcaggctta tcacgggt      420 atgcaaccta tgttgaaata tgccaaaaat ggcatgtttg aagcgattat caatcatgaa     480
agtgagcaga tccgaccgct ggataatgct tataccgata ttttgaacaa agccgttaag     540
atacgtagca ccagagccaa ccaactggcg gaactggccc atcagcgcac ccgcctgggt     600
gggatgttca tgattggcgc gtttgtgctt gccctggtca tgacgctgat aacatttatg     660
gtgctacgtc ggatcgtcat tcgtccactg caacatgccg cacaacggat tgaaaaaatc     720
gccagtggcg atctgacgat gaatgatgaa ccggcgggtc gtaatgaaat cggtcgctta     780
agtcgtcatt tacagcatat ggcggctggt gttaagcaac tggaaggggc gcggcgtaac     840
ttttttgcca acgtgagcca tgagttacgt acgccattga ccgtgttaca gggttacctg     900
gagatgatga atgagcagcc gctggaaggc gcggtacgcg aaaaagcgtt gcacaccatg     960
cgcgagcaga cccagcggat ggaaggactg gtgaagcaat gctgacgct gtcgaaaata    1020 gaagccgcac cgacgcattt gctcaatgaa aaggttgatg tgccgatgat gctgcgcgtt    1080
gttgagcgcg aggctcagac tctgagtcag aaaaaacaga catttacctt tgagatagat    1140
aacggcctca aggtgtctgg caacgaagat cagctacgca gtgcgatttc gaacctggtc    1200
tataacgccg tgaatcatac gccggaaggc acgcatatca ccgtacgctg gcagcgagtg    1260
```

```
ccgcacggtg ccgaatttag cgttgaagat aacggaccgg gcattgcacc ggagcatatt     1320
ccgcgcctga ccgagcgttt ttatcgcgtt gataaagcgc gttcccggca aaccggcggt     1380
agcggattag ggttagcgat cgtgaaacat gctgtgaatc atcacgaaag tcgcctgaat     1440
attgagagta cagtaggaaa aggaacacgt ttcagttttg ttatcccgga acgtttaatt     1500
gccaaaaaca gcgattaa                                                  1518

<210> SEQ ID NO 2
<211> LENGTH: 505
<212> TYPE: PRT
<213> ORGANISM: Artificial Sequence
<220> FEATURE:
<223> OTHER INFORMATION: Fusion protein

<400> SEQUENCE: 2
```

Met Asn Thr Thr Pro Ser Gln Arg Leu Gly Phe Leu His His Ile Arg
1               5                   10                  15

Leu Val Pro Leu Phe Ala Cys Ile Leu Gly Gly Ile Leu Val Leu Phe
            20                  25                  30

Ala Leu Ser Ser Ala Leu Ala Gly Tyr Phe Leu Trp Gln Ala Asp Arg
        35                  40                  45

Asp Gln Arg Asp Val Thr Ala Glu Ile Glu Ile Arg Thr Gly Leu Ala
    50                  55                  60

Asn Ser Ser Asp Phe Leu Arg Ser Ala Arg Ile Asn Met Ile Gln Ala
65                  70                  75                  80

Gly Ala Ala Ser Arg Ile Ala Glu Met Glu Ala Met Lys Arg Asn Ile
                85                  90                  95

Ala Gln Ala Glu Ser Glu Ile Lys Gln Ser Gln Gln Gly Tyr Arg Ala
            100                 105                 110

Tyr Gln Asn Arg Pro Val Lys Thr Pro Ala Asp Glu Ala Leu Asp Thr
        115                 120                 125

Glu Leu Asn Gln Arg Phe Gln Ala Tyr Ile Thr Gly Met Gln Pro Met
    130                 135                 140

Leu Lys Tyr Ala Lys Asn Gly Met Phe Glu Ala Ile Ile Asn His Glu
145                 150                 155                 160

Ser Glu Gln Ile Arg Pro Leu Asp Asn Ala Tyr Thr Asp Ile Leu Asn
                165                 170                 175

Lys Ala Val Lys Ile Arg Ser Thr Arg Ala Asn Gln Leu Ala Glu Leu
            180                 185                 190

Ala His Gln Arg Thr Arg Leu Gly Gly Met Phe Met Ile Gly Ala Phe
        195                 200                 205

Val Leu Ala Leu Val Met Thr Leu Ile Thr Phe Met Val Leu Arg Arg
    210                 215                 220

Ile Val Ile Arg Pro Leu Gln His Ala Ala Gln Ile Glu Lys Ile
225                 230                 235                 240

Ala Ser Gly Asp Leu Thr Met Asn Asp Glu Pro Ala Gly Arg Asn Glu
                245                 250                 255

Ile Gly Arg Leu Ser Arg His Leu Gln His Met Ala Ala Gly Val Lys
            260                 265                 270

Gln Leu Glu Gly Ala Arg Arg Asn Phe Phe Ala Asn Val Ser His Glu
        275                 280                 285

Leu Arg Thr Pro Leu Thr Val Leu Gln Gly Tyr Leu Glu Met Met Asn
    290                 295                 300

Glu Gln Pro Leu Glu Gly Ala Val Arg Glu Lys Ala Leu His Thr Met
305                 310                 315                 320

```
Arg Glu Gln Thr Gln Arg Met Glu Gly Leu Val Lys Gln Leu Leu Thr
                325                 330                 335
Leu Ser Lys Ile Glu Ala Ala Pro Thr His Leu Leu Asn Glu Lys Val
            340                 345                 350
Asp Val Pro Met Met Leu Arg Val Val Glu Arg Glu Ala Gln Thr Leu
        355                 360                 365
Ser Gln Lys Lys Gln Thr Phe Thr Phe Glu Ile Asp Asn Gly Leu Lys
    370                 375                 380
Val Ser Gly Asn Glu Asp Gln Leu Arg Ser Ala Ile Ser Asn Leu Val
385                 390                 395                 400
Tyr Asn Ala Val Asn His Thr Pro Glu Gly Thr His Ile Thr Val Arg
                405                 410                 415
Trp Gln Arg Val Pro His Gly Ala Glu Phe Ser Val Glu Asp Asn Gly
            420                 425                 430
Pro Gly Ile Ala Pro Glu His Ile Pro Arg Leu Thr Glu Arg Phe Tyr
        435                 440                 445
Arg Val Asp Lys Ala Arg Ser Arg Gln Thr Gly Gly Ser Gly Leu Gly
    450                 455                 460
Leu Ala Ile Val Lys His Ala Val Asn His His Glu Ser Arg Leu Asn
465                 470                 475                 480
Ile Glu Ser Thr Val Gly Lys Gly Thr Arg Phe Ser Phe Val Ile Pro
                485                 490                 495
Glu Arg Leu Ile Ala Lys Asn Ser Asp
            500                 505

<210> SEQ ID NO 3
<211> LENGTH: 1518
<212> TYPE: DNA
<213> ORGANISM: Artificial Sequence
<220> FEATURE:
<223> OTHER INFORMATION: Fusion protein coding sequence

<400> SEQUENCE: 3
atgaatacaa ctccctcaca gcgattaggt tttttgcatc acatcaggtt ggttccgtta      60
tttgcctgca ttctaggcgg tatcttagtt ctattcgcat taagttcagc cctggctggc     120
tatttcctct ggcaggccga tcgcgatcag cgtgatgtta ctgcggagat tgagattcgg     180
accgggttag cgaacagttc agatttttg cgttcagccc ggatcaatat gattcaggcc     240
ggggctgcga gtcgtattgc ggaaatggaa gcaatgaagc gaaatattgc gcaagccgaa     300
tcggagatta acagtcgca gcaaggttat cgtgcttatc agaatcgacc ggtgaaaaca     360
cctgctgatg aagccctcga cactgaatta atcaacgct ttcaggctta tcacgggt      420
atgcaaccta tgttgaaata tgccaaaaat ggcatgtttg aagcgattat caatcatgaa     480
agtgagcaga tccgaccgct ggataatgct tataccgata ttttgaacaa gccgttaag     540
atacgtagca ccagagccaa ccaactggcg gaactggccc atcagcgcac cgcctgggt     600
gggatgttca tgattggcgc gtttgtgctt gccctggtca tgacgctgat aacatttatg     660
gtgctacgtc ggatcgtcat tcgtccactg caacatgccg cacaacggat tgaaaaaatc     720
gccagtggcg atctgacgat gaatgatgaa ccggcgggtc gtaatgaaat cggtcgctta     780
agtcgtcatt tacagcatat ggcggctggt gttcatcaac tggaagggc gcggcgtaac     840
tttttttgcca acgtgagcca tgagttacgt acgccattga ccgtgttaca gggttacctg     900
gagatgatga atgagcagcc gctggaaggc gcggtacgcg aaaaagcgtt gcacaccatg     960
```

-continued

```
cgcgagcaga cccagcggat ggaaggactg gtgaagcaat tgctgacgct gtcgaaaata    1020
gaagccgcac cgacgcattt gctcaatgaa aaggttgatg tgccgatgat gctgcgcgtt    1080
gttgagcgcg aggctcagac tctgagtcag aaaaaacaga catttacctt tgagatagat    1140
aacggcctca aggtgtctgg caacgaagat cagctacgca gtgcgatttc gaacctggtc    1200
tataacgccg tgaatcatac gccggaaggc acgcatatca ccgtacgctg cagcgagtg     1260 ccgcacggtg ccgaatttag cgttgaagat aacggaccgg gcattgcacc ggagcatatt    1320
ccgcgcctga ccgagcgttt ttatcgcgtt gataaagcgc gttcccggca accggcggt     1380 agcggattag ggttagcgat cgtgaaacat gctgtgaatc atcacgaaag tcgcctgaat    1440
attgagagta cagtaggaaa aggaacacgt ttcagttttg ttatcccgga acgtttaatt    1500
gccaaaaaca gcgattaa                                                   1518
```

<210> SEQ ID NO 4
<211> LENGTH: 505
<212> TYPE: PRT
<213> ORGANISM: Artificial Sequence
<220> FEATURE:
<223> OTHER INFORMATION: Fusion protein

<400> SEQUENCE: 4

```
Met Asn Thr Thr Pro Ser Gln Arg Leu Gly Phe Leu His His Ile Arg
1               5                   10                  15

Leu Val Pro Leu Phe Ala Cys Ile Leu Gly Gly Ile Leu Val Leu Phe
            20                  25                  30

Ala Leu Ser Ser Ala Leu Ala Gly Tyr Phe Leu Trp Gln Ala Asp Arg
        35                  40                  45

Asp Gln Arg Asp Val Thr Ala Glu Ile Glu Ile Arg Thr Gly Leu Ala
    50                  55                  60

Asn Ser Ser Asp Phe Leu Arg Ser Ala Arg Ile Asn Met Ile Gln Ala
65                  70                  75                  80

Gly Ala Ala Ser Arg Ile Ala Glu Met Glu Ala Met Lys Arg Asn Ile
                85                  90                  95

Ala Gln Ala Glu Ser Glu Ile Lys Gln Ser Gln Gln Gly Tyr Arg Ala
            100                 105                 110

Tyr Gln Asn Arg Pro Val Lys Thr Pro Ala Asp Glu Ala Leu Asp Thr
        115                 120                 125

Glu Leu Asn Gln Arg Phe Gln Ala Tyr Ile Thr Gly Met Gln Pro Met
    130                 135                 140

Leu Lys Tyr Ala Lys Asn Gly Met Phe Glu Ala Ile Ile Asn His Glu
145                 150                 155                 160

Ser Glu Gln Ile Arg Pro Leu Asp Asn Ala Tyr Thr Asp Ile Leu Asn
                165                 170                 175

Lys Ala Val Lys Ile Arg Ser Thr Arg Ala Asn Gln Leu Ala Glu Leu
            180                 185                 190

Ala His Gln Arg Thr Arg Leu Gly Gly Met Phe Met Ile Gly Ala Phe
        195                 200                 205

Val Leu Ala Leu Val Met Thr Leu Ile Thr Phe Met Val Leu Arg Arg
    210                 215                 220

Ile Val Ile Arg Pro Leu Gln His Ala Ala Gln Arg Ile Glu Lys Ile
225                 230                 235                 240

Ala Ser Gly Asp Leu Thr Met Asn Asp Glu Pro Ala Gly Arg Asn Glu
                245                 250                 255

Ile Gly Arg Leu Ser Arg His Leu Gln His Met Ala Ala Gly Val His
```

-continued

```
                    260                 265                 270
Gln Leu Glu Gly Ala Arg Arg Asn Phe Phe Ala Asn Val Ser His Glu
            275                 280                 285

Leu Arg Thr Pro Leu Thr Val Leu Gln Gly Tyr Leu Glu Met Met Asn
        290                 295                 300

Glu Gln Pro Leu Glu Gly Ala Val Arg Glu Lys Ala Leu His Thr Met
305                 310                 315                 320

Arg Glu Gln Thr Gln Arg Met Glu Gly Leu Val Lys Gln Leu Leu Thr
                325                 330                 335

Leu Ser Lys Ile Glu Ala Ala Pro Thr His Leu Leu Asn Glu Lys Val
            340                 345                 350

Asp Val Pro Met Met Leu Arg Val Val Glu Arg Glu Ala Gln Thr Leu
        355                 360                 365

Ser Gln Lys Lys Gln Thr Phe Thr Phe Glu Ile Asp Asn Gly Leu Lys
    370                 375                 380

Val Ser Gly Asn Glu Asp Gln Leu Arg Ser Ala Ile Ser Asn Leu Val
385                 390                 395                 400

Tyr Asn Ala Val Asn His Thr Pro Glu Gly Thr His Ile Thr Val Arg
                405                 410                 415

Trp Gln Arg Val Pro His Gly Ala Glu Phe Ser Val Glu Asp Asn Gly
            420                 425                 430

Pro Gly Ile Ala Pro Glu His Ile Pro Arg Leu Thr Gly Arg Phe Tyr
        435                 440                 445

Arg Val Asp Lys Ala Arg Ser Arg Gln Thr Gly Gly Ser Gly Leu Gly
    450                 455                 460

Leu Ala Ile Val Lys His Ala Val Asn His His Glu Ser Arg Leu Asn
465                 470                 475                 480

Ile Glu Ser Thr Val Gly Lys Gly Thr Arg Phe Ser Phe Val Ile Pro
                485                 490                 495

Glu Arg Leu Ile Ala Lys Asn Ser Asp
            500                 505
```

<210> SEQ ID NO 5
<211> LENGTH: 1254
<212> TYPE: DNA
<213> ORGANISM: Artificial Sequence
<220> FEATURE:
<223> OTHER INFORMATION: Fusion protein coding sequence

<400> SEQUENCE: 5

```
atgttaaaaa aggcaaagtg gatttgttct agactttcac aaaggccaga ttctgagcat      60
gttcagaatt tgatcagact cgttattgtg tcacttttta ttatctattt gaatgcttgc     120
tgggatggag aaaccgatct taacacttct aggataattt ggtctgttct tttgagtgat     180
ttgggtgtgt cactcgcttt aatgcttgca attgttatgc atccacaaat cagtcacgtg     240
agaaggtgta ttggaatcat agcagattat accagtttaa ctgttcttat gctcttaatg     300
ggagaggctg ttctcctct  ttacgttttg tgcctctggg tgacaatcgg aaatggtttg     360
agatatggat cagtttacct tttggtgact acaaccttgg gtgctctttc ttttcttact     420
gttattcttg tgtctgctta ttggaagtca atccattcc tcgcatgggg actcttaatc     480
ggtttaattg ctatcccttg gtacttccaa tcacttttga aggctctcat acaagcatta     540
aacgatgtta aacagcttga gggagctaga aggaatttct ttgcaaacgt ttctcacgaa     600
ttgagaacac acttaccgt gttgcaagga tacttggaaa tgatgaatga gcagcctctc     660
```

```
gaaggtgctg ttagggagaa agcacttcat acaatgagag agcaaaccca gaggatggaa    720
ggtctcgtga agcagctctt aactttatct aaaattgagg ctgcaccaac acaccttttg    780
aacgaaaagg ttgatgtgcc tatgatgctt agagttgtgg aaagggaggc acaaacattg    840
tcacaaaaga aacagacttt tacattcgag atcgataatg gtttgaaagt ttctggtaac    900
gaagatcagc ttagaagtgc tatctctaat ttggtttaca acgcagtgaa ccatactcca    960
gaaggaactc acataacagt tagatggcaa agggtgcctc atggtgcaga gttttctgtt   1020
gaagataacg gacctggtat cgctccagag cacatacctg acttaccga aagattctac    1080 agggttgata aggctagaag taggcagact ggaggttctg gattaggtct tgctatagtt   1140
aaacatgcag tgaatcatca cgagtcaaga ttgaacattg aaagtacagt tggtaagggt   1200
accaggttca gtttcgtgat accagagagg ttgatagcaa agaatagtga ttga          1254
```

```
<210> SEQ ID NO 6
<211> LENGTH: 417
<212> TYPE: PRT
<213> ORGANISM: Artificial Sequence
<220> FEATURE:
<223> OTHER INFORMATION: Fusion protein

<400> SEQUENCE: 6
```

```
Met Leu Lys Lys Ala Lys Trp Ile Cys Ser Arg Leu Ser Gln Arg Pro
1               5                   10                  15

Asp Ser Glu His Val Gln Asn Leu Ile Arg Leu Val Ile Val Ser Leu
            20                  25                  30

Phe Ile Ile Tyr Leu Asn Ala Cys Trp Asp Gly Glu Thr Asp Leu Asn
        35                  40                  45

Thr Ser Arg Ile Ile Trp Ser Val Leu Leu Ser Asp Leu Gly Val Ser
    50                  55                  60

Leu Ala Leu Met Leu Ala Ile Val Met His Pro Gln Ile Ser His Val
65                  70                  75                  80

Arg Arg Cys Ile Gly Ile Ile Ala Asp Tyr Thr Ser Leu Thr Val Leu
                85                  90                  95

Met Leu Leu Met Gly Glu Ala Gly Ser Pro Leu Tyr Val Leu Cys Leu
            100                 105                 110

Trp Val Thr Ile Gly Asn Gly Leu Arg Tyr Gly Ser Val Tyr Leu Leu
        115                 120                 125

Val Thr Thr Leu Gly Ala Leu Ser Phe Leu Thr Val Ile Leu Val
    130                 135                 140

Ser Ala Tyr Trp Lys Ser Asn Pro Phe Leu Ala Trp Gly Leu Leu Ile
145                 150                 155                 160

Gly Leu Ile Ala Ile Pro Trp Tyr Phe Gln Ser Leu Leu Lys Ala Leu
                165                 170                 175

Ile Gln Ala Leu Asn Asp Val Lys Gln Leu Glu Gly Ala Arg Arg Asn
            180                 185                 190

Phe Phe Ala Asn Val Ser His Glu Leu Arg Thr Pro Leu Thr Val Leu
        195                 200                 205

Gln Gly Tyr Leu Glu Met Met Asn Glu Gln Pro Leu Glu Gly Ala Val
    210                 215                 220

Arg Glu Lys Ala Leu His Thr Met Arg Glu Gln Thr Gln Arg Met Glu
225                 230                 235                 240

Gly Leu Val Lys Gln Leu Leu Thr Leu Ser Lys Ile Glu Ala Ala Pro
                245                 250                 255

Thr His Leu Leu Asn Glu Lys Val Asp Val Pro Met Met Leu Arg Val
```

260                 265                 270
Val Glu Arg Glu Ala Gln Thr Leu Ser Gln Lys Lys Gln Thr Phe Thr
                275                 280                 285

Phe Glu Ile Asp Asn Gly Leu Lys Val Ser Gly Asn Glu Asp Gln Leu
            290                 295                 300

Arg Ser Ala Ile Ser Asn Leu Val Tyr Asn Ala Val Asn His Thr Pro
305                 310                 315                 320

Glu Gly Thr His Ile Thr Val Arg Trp Gln Arg Val Pro His Gly Ala
                325                 330                 335

Glu Phe Ser Val Glu Asp Asn Gly Pro Gly Ile Ala Pro Glu His Ile
            340                 345                 350

Pro Arg Leu Thr Glu Arg Phe Tyr Arg Val Asp Lys Ala Arg Ser Arg
355                 360                 365

Gln Thr Gly Gly Ser Gly Leu Gly Leu Ala Ile Val Lys His Ala Val
            370                 375                 380

Asn His His Glu Ser Arg Leu Asn Ile Glu Ser Thr Val Gly Lys Gly
385                 390                 395                 400

Thr Arg Phe Ser Phe Val Ile Pro Glu Arg Leu Ile Ala Lys Asn Ser
                405                 410                 415

Asp

<210> SEQ ID NO 7
<211> LENGTH: 1503
<212> TYPE: DNA
<213> ORGANISM: Artificial Sequence
<220> FEATURE:
<223> OTHER INFORMATION: Fusion protein coding sequence

<400> SEQUENCE: 7
atgaatacaa ctccctcaca gcgattaggt tttttgcatc acatcaggtt ggttccgtta      60
tttgcctgca ttctaggcgg tatcttagtt ctattcgcat taagttcagc cctggctggc     120
tatttcctct ggcaggccga tcgcgatcag cgtgatgtta ctgcggagat tgagattcgg     180
accgggttag cgaacagttc agatttttg cgttcagccc ggatcaatat gattcaggcc      240
ggggctgcga gtcgtattgc ggaaatggaa gcaatgaagc gaaatattgc gcaagccgaa     300
tcggagatta aacagtcgca gcaaggttat cgtgcttatc agaatcgacc ggtgaaaaca     360
cctgctgatg aagcccctcg acactgaatta aatcaacgct tcaggcctta tcacgggt     420 atgcaaccta tgttgaaata tgccaaaaat ggcatgtttg aagcgattat caatcatgaa     480
agtgagcaga tccgaccgct ggataatgct tataccgata ttttgaacaa agccgttaag     540
atacgtagca ccagagccaa ccaactggcg gaactggccc atcagcgcac ccgcctgggt     600
gggatgttca tgattggcgc gtttgtgctt gccctggtca tgacgctgat aacatttatg     660
gtgctacgtc ggatcgtcat tcgtccactg caacatgccg cacaacggat tgaaaaaatc     720
gccagtggcg atctgacgat gaatgatgaa ccggcgggtc gtaatgaaat cggtcgctta     780
agtcgtcatt tacagcatat ggcggctggt gttaagcaac tggcggatga ccgcacgctg     840
ctgatggcgg gggtaagtca cgacttgcgc acgccgctga cggtgttaca gggttacctg     900
gagatgatga tgagcagcc gctggaaggc gcggtacgcg aaaaagcgtt gcacaccatg     960
cgcgagcaga cccagcggat gaacgccatc attgagcagt ttatcgacta cctgcgcacc     1020
gggcaggaga tgccgatgga aatggcggat cttaatgcag tactcggtga ggtgattgct     1080
gccgaaagtg gctatgagcg ggaaattgaa accgcgcttt accccggcag cattgaagtg     1140

```
aaaatgcacc cgctgtcgat caaacgcgcg gtggcgaata tggtggtcaa cgccgcccgt   1200
tatggcaatg ctggatcaa agtcagcagc ggaacggagc cgaatcgcgc ctggttccag    1260
gtggaagatg acggtccggg aattgcgccg gaacaacgta agcacctgtt ccagccgttt   1320
gtccgcggcg acagtgcgcg caccattagc ggcacgggat tagggctggc aattgtgcag   1380
cgtatcgtgg ataaccataa cgggatgctg agcttggca ccagcgagcg gggcgggctt    1440
tccattcgcg cctggctgcc agtgccggta acgcgggcgc agggcacgac aaaagaaggg   1500
taa                                                                1503
```

<210> SEQ ID NO 8
<211> LENGTH: 500
<212> TYPE: PRT
<213> ORGANISM: Artificial Sequence
<220> FEATURE:
<223> OTHER INFORMATION: Fusion protein

<400> SEQUENCE: 8

```
Met Asn Thr Thr Pro Ser Gln Arg Leu Gly Phe Leu His His Ile Arg
1               5                   10                  15

Leu Val Pro Leu Phe Ala Cys Ile Leu Gly Gly Ile Leu Val Leu Phe
            20                  25                  30

Ala Leu Ser Ser Ala Leu Ala Gly Tyr Phe Leu Trp Gln Ala Asp Arg
        35                  40                  45

Asp Gln Arg Asp Val Thr Ala Glu Ile Glu Ile Arg Thr Gly Leu Ala
    50                  55                  60

Asn Ser Ser Asp Phe Leu Arg Ser Ala Arg Ile Asn Met Ile Gln Ala
65                  70                  75                  80

Gly Ala Ala Ser Arg Ile Ala Glu Met Glu Ala Met Lys Arg Asn Ile
                85                  90                  95

Ala Gln Ala Glu Ser Glu Ile Lys Gln Ser Gln Gln Gly Tyr Arg Ala
            100                 105                 110

Tyr Gln Asn Arg Pro Val Lys Thr Pro Ala Asp Glu Ala Leu Asp Thr
        115                 120                 125

Glu Leu Asn Gln Arg Phe Gln Ala Tyr Ile Thr Gly Met Gln Pro Met
    130                 135                 140

Leu Lys Tyr Ala Lys Asn Gly Met Phe Glu Ala Ile Ile Asn His Glu
145                 150                 155                 160

Ser Glu Gln Ile Arg Pro Leu Asp Asn Ala Tyr Thr Asp Ile Leu Asn
                165                 170                 175

Lys Ala Val Lys Ile Arg Ser Thr Arg Ala Asn Gln Leu Ala Glu Leu
            180                 185                 190

Ala His Gln Arg Thr Arg Leu Gly Gly Met Phe Met Ile Gly Ala Phe
        195                 200                 205

Val Leu Ala Leu Val Met Thr Leu Ile Thr Phe Met Val Leu Arg Arg
    210                 215                 220

Ile Val Ile Arg Pro Leu Gln His Ala Ala Gln Arg Ile Glu Lys Ile
225                 230                 235                 240

Ala Ser Gly Asp Leu Thr Met Asn Asp Glu Pro Ala Gly Arg Asn Glu
                245                 250                 255

Ile Gly Arg Leu Ser Arg His Leu Gln His Met Ala Ala Gly Val Lys
            260                 265                 270

Gln Leu Ala Asp Asp Arg Thr Leu Leu Met Ala Gly Val Ser His Asp
        275                 280                 285

Leu Arg Thr Pro Leu Thr Val Leu Gln Gly Tyr Leu Glu Met Met Asn
```

```
            290                 295                 300
Glu Gln Pro Leu Glu Gly Ala Val Arg Glu Lys Ala Leu His Thr Met
305                 310                 315                 320

Arg Glu Gln Thr Gln Arg Met Asn Ala Ile Ile Glu Gln Phe Ile Asp
                325                 330                 335

Tyr Leu Arg Thr Gly Gln Glu Met Pro Met Glu Met Ala Asp Leu Asn
            340                 345                 350

Ala Val Leu Gly Glu Val Ile Ala Ala Glu Ser Gly Tyr Glu Arg Glu
        355                 360                 365

Ile Glu Thr Ala Leu Tyr Pro Gly Ser Ile Glu Val Lys Met His Pro
    370                 375                 380

Leu Ser Ile Lys Arg Ala Val Ala Asn Met Val Val Asn Ala Ala Arg
385                 390                 395                 400

Tyr Gly Asn Gly Trp Ile Lys Val Ser Ser Gly Thr Glu Pro Asn Arg
                405                 410                 415

Ala Trp Phe Gln Val Glu Asp Asp Gly Pro Gly Ile Ala Pro Glu Gln
            420                 425                 430

Arg Lys His Leu Phe Gln Pro Phe Val Arg Gly Asp Ser Ala Arg Thr
        435                 440                 445

Ile Ser Gly Thr Gly Leu Gly Leu Ala Ile Val Gln Arg Ile Val Asp
    450                 455                 460

Asn His Asn Gly Met Leu Glu Leu Gly Thr Ser Glu Arg Gly Gly Leu
465                 470                 475                 480

Ser Ile Arg Ala Trp Leu Pro Val Pro Val Thr Arg Ala Gln Gly Thr
                485                 490                 495

Thr Lys Glu Gly
            500

<210> SEQ ID NO 9
<211> LENGTH: 1494
<212> TYPE: DNA
<213> ORGANISM: Artificial Sequence
<220> FEATURE:
<223> OTHER INFORMATION: Fusion protein coding sequence

<400> SEQUENCE: 9
atgaatacaa ctccctcaca gcgattaggt tttttgcatc acatcaggtt ggttccgtta      60
tttgcctgca ttctaggcgg tatcttagtt ctattcgcat taagttcagc cctggctggc     120
tatttcctct ggcaggccga tcgcgatcag cgtgatgtta ctgcggagat tgagattcgg     180
accgggttag cgaacagttc agatttttg cgttcagccc ggatcaatat gattcaggcc     240
ggggctgcga gtcgtattgc ggaaatggaa gcaatgaagc gaaatattgc gcaagccgaa     300
tcggagatta acagtcgca gcaaggttat cgtgcttatc agaatcgacc ggtgaaaaca     360
cctgctgatg aagccctcga cactgaatta aatcaacgct ttcaggctta tcacgggt     420 atgcaaccta tgttgaaata tgccaaaaat ggcatgtttg aagcgattat caatcatgaa     480
agtgagcaga tccgaccgct ggataatgct tataccgata ttttgaacaa agccgttaag     540
atacgtagca ccagagccaa ccaactggcg gaactggccc atcagcgcac ccgcctgggt     600
gggatgttca tgattggcgc gtttgtgctt gccctggtca tgacgctgat aacatttatg     660
gtgctacgtc ggatcgtcat tcgtccactg caacatgccg cacaacggat tgaaaaaatc     720
gccagtggcg atctgacgat gaatgatgaa ccggcgggtc gtaatgaaat cggtcgctta     780
agtcgtcatt tacagcatat ggcggctggt gttaagcaac tggaaggggc gctgatggcg     840
```

```
ggggtaagtc acgacttgcg cacgccgctg acggtgttac agggttacct ggagatgatg    900
aatgagcagc cgctggaagg cgcggtacgc gaaaaagcgt tgcacaccat gcgcgagcag    960
acccagcgga tgaacgccat cattgagcag tttatcgact acctgcgcac cgggcaggag   1020
atgccgatgg aaatggcgga tcttaatgca gtactcggtg aggtgattgc tgccgaaagt   1080
ggctatgagc gggaaattga aaccgcgctt tacccggca gcattgaagt gaaaatgcac    1140
ccgctgtcga tcaaacgcgc ggtggcgaat atggtggtca acgccgcccg ttatggcaat   1200
ggctggatca aagtcagcag cggaacggag ccgaatcgcg cctggttcca ggtggaagat   1260
gacggtccgg gaattgcgcc ggaacaacgt aagcacctgt tccagccgtt tgtccgcggc   1320
gacagtgcgc gcaccattag cggcacggga ttagggctgg caattgtgca gcgtatcgtg   1380
gataaccata acgggatgct ggagcttggc accagcgagc ggggcgggct ttccattcgc   1440
gcctggctgc cagtgccggt aacgcgggcg cagggcacga caaagaagg gtaa          1494
```

<210> SEQ ID NO 10
<211> LENGTH: 497
<212> TYPE: PRT
<213> ORGANISM: Artificial Sequence
<220> FEATURE:
<223> OTHER INFORMATION: Fusion protein

<400> SEQUENCE: 10

```
Met Asn Thr Thr Pro Ser Gln Arg Leu Gly Phe Leu His His Ile Arg
1               5                   10                  15

Leu Val Pro Leu Phe Ala Cys Ile Leu Gly Gly Ile Leu Val Leu Phe
            20                  25                  30

Ala Leu Ser Ser Ala Leu Ala Gly Tyr Phe Leu Trp Gln Ala Asp Arg
        35                  40                  45

Asp Gln Arg Asp Val Thr Ala Glu Ile Glu Ile Arg Thr Gly Leu Ala
    50                  55                  60

Asn Ser Ser Asp Phe Leu Arg Ser Ala Arg Ile Asn Met Ile Gln Ala
65                  70                  75                  80

Gly Ala Ala Ser Arg Ile Ala Glu Met Glu Ala Met Lys Arg Asn Ile
                85                  90                  95

Ala Gln Ala Glu Ser Glu Ile Lys Gln Ser Gln Gln Gly Tyr Arg Ala
            100                 105                 110

Tyr Gln Asn Arg Pro Val Lys Thr Pro Ala Asp Glu Ala Leu Asp Thr
        115                 120                 125

Glu Leu Asn Gln Arg Phe Gln Ala Tyr Ile Thr Gly Met Gln Pro Met
    130                 135                 140

Leu Lys Tyr Ala Lys Asn Gly Met Phe Glu Ala Ile Ile Asn His Glu
145                 150                 155                 160

Ser Glu Gln Ile Arg Pro Leu Asp Asn Ala Tyr Thr Asp Ile Leu Asn
                165                 170                 175

Lys Ala Val Lys Ile Arg Ser Thr Arg Ala Asn Gln Leu Ala Glu Leu
            180                 185                 190

Ala His Gln Arg Thr Arg Leu Gly Gly Met Phe Met Ile Gly Ala Phe
        195                 200                 205

Val Leu Ala Leu Val Met Thr Leu Ile Thr Phe Met Val Leu Arg Arg
    210                 215                 220

Ile Val Ile Arg Pro Leu Gln His Ala Ala Gln Arg Ile Glu Lys Ile
225                 230                 235                 240

Ala Ser Gly Asp Leu Thr Met Asn Asp Glu Pro Ala Gly Arg Asn Glu
                245                 250                 255
```

```
Ile Gly Arg Leu Ser Arg His Leu Gln His Met Ala Ala Gly Val Lys
            260                 265                 270
Gln Leu Glu Gly Ala Leu Met Ala Gly Val Ser His Asp Leu Arg Thr
        275                 280                 285
Pro Leu Thr Val Leu Gln Gly Tyr Leu Glu Met Met Asn Glu Gln Pro
    290                 295                 300
Leu Glu Gly Ala Val Arg Glu Lys Ala Leu His Thr Met Arg Glu Gln
305                 310                 315                 320
Thr Gln Arg Met Asn Ala Ile Ile Glu Gln Phe Ile Asp Tyr Leu Arg
                325                 330                 335
Thr Gly Gln Glu Met Pro Met Glu Met Ala Asp Leu Asn Ala Val Leu
            340                 345                 350
Gly Glu Val Ile Ala Ala Glu Ser Gly Tyr Glu Arg Glu Ile Glu Thr
        355                 360                 365
Ala Leu Tyr Pro Gly Ser Ile Glu Val Lys Met His Pro Leu Ser Ile
    370                 375                 380
Lys Arg Ala Val Ala Asn Met Val Val Asn Ala Ala Arg Tyr Gly Asn
385                 390                 395                 400
Gly Trp Ile Lys Val Ser Ser Gly Thr Glu Pro Asn Arg Ala Trp Phe
                405                 410                 415
Gln Val Glu Asp Asp Gly Pro Gly Ile Ala Pro Glu Gln Arg Lys His
            420                 425                 430
Leu Phe Gln Pro Phe Val Arg Gly Asp Ser Ala Arg Thr Ile Ser Gly
        435                 440                 445
Thr Gly Leu Gly Leu Ala Ile Val Gln Arg Ile Val Asp Asn His Asn
    450                 455                 460
Gly Met Leu Glu Leu Gly Thr Ser Glu Arg Gly Gly Leu Ser Ile Arg
465                 470                 475                 480
Ala Trp Leu Pro Val Pro Val Thr Arg Ala Gln Gly Thr Thr Lys Glu
                485                 490                 495
Gly

<210> SEQ ID NO 11
<211> LENGTH: 1503
<212> TYPE: DNA
<213> ORGANISM: Artificial Sequence
<220> FEATURE:
<223> OTHER INFORMATION: Fusion protein coding sequence

<400> SEQUENCE: 11 atgaataacaa ctccctcaca gcgattaggt tttttgcatc acatcaggtt ggttccgtta      60
tttgcctgca ttctaggcgg tatcttagtt ctattcgcat taagttcagc cctggctggc     120
tatttcctct ggcaggccga tcgcgatcag cgtgatgtta ctgcggagat tgagattcgg     180
accgggttag cgaacagttc agattttttg cgttcagccc ggatcaatat gattcaggcc     240
ggggctgcga gtcgtattgc ggaaatggaa gcaatgaagc gaaatattgc gcaagccgaa     300
tcggagatta acagtcgca gcaaggttat cgtgcttatc agaatcgacc ggtgaaaaca     360
cctgctgatg aagccctcga cactgaatta aatcaacgct tcaggctta tcacgggt       420 atgcaaccta tgttgaaata tgccaaaaat ggcatgtttg aagcgattat caatcatgaa     480
agtgagcaga tccgaccgct ggataatgct tataccgata ttttgaacaa agccgttaag     540
atacgtagca ccagagccaa ccaactggcg gaactggccc atcagcgcac cgcctgggt     600 gggatgttca tgattggcgc gtttgtgctt gccctggtca tgacgctgat aacatttatg     660
```

```
gtgctacgtc ggatcgtcat tcgtccactg caacatgccg cacaacggat tgaaaaaatc    720
gccagtggcg atctgacgat gaatgatgaa ccggcgggtc gtaatgaaat cggtcgctta    780
agtcgtcatt tacagcatat ggcggctggt gttaagcaac tgcgaggggt gcgcacgctg    840
ctgatggcgg gggtaagtca cgacttgcgc acgccgctga cggtgttaca gggttacctg    900
gagatgatga atgagcagcc gctggaaggc gcggtacgcg aaaaagcgtt gcacaccatg    960
cgcgagcaga cccagcggat gaacgccatc attgagcagt ttatcgacta cctgcgcacc    1020
gggcaggaga tgccgatgga aatggcggat cttaatgcag tactcggtga ggtgattgct    1080
gccgaaagtg gctatgagcg ggaaattgaa accgcgcttt accccggcag cattgaagtg    1140
aaaatgcacc cgctgtcgat caaacgcgcg gtggcgaata tggtggtcaa cgccgcccgt    1200
tatggcaatg gctggatcaa agtcagcagc ggaacggagc cgaatcgcgc ctggttccag    1260
gtggaagatg acgtccggg  aattgcgccg gaacaacgta agcacctgtt ccagccgttt    1320
gtccgcggcg acagtgcgcg caccattagc ggcacgggat tagggctggc aattgtgcag    1380
cgtatcgtgg ataaccataa cgggatgctg gagcttggca ccagcgagcg ggcgggctt    1440 tccattcgcg cctggctgcc agtgccggta acgcgggcgc agggcacgac aaaagaaggg    1500
taa                                                                  1503
```

<210> SEQ ID NO 12
<211> LENGTH: 500
<212> TYPE: PRT
<213> ORGANISM: Artificial Sequence
<220> FEATURE:
<223> OTHER INFORMATION: Fusion protein

<400> SEQUENCE: 12

```
Met Asn Thr Thr Pro Ser Gln Arg Leu Gly Phe Leu His His Ile Arg
1               5                   10                  15

Leu Val Pro Leu Phe Ala Cys Ile Leu Gly Gly Ile Leu Val Leu Phe
            20                  25                  30

Ala Leu Ser Ser Ala Leu Ala Gly Tyr Phe Leu Trp Gln Ala Asp Arg
        35                  40                  45

Asp Gln Arg Asp Val Thr Ala Glu Ile Glu Ile Arg Thr Gly Leu Ala
    50                  55                  60

Asn Ser Ser Asp Phe Leu Arg Ser Ala Arg Ile Asn Met Ile Gln Ala
65                  70                  75                  80

Gly Ala Ala Ser Arg Ile Ala Glu Met Glu Ala Met Lys Arg Asn Ile
                85                  90                  95

Ala Gln Ala Glu Ser Glu Ile Lys Gln Ser Gln Gln Gly Tyr Arg Ala
            100                 105                 110

Tyr Gln Asn Arg Pro Val Lys Thr Pro Ala Asp Glu Ala Leu Asp Thr
        115                 120                 125

Glu Leu Asn Gln Arg Phe Gln Ala Tyr Ile Thr Gly Met Gln Pro Met
    130                 135                 140

Leu Lys Tyr Ala Lys Asn Gly Met Phe Glu Ala Ile Ile Asn His Glu
145                 150                 155                 160

Ser Glu Gln Ile Arg Pro Leu Asp Asn Ala Tyr Thr Asp Ile Leu Asn
                165                 170                 175

Lys Ala Val Lys Ile Arg Ser Thr Arg Ala Asn Gln Leu Ala Glu Leu
            180                 185                 190

Ala His Gln Arg Thr Arg Leu Gly Gly Met Phe Met Ile Gly Ala Phe
        195                 200                 205
```

| | | | | | | | | | | | |
|---|---|---|---|---|---|---|---|---|---|---|---|
|Val|Leu|Ala|Leu|Val|Met|Thr|Leu|Ile|Thr|Phe|Met|Val|Leu|Arg|Arg|
| |210| | | |215| | | |220| | |

Val Leu Ala Leu Val Met Thr Leu Ile Thr Phe Met Val Leu Arg Arg
         210                 215                 220

Ile Val Ile Arg Pro Leu Gln His Ala Ala Gln Arg Ile Glu Lys Ile
225                 230                 235                 240

Ala Ser Gly Asp Leu Thr Met Asn Asp Glu Pro Ala Gly Arg Asn Glu
                245                 250                 255

Ile Gly Arg Leu Ser Arg His Leu Gln His Met Ala Ala Gly Val Lys
                260                 265                 270

Gln Leu Arg Gly Val Arg Thr Leu Leu Met Ala Gly Val Ser His Asp
                275                 280                 285

Leu Arg Thr Pro Leu Thr Val Leu Gln Gly Tyr Leu Glu Met Met Asn
        290                 295                 300

Glu Gln Pro Leu Glu Gly Ala Val Arg Glu Lys Ala Leu His Thr Met
305                 310                 315                 320

Arg Glu Gln Thr Gln Arg Met Asn Ala Ile Ile Glu Gln Phe Ile Asp
                325                 330                 335

Tyr Leu Arg Thr Gly Gln Glu Met Pro Met Glu Met Ala Asp Leu Asn
                340                 345                 350

Ala Val Leu Gly Glu Val Ile Ala Ala Glu Ser Gly Tyr Glu Arg Glu
                355                 360                 365

Ile Glu Thr Ala Leu Tyr Pro Gly Ser Ile Glu Val Lys Met His Pro
        370                 375                 380

Leu Ser Ile Lys Arg Ala Val Ala Asn Met Val Val Asn Ala Ala Arg
385                 390                 395                 400

Tyr Gly Asn Gly Trp Ile Lys Val Ser Ser Gly Thr Glu Pro Asn Arg
                405                 410                 415

Ala Trp Phe Gln Val Glu Asp Asp Gly Pro Gly Ile Ala Pro Glu Gln
                420                 425                 430

Arg Lys His Leu Phe Gln Pro Phe Val Arg Gly Asp Ser Ala Arg Thr
                435                 440                 445

Ile Ser Gly Thr Gly Leu Gly Leu Ala Ile Val Gln Arg Ile Val Asp
        450                 455                 460

Asn His Asn Gly Met Leu Glu Leu Gly Thr Ser Glu Arg Gly Gly Leu
465                 470                 475                 480

Ser Ile Arg Ala Trp Leu Pro Val Pro Val Thr Arg Ala Gln Gly Thr
                485                 490                 495

Thr Lys Glu Gly
        500

<210> SEQ ID NO 13
<211> LENGTH: 1503
<212> TYPE: DNA
<213> ORGANISM: Artificial Sequence
<220> FEATURE:
<223> OTHER INFORMATION: Fusion protein coding sequence

<400> SEQUENCE: 13
atgaatacaa ctccctcaca gcgattaggt tttttgcatc acatcaggtt ggttccgtta      60
tttgcctgca ttctaggcgg tatcttagtt ctattcgcat taagttcagc cctggctggc    120
tatttcctct ggcaggccga tcgcgatcag cgtgatgtta ctgcggagat tgagattcgg    180
accgggttag cgaacagttc agatttttg cgttcagccc ggatcaatat gattcaggcc    240
ggggctgcga gtcgtattgc ggaaatggaa gcatgaagc gaaatattgc gcaagccgaa    300
tcggagatta acagtcgca gcaaggttat cgtgcttatc agaatcgacc ggtgaaaaca    360

```
cctgctgatg aagccctcga cactgaatta aatcaacgct ttcaggctta tatcacgggt    420
atgcaaccta tgttgaaata tgccaaaaat ggcatgtttg aagcgattat caatcatgaa    480
agtgagcaga tccgaccgct ggataatgct tataccgata ttttgaacaa agccgttaag    540
atacgtagca ccagagccaa ccaactggcg gaactggccc atcagcgcac ccgcctgggt    600
gggatgttca tgattggcgc gtttgtgctt gccctggtca tgacgctgat aacatttatg    660
gtgctacgtc ggatcgtcat tcgtccactg caacatgccg cacaacggat tgaaaaaatc    720
gccagtggcg atctgacgat gaatgatgaa ccggcgggtc gtaatgaaat cggtcgctta    780
agtcgtcatt tacagcatat ggcggctggt gttaagcaac tggcggggggg gcgcacgctg    840
ctgatggcgg gggtaagtca cgacttgcgc acgccgctga cggtgttaca gggttacctg    900
gagatgatga atgagcagcc gctggaaggc gcggtacgcg aaaaagcgtt gcacaccatg    960
cgcgagcaga cccagcggat gaacgccatc attgagcagt ttatcgacta cctgcgcacc   1020
gggcaggaga tgccgatgga atggcggat cttaatgcag tactcggtga ggtgattgct   1080
gccgaaagtg gctatgagcg ggaaattgaa accgcgcttt accccggcag cattgaagtg   1140
aaaatgcacc cgctgtcgat caaacgcgcg gtggcgaata tggtggtcaa cgccgcccgt   1200
tatggcaatg gctggatcaa agtcagcagc ggaacggagc cgaatcgcgc ctggttccag   1260
gtggaagatg acggtccggg aattgcgccg gaacaacgta agcacctgtt ccagccgttt   1320
gtccgcggcg acagtgcgcg caccattagc ggcacgggat tagggctggc aattgtgcag   1380
cgtatcgtgg ataaccataa cgggatgctg agcttggca ccagcgagcg gggcgggctt   1440
tccattcgcg cctggctgcc agtgccggta acgcgggcgc agggcacgac aaaagaaggg   1500
taa                                                                 1503

<210> SEQ ID NO 14
<211> LENGTH: 500
<212> TYPE: PRT
<213> ORGANISM: Artificial Sequence
<220> FEATURE:
<223> OTHER INFORMATION: Fusion protein

<400> SEQUENCE: 14

Met Asn Thr Thr Pro Ser Gln Arg Leu Gly Phe Leu His His Ile Arg
1               5                   10                  15

Leu Val Pro Leu Phe Ala Cys Ile Leu Gly Gly Ile Leu Val Leu Phe
            20                  25                  30

Ala Leu Ser Ser Leu Ala Gly Tyr Phe Leu Trp Gln Ala Asp Arg
        35                  40                  45

Asp Gln Arg Asp Val Thr Ala Glu Ile Glu Ile Arg Thr Gly Leu Ala
    50                  55                  60

Asn Ser Ser Asp Phe Leu Arg Ser Ala Arg Ile Asn Met Ile Gln Ala
65                  70                  75                  80

Gly Ala Ala Ser Arg Ile Ala Glu Met Glu Ala Met Lys Arg Asn Ile
                85                  90                  95

Ala Gln Ala Glu Ser Glu Ile Lys Gln Ser Gln Gln Gly Tyr Arg Ala
            100                 105                 110

Tyr Gln Asn Arg Pro Val Lys Thr Pro Ala Asp Glu Ala Leu Asp Thr
        115                 120                 125

Glu Leu Asn Gln Arg Phe Gln Ala Tyr Ile Thr Gly Met Gln Pro Met
    130                 135                 140

Leu Lys Tyr Ala Lys Asn Gly Met Phe Glu Ala Ile Ile Asn His Glu
```

| | | 145 | | | 150 | | | 155 | | | 160 |

Ser Glu Gln Ile Arg Pro Leu Asp Asn Ala Tyr Thr Asp Ile Leu Asn
                165                 170                 175

Lys Ala Val Lys Ile Arg Ser Thr Arg Ala Asn Gln Leu Ala Glu Leu
                180                 185                 190

Ala His Gln Arg Thr Arg Leu Gly Gly Met Phe Met Ile Gly Ala Phe
                195                 200                 205

Val Leu Ala Leu Val Met Thr Leu Ile Thr Phe Met Val Leu Arg Arg
        210                 215                 220

Ile Val Ile Arg Pro Leu Gln His Ala Ala Gln Arg Ile Glu Lys Ile
225                 230                 235                 240

Ala Ser Gly Asp Leu Thr Met Asn Asp Glu Pro Ala Gly Arg Asn Glu
                245                 250                 255

Ile Gly Arg Leu Ser Arg His Leu Gln His Met Ala Ala Gly Val Lys
                260                 265                 270

Gln Leu Ala Gly Gly Arg Thr Leu Leu Met Ala Gly Val Ser His Asp
        275                 280                 285

Leu Arg Thr Pro Leu Thr Val Leu Gln Gly Tyr Leu Glu Met Met Asn
        290                 295                 300

Glu Gln Pro Leu Glu Gly Ala Val Arg Glu Lys Ala Leu His Thr Met
305                 310                 315                 320

Arg Glu Gln Thr Gln Arg Met Asn Ala Ile Ile Glu Gln Phe Ile Asp
                325                 330                 335

Tyr Leu Arg Thr Gly Gln Glu Met Pro Met Glu Met Ala Asp Leu Asn
                340                 345                 350

Ala Val Leu Gly Glu Val Ile Ala Ala Glu Ser Gly Tyr Glu Arg Glu
        355                 360                 365

Ile Glu Thr Ala Leu Tyr Pro Gly Ser Ile Glu Val Lys Met His Pro
        370                 375                 380

Leu Ser Ile Lys Arg Ala Val Ala Asn Met Val Val Asn Ala Ala Arg
385                 390                 395                 400

Tyr Gly Asn Gly Trp Ile Lys Val Ser Ser Gly Thr Glu Pro Asn Arg
                405                 410                 415

Ala Trp Phe Gln Val Glu Asp Asp Gly Pro Gly Ile Ala Pro Glu Gln
                420                 425                 430

Arg Lys His Leu Phe Gln Pro Phe Val Arg Gly Asp Ser Ala Arg Thr
                435                 440                 445

Ile Ser Gly Thr Gly Leu Gly Leu Ala Ile Val Gln Arg Ile Val Asp
450                 455                 460

Asn His Asn Gly Met Leu Glu Leu Gly Thr Ser Glu Arg Gly Gly Leu
465                 470                 475                 480

Ser Ile Arg Ala Trp Leu Pro Val Pro Val Thr Arg Ala Gln Gly Thr
                485                 490                 495

Thr Lys Glu Gly
        500

<210> SEQ ID NO 15
<211> LENGTH: 1560
<212> TYPE: DNA
<213> ORGANISM: Artificial Sequence
<220> FEATURE:
<223> OTHER INFORMATION: Fusion protein coding sequence

<400> SEQUENCE: 15
atgaagttgc tttctaagac tttccttatt cttactctta cttctcttctt cttcggaatt        60

-continued

```
gctcttgcta agatgataaa ccgtattagg gttgttacct tgcttgttat ggttctaggt      120
gtattcgcct tgttacaact tatatcgggg tcactcttct tttcatcact ccatcatagt      180
cagaagagtt tcgtggtgtc taaccaactt agggagcaac agggtgaact gacttcaact      240
tgggatctga tgcttcagac aagaattaac ttgagcagaa gtgctgtgcg tatgatgatg      300
gatagtagca atcagcaatc aaatgcaaag gtggaacttc tggattcggc cagaaaaaca      360
ctggctcaag cggccacaca ctacaaaaag tttaagtcta tggcaccatt accagaaatg      420
gtggctacat cgcgaaatat cgacgagaag tacaaaaact actacactgc tctcacggaa      480
ctcattgatt acttagatta tggtaacacc ggtgcttact tgctcaacc tactcaagga      540 atgcagaacg ctatgggaga ggcattcgct caatatgcat atcctctga aaaactttat      600 agggacattg tcactgataa tgctgatgat tacagatttg cacagtggca attagcggtt      660
atcgctctgg tggtagtgct tattctgttg gtcgcttggt atgggattcg aagaatgttg      720
cttactccgc tcgctaagat tatcgcgcat ataagagaaa ttgccggtgg caatctcgct      780
aacacgctta caattgatgg gcgttcagag atgggcgatt tggcgcagtc tgtttctcat      840
atggcggctg tgttaagca actggaaggg gcgcggcgta acttttttgc caacgtgagc      900
catgagttac gtacgccatt gaccgtgtta cagggttacc tggagatgat gaatgagcag      960
ccgctggaag gcgcggtacg cgaaaaagcg ttgcacacca tgcgcgagca gcccagcgg     1020 atggaaggac tggtgaagca attgctgacg ctgtcgaaaa tagaagccgc accgacgcat     1080
ttgctcaatg aaaaggttga tgtgccgatg atgctgcgcg ttgttgagcg cgaggctcag     1140
actctgagtc agaaaaaaca gacatttacc tttgagatag ataacggcct caaggtgtct     1200
ggcaacgaag atcagctacg cagtgcgatt tcgaacctgg tctataacgc cgtgaatcat     1260
acgccggaag gcacgcatat caccgtacgc tggcagcgag tgccgcacgg tgccgaattt     1320
agcgttgaag ataacggacc gggcattgca ccggagcata ttccgcgcct gaccgagcgt     1380
ttttatcgcg ttgataaagc gcgttcccgg caaaccggcg gtagcggatt agggttagcg     1440
atcgtgaaac atgctgtgaa tcatcacgaa agtcgcctga atattgagag tacagtagga     1500
aaaggaacac gtttcagttt tgttatcccg gaacgtttaa ttgccaaaaa cagcgattaa     1560
```

<210> SEQ ID NO 16
<211> LENGTH: 519
<212> TYPE: PRT
<213> ORGANISM: Artificial Sequence
<220> FEATURE:
<223> OTHER INFORMATION: Fusion protein

<400> SEQUENCE: 16

Met Lys Leu Leu Ser Lys Thr Phe Leu Ile Leu Thr Leu Thr Phe Phe
1               5                   10                  15

Phe Phe Gly Ile Ala Leu Ala Lys Met Ile Asn Arg Ile Arg Val Val
                20                  25                  30

Thr Leu Leu Val Met Val Leu Gly Val Phe Ala Leu Leu Gln Leu Ile
            35                  40                  45

Ser Gly Ser Leu Phe Phe Ser Ser Leu His His Ser Gln Lys Ser Phe
        50                  55                  60

Val Val Ser Asn Gln Leu Arg Glu Gln Gln Gly Glu Leu Thr Ser Thr
65                  70                  75                  80

Trp Asp Leu Met Leu Gln Thr Arg Ile Asn Leu Ser Arg Ser Ala Val
                85                  90                  95

```
Arg Met Met Met Asp Ser Ser Asn Gln Gln Ser Asn Ala Lys Val Glu
            100                 105                 110

Leu Leu Asp Ser Ala Arg Lys Thr Leu Ala Gln Ala Ala Thr His Tyr
        115                 120                 125

Lys Lys Phe Lys Ser Met Ala Pro Leu Pro Glu Met Val Ala Thr Ser
        130                 135                 140

Arg Asn Ile Asp Glu Lys Tyr Lys Asn Tyr Tyr Thr Ala Leu Thr Glu
145                 150                 155                 160

Leu Ile Asp Tyr Leu Asp Tyr Gly Asn Thr Gly Ala Tyr Phe Ala Gln
                165                 170                 175

Pro Thr Gln Gly Met Gln Asn Ala Met Gly Glu Ala Phe Ala Gln Tyr
            180                 185                 190

Ala Leu Ser Ser Glu Lys Leu Tyr Arg Asp Ile Val Thr Asp Asn Ala
        195                 200                 205

Asp Asp Tyr Arg Phe Ala Gln Trp Gln Leu Ala Val Ile Ala Leu Val
210                 215                 220

Val Val Leu Ile Leu Leu Val Ala Trp Tyr Gly Ile Arg Arg Met Leu
225                 230                 235                 240

Leu Thr Pro Leu Ala Lys Ile Ile Ala His Ile Arg Glu Ile Ala Gly
                245                 250                 255

Gly Asn Leu Ala Asn Thr Leu Thr Ile Asp Gly Arg Ser Glu Met Gly
            260                 265                 270

Asp Leu Ala Gln Ser Val Ser His Met Ala Ala Gly Val Lys Gln Leu
        275                 280                 285

Glu Gly Ala Arg Arg Asn Phe Phe Ala Asn Val Ser His Glu Leu Arg
        290                 295                 300

Thr Pro Leu Thr Val Leu Gln Gly Tyr Leu Glu Met Met Asn Glu Gln
305                 310                 315                 320

Pro Leu Glu Gly Ala Val Arg Glu Lys Ala Leu His Thr Met Arg Glu
                325                 330                 335

Gln Thr Gln Arg Met Glu Gly Leu Val Lys Gln Leu Leu Thr Leu Ser
            340                 345                 350

Lys Ile Glu Ala Ala Pro Thr His Leu Leu Asn Glu Lys Val Asp Val
        355                 360                 365

Pro Met Met Leu Arg Val Val Glu Arg Glu Ala Gln Thr Leu Ser Gln
370                 375                 380

Lys Lys Gln Thr Phe Thr Phe Glu Ile Asp Asn Gly Leu Lys Val Ser
385                 390                 395                 400

Gly Asn Glu Asp Gln Leu Arg Ser Ala Ile Ser Asn Leu Val Tyr Asn
                405                 410                 415

Ala Val Asn His Thr Pro Glu Gly Thr His Ile Thr Val Arg Trp Gln
            420                 425                 430

Arg Val Pro His Gly Ala Glu Phe Ser Val Glu Asp Asn Gly Pro Gly
        435                 440                 445

Ile Ala Pro Glu His Ile Pro Arg Leu Thr Glu Arg Phe Tyr Arg Val
        450                 455                 460

Asp Lys Ala Arg Ser Arg Gln Thr Gly Gly Ser Gly Leu Gly Leu Ala
465                 470                 475                 480

Ile Val Lys His Ala Val Asn His His Glu Ser Arg Leu Asn Ile Glu
                485                 490                 495

Ser Thr Val Gly Lys Gly Thr Arg Phe Ser Phe Val Ile Pro Glu Arg
            500                 505                 510

Leu Ile Ala Lys Asn Ser Asp
```

<210> SEQ ID NO 17
<211> LENGTH: 1551
<212> TYPE: DNA
<213> ORGANISM: Artificial Sequence
<220> FEATURE:
<223> OTHER INFORMATION: Fusion protein coding sequence

<400> SEQUENCE: 17

```
atgaagttgc tttctaagac tttccttatt cttactctta ctttcttctt cttcggaatt    60
gctcttgcta agatgataaa ccgtattagg gttgttacct tgcttgttat ggttctaggt   120
gtattcgcct tgttacaact tatatcgggg tcactcttct tttcatcact ccatcatagt   180
cagaagagtt tcgtggtgtc taaccaactt agggagcaac agggtgaact gacttcaact   240
tgggatctga tgcttcagac aagaattaac ttgagcagaa gtgctgtgcg tatgatgatg   300
gatagtagca atcagcaatc aaatgcaaag gtggaacttc tggattcggc cagaaaaaca   360
ctggctcaag cggccacaca ctacaaaaag tttaagtcta tggcaccatt accagaaatg   420
gtggctacat cgcgaaatat cgacgagaag tacaaaaact actacactgc tctcacggaa   480
ctcattgatt acttagatta tggtaacacc ggtgcttact tgctcaacc tactcaagga   540
atgcagaacg ctatgggaga ggcattcgct caatatgcat atcctctga aaaactttat   600
agggacattg tcactgataa tgctgatgat tacagatttg cacagtggca attagcggtt   660
atcgctctgg tggtagtgct tattctgttg gtcgcttggt atgggattcg aagaatgttg   720
cttactccgc tcgctaagat tatcgcgcat ataagagaaa ttgccggtgg caatctcgct   780
aacacgctta caattgatgg gcgttcagag atgggcgatt ggcgcagtc tgtttctcat   840
atggcggctg tgttaagca actgcggcgt aacttttttg ccaacgtgag ccatgagtta   900
cgtacgccat tgaccgtgtt acagggctac ctggagatga tgaatgagca gccgctggaa   960
ggcgcggtac gcgaaaaagc gttgcacacc atgcgcgagc agacccagcg gatggaagga  1020
ctggtgaagc aattgctgac gctgtcgaaa atagaagccg caccgacgca tttgctcaat  1080
gaaaaggttg atgtgccgat gatgctgcgc gttgttgagc gcgaggctca gactctgagt  1140
cagaaaaaac agacatttac ctttgagata gataacggcc tcaaggtgtc tggcaacgaa  1200
gatcagctac gcagtgcgat ttcgaacctg gtctataacg ccgtgaatca tacgccggaa  1260
ggcacgcata tcaccgtacg ctggcagcga gtgccgcacg gtgccgaatt tagcgttgaa  1320
gataacggac cgggcattgc accggagcat attccgcgcc tgaccgagcg ttttttatcgc  1380
gttgataaag cgcgttcccg gcaaaccggc ggtagcggat tagggttagc gatcgtgaaa  1440
catgctgtga atcatcacga aagtcgcctg aatattgaga gtacagtagg aaaaggaaca  1500
cgtttcagtt ttgttatccc ggaacgttta attgccaaaa acagcgatta a           1551
```

<210> SEQ ID NO 18
<211> LENGTH: 516
<212> TYPE: PRT
<213> ORGANISM: Artificial Sequence
<220> FEATURE:
<223> OTHER INFORMATION: Fusion protein

<400> SEQUENCE: 18

```
Met Lys Leu Leu Ser Lys Thr Phe Leu Ile Leu Thr Leu Thr Phe Phe
 1               5                  10                  15

Phe Phe Gly Ile Ala Leu Ala Lys Met Ile Asn Arg Ile Arg Val Val
            20                  25                  30
```

```
Thr Leu Leu Val Met Val Leu Gly Val Phe Ala Leu Leu Gln Leu Ile
        35                  40                  45

Ser Gly Ser Leu Phe Phe Ser Ser Leu His His Ser Gln Lys Ser Phe
        50                  55                  60

Val Val Ser Asn Gln Leu Arg Glu Gln Gln Gly Glu Leu Thr Ser Thr
 65                  70                  75                  80

Trp Asp Leu Met Leu Gln Thr Arg Ile Asn Leu Ser Arg Ser Ala Val
                85                  90                  95

Arg Met Met Met Asp Ser Ser Asn Gln Gln Ser Asn Ala Lys Val Glu
                    100                 105                 110

Leu Leu Asp Ser Ala Arg Lys Thr Leu Ala Gln Ala Thr His Tyr
            115                 120                 125

Lys Lys Phe Lys Ser Met Ala Pro Leu Pro Glu Met Val Ala Thr Ser
        130                 135                 140

Arg Asn Ile Asp Glu Lys Tyr Lys Asn Tyr Tyr Thr Ala Leu Thr Glu
145                 150                 155                 160

Leu Ile Asp Tyr Leu Asp Tyr Gly Asn Thr Gly Ala Tyr Phe Ala Gln
                165                 170                 175

Pro Thr Gln Gly Met Gln Asn Ala Met Gly Glu Ala Phe Ala Gln Tyr
            180                 185                 190

Ala Leu Ser Ser Glu Lys Leu Tyr Arg Asp Ile Val Thr Asp Asn Ala
        195                 200                 205

Asp Asp Tyr Arg Phe Ala Gln Trp Gln Leu Ala Val Ile Ala Leu Val
210                 215                 220

Val Val Leu Ile Leu Leu Val Ala Trp Tyr Gly Ile Arg Arg Met Leu
225                 230                 235                 240

Leu Thr Pro Leu Ala Lys Ile Ile Ala His Ile Arg Glu Ile Ala Gly
                245                 250                 255

Gly Asn Leu Ala Asn Thr Leu Thr Ile Asp Gly Arg Ser Glu Met Gly
            260                 265                 270

Asp Leu Ala Gln Ser Val Ser His Met Ala Ala Gly Val Lys Gln Leu
        275                 280                 285

Arg Arg Asn Phe Phe Ala Asn Val Ser His Glu Leu Arg Thr Pro Leu
        290                 295                 300

Thr Val Leu Gln Gly Tyr Leu Glu Met Met Asn Glu Gln Pro Leu Glu
305                 310                 315                 320

Gly Ala Val Arg Glu Lys Ala Leu His Thr Met Arg Glu Gln Thr Gln
                325                 330                 335

Arg Met Glu Gly Leu Val Lys Gln Leu Leu Thr Leu Ser Lys Ile Glu
            340                 345                 350

Ala Ala Pro Thr His Leu Leu Asn Glu Lys Val Asp Val Pro Met Met
        355                 360                 365

Leu Arg Val Val Glu Arg Glu Ala Gln Thr Leu Ser Gln Lys Lys Gln
    370                 375                 380

Thr Phe Thr Phe Glu Ile Asp Asn Gly Leu Lys Val Ser Gly Asn Glu
385                 390                 395                 400

Asp Gln Leu Arg Ser Ala Ile Ser Asn Leu Val Tyr Asn Ala Val Asn
                405                 410                 415

His Thr Pro Glu Gly Thr His Ile Thr Val Arg Trp Gln Arg Val Pro
            420                 425                 430

His Gly Ala Glu Phe Ser Val Glu Asp Asn Gly Pro Gly Ile Ala Pro
        435                 440                 445
```

```
Glu His Ile Pro Arg Leu Thr Glu Arg Phe Tyr Arg Val Asp Lys Ala
    450                 455                 460

Arg Ser Arg Gln Thr Gly Gly Ser Gly Leu Gly Leu Ala Ile Val Lys
465                 470                 475                 480

His Ala Val Asn His His Glu Ser Arg Leu Asn Ile Glu Ser Thr Val
                485                 490                 495

Gly Lys Gly Thr Arg Phe Ser Phe Val Ile Pro Glu Arg Leu Ile Ala
            500                 505                 510

Lys Asn Ser Asp
        515

<210> SEQ ID NO 19
<211> LENGTH: 1560
<212> TYPE: DNA
<213> ORGANISM: Artificial Sequence
<220> FEATURE:
<223> OTHER INFORMATION: Fusion protein coding sequence

<400> SEQUENCE: 19
atgaagttgc tttctaagac tttccttatt cttactctta ctttcttctt cttcggaatt      60
gctcttgcta agatgataaa ccgtattagg gttgttacct tgcttgttat ggttctaggt     120
gtattcgcct tgttacaact tatatcgggg tcactcttct tttcatcact ccatcatagt     180
cagaagagtt tcgtggtgtc taaccaactt agggagcaac agggtgaact gacttcaact     240
tgggatctga tgcttcagac aagaattaac ttgagcagaa gtgctgtgcg tatgatgatg     300
gatagtagca atcagcaatc aaatgcaaag gtggaacttc tggattcggc cagaaaaaca     360
ctggctcaag cggccacaca ctacaaaaag tttaagtcta tggcaccatt accagaaatg     420
gtggctacat cgcgaaatat cgacgagaag tacaaaaact actacactgc tctcacggaa     480
ctcattgatt acttagatta tggtaacacc ggtgcttact tgctcaacc tactcaagga      540
atgcagaacg ctatgggaga ggcattcgct caatatgcat atcctctga aaaactttat      600
agggacattg tcactgataa tgctgatgat tacagatttg cacagtggca attagcggtt     660
atcgctctgg tggtagtgct tattctgttg gtcgcttggt atgggattcg aagaatgttg     720
cttactccgc tcgctaagat tatcgcgcat ataagagaaa ttgccggtgg caatctcgct     780
aacacgctta caattgatgg gcgttcagag atgggcgatt tggcgcagtc tgtttctcat     840
atggcggctg tgttaagca actgcgggtg tggcggcgta actttttgc caacgtgagc       900
catgagttac gtacgccatt gaccgtgtta cagggctacc tggagatgat gaatgagcag     960
ccgctggaag gcgcggtacg cgaaaaagcg ttgcacacca tgcgcagcagaa cccagcgg   1020
atggaaggac tggtgaagca attgctgacg ctgtcgaaaa tagaagccgc accgacgcat    1080
ttgctcaatg aaaaggttga tgtgccgatg atgctgcgcg ttgttgagcg cgaggctcag    1140
actctgagtc agaaaaaaca gacatttacc tttgagatag ataacggcct caaggtgtct    1200
ggcaacgaag atcagctacg cagtgcgatt tcgaacctgg tctataacgc cgtgaatcat    1260
acgccggaag gcacgcatat caccgtacgc tggcagcgag tgccgcacgg tgccgaattt    1320
agcgttgaag ataacggacc gggcattgca ccggagcata ttccgcgcct gaccgagcgt    1380
ttttatcgcg ttgataaagc gcgttccgg caaaccggcg gtagcggatt agggttagcg     1440
atcgtgaaac atgctgtgaa tcatcacgaa agtcgcctga atattgagag tacagtagga    1500
aaaggaacac gtttcagttt tgttatcccg gaacgtttaa ttgccaaaaa cagcgattaa    1560

<210> SEQ ID NO 20
```

```
<211> LENGTH: 519
<212> TYPE: PRT
<213> ORGANISM: Artificial Sequence
<220> FEATURE:
<223> OTHER INFORMATION: Fusion protein

<400> SEQUENCE: 20
```

Met Lys Leu Leu Ser Lys Thr Phe Leu Ile Leu Thr Leu Thr Phe Phe
1               5                   10                  15

Phe Phe Gly Ile Ala Leu Ala Lys Met Ile Asn Arg Ile Arg Val Val
            20                  25                  30

Thr Leu Leu Val Met Val Leu Gly Val Phe Ala Leu Leu Gln Leu Ile
        35                  40                  45

Ser Gly Ser Leu Phe Phe Ser Ser Leu His His Ser Gln Lys Ser Phe
    50                  55                  60

Val Val Ser Asn Gln Leu Arg Glu Gln Gln Gly Glu Leu Thr Ser Thr
65                  70                  75                  80

Trp Asp Leu Met Leu Gln Thr Arg Ile Asn Leu Ser Arg Ser Ala Val
                85                  90                  95

Arg Met Met Met Asp Ser Ser Asn Gln Gln Ser Asn Ala Lys Val Glu
            100                 105                 110

Leu Leu Asp Ser Ala Arg Lys Thr Leu Ala Gln Ala Ala Thr His Tyr
        115                 120                 125

Lys Lys Phe Lys Ser Met Ala Pro Leu Pro Glu Met Val Ala Thr Ser
    130                 135                 140

Arg Asn Ile Asp Glu Lys Tyr Lys Asn Tyr Tyr Thr Ala Leu Thr Glu
145                 150                 155                 160

Leu Ile Asp Tyr Leu Asp Tyr Gly Asn Thr Gly Ala Tyr Phe Ala Gln
                165                 170                 175

Pro Thr Gln Gly Met Gln Asn Ala Met Gly Glu Ala Phe Ala Gln Tyr
            180                 185                 190

Ala Leu Ser Ser Glu Lys Leu Tyr Arg Asp Ile Val Thr Asp Asn Ala
        195                 200                 205

Asp Asp Tyr Arg Phe Ala Gln Trp Gln Leu Ala Val Ile Ala Leu Val
210                 215                 220

Val Val Leu Ile Leu Leu Val Ala Trp Tyr Gly Ile Arg Arg Met Leu
225                 230                 235                 240

Leu Thr Pro Leu Ala Lys Ile Ile Ala His Ile Arg Glu Ile Ala Gly
                245                 250                 255

Gly Asn Leu Ala Asn Thr Leu Thr Ile Asp Gly Arg Ser Glu Met Gly
            260                 265                 270

Asp Leu Ala Gln Ser Val Ser His Met Ala Ala Gly Val Lys Gln Leu
        275                 280                 285

Arg Val Trp Arg Arg Asn Phe Phe Ala Asn Val Ser His Glu Leu Arg
    290                 295                 300

Thr Pro Leu Thr Val Leu Gln Gly Tyr Leu Glu Met Met Asn Glu Gln
305                 310                 315                 320

Pro Leu Glu Gly Ala Val Arg Glu Lys Ala Leu His Thr Met Arg Glu
                325                 330                 335

Gln Thr Arg Met Glu Gly Leu Val Lys Gln Leu Leu Thr Leu Ser
            340                 345                 350

Lys Ile Glu Ala Ala Pro Thr His Leu Leu Asn Glu Lys Val Asp Val
    355                 360                 365

Pro Met Met Leu Arg Val Val Glu Arg Glu Ala Gln Thr Leu Ser Gln
370                 375                 380

Lys Lys Gln Thr Phe Thr Phe Glu Ile Asp Asn Gly Leu Lys Val Ser
385                 390                 395                 400

Gly Asn Glu Asp Gln Leu Arg Ser Ala Ile Ser Asn Leu Val Tyr Asn
            405                 410                 415

Ala Val Asn His Thr Pro Glu Gly Thr His Ile Thr Val Arg Trp Gln
            420                 425                 430

Arg Val Pro His Gly Ala Glu Phe Ser Val Glu Asp Asn Gly Pro Gly
            435                 440                 445

Ile Ala Pro Glu His Ile Pro Arg Leu Thr Glu Arg Phe Tyr Arg Val
            450                 455                 460

Asp Lys Ala Arg Ser Arg Gln Thr Gly Gly Ser Gly Leu Gly Leu Ala
465                 470                 475                 480

Ile Val Lys His Ala Val Asn His His Glu Ser Arg Leu Asn Ile Glu
            485                 490                 495

Ser Thr Val Gly Lys Gly Thr Arg Phe Ser Phe Val Ile Pro Glu Arg
            500                 505                 510

Leu Ile Ala Lys Asn Ser Asp
        515

<210> SEQ ID NO 21
<211> LENGTH: 1473
<212> TYPE: DNA
<213> ORGANISM: Artificial Sequence
<220> FEATURE:
<223> OTHER INFORMATION: Fusion protein coding sequence

<400> SEQUENCE: 21
atgattaacc gtatccgcgt agtcacgctg ttggtaatgg tcctgggggt attcgcactg      60
ttacagctta tttccggcag tctgtttttt tcttcccttc accatagcca gaagagcttt     120
gtggtttcca atcaattacg ggaacagcag ggcgagctga cgtcaacctg ggatttaatg     180
ctgcaaacgc gcattaacct gagtcgttca gcgtacgga tgatgatgga ttcctccaat     240
caacaaagta acgccaaagt tgaattgctc gatagcgcca ggaaaacatt ggcgcaggca     300
gcgacgcatt ataaaaaatt caaaagcatg gcaccgttac tgaaatggt cgctaccagt     360
cgtaatattg atgaaaaata taaaaactat tacacagcgt taactgaact gattgattat     420
ctagattatg gcaatactgg agcttatttc gctcagccaa cccagggaat gcaaaatgca     480
atgggcgaac ggtttgctca gtacgccctc agcagtgaaa aactgtatcg cgatattgtc     540
actgacaacg cagatgatta ccgatttgcc cagtggcaac tggcggttat cgcgctggtg     600
gtggtattga ttctgctggt ggcgtggtac ggcattcgcc gtatgttgct tactccgctg     660
gcaaaaatta ttgctcacat tcgcgaaatc gccggtggca acctggcgaa tacccctgacc    720
attgacgggc gcagtgaaat gggcgacctg gcgcagagcg tttcacatat ggcggctggt     780
gttaagcaac tgcgaggggt gcgcacgctg ctgatggcgg ggtaagtca cgacttgcgc     840
acgccgctga cggtgttaca gggttacctg agatgatga atgagcagcc gctggaaggc     900
gcggtacgcg aaaaagcgtt gcacaccatg cgcgagcaga cccagcggat gaacgccatc     960
attgagcagt ttatcgacta cctgcgcacc gggcaggaga tgccgatgga aatggcggat    1020
cttaatgcag tactcggtga ggtgattgct gccgaaagtg gctatgagcg ggaaattgaa    1080
accgcgcttt accccggcag cattgaagtg aaaatgcacc cgctgtcgat caaacgcgcg    1140
gtggcgaata tggtggtcaa cgccgcccgt tatggcaatg gctggatcaa agtcagcagc    1200
ggaacggagc cgaatcgcgc ctggttccag gtggaagatg acggtccggg aattgcgccg    1260

```
gaacaacgta agcacctgtt ccagccgttt gtccgcggcg acagtgcgcg caccattagc      1320
ggcacgggat tagggctggc aattgtgcag cgtatcgtgg ataaccataa cgggatgctg      1380
gagcttggca ccagcgagcg gggcgggctt tccattcgcg cctggctgcc agtgccggta      1440
acgcgggcgc agggcacgac aaaagaaggg taa                                   1473
```

<210> SEQ ID NO 22
<211> LENGTH: 490
<212> TYPE: PRT
<213> ORGANISM: Artificial Sequence
<220> FEATURE:
<223> OTHER INFORMATION: Fusion protein

<400> SEQUENCE: 22

```
Met Ile Asn Arg Ile Arg Val Val Thr Leu Leu Val Met Val Leu Gly
1               5                   10                  15

Val Phe Ala Leu Leu Gln Leu Ile Ser Gly Ser Leu Phe Phe Ser Ser
            20                  25                  30

Leu His His Ser Gln Lys Ser Phe Val Val Ser Asn Gln Leu Arg Glu
        35                  40                  45

Gln Gln Gly Glu Leu Thr Ser Thr Trp Asp Leu Met Leu Gln Thr Arg
    50                  55                  60

Ile Asn Leu Ser Arg Ser Ala Val Arg Met Met Met Asp Ser Ser Asn
65                  70                  75                  80

Gln Gln Ser Asn Ala Lys Val Glu Leu Leu Asp Ser Ala Arg Lys Thr
                85                  90                  95

Leu Ala Gln Ala Ala Thr His Tyr Lys Lys Phe Lys Ser Met Ala Pro
            100                 105                 110

Leu Pro Glu Met Val Ala Thr Ser Arg Asn Ile Asp Glu Lys Tyr Lys
        115                 120                 125

Asn Tyr Tyr Thr Ala Leu Thr Glu Leu Ile Asp Tyr Leu Asp Tyr Gly
    130                 135                 140

Asn Thr Gly Ala Tyr Phe Ala Gln Pro Thr Gln Gly Met Gln Asn Ala
145                 150                 155                 160

Met Gly Glu Arg Phe Ala Gln Tyr Ala Leu Ser Ser Glu Lys Leu Tyr
                165                 170                 175

Arg Asp Ile Val Thr Asp Asn Ala Asp Asp Tyr Arg Phe Ala Gln Trp
            180                 185                 190

Gln Leu Ala Val Ile Ala Leu Val Val Leu Ile Leu Leu Val Ala
        195                 200                 205

Trp Tyr Gly Ile Arg Arg Met Leu Leu Thr Pro Leu Ala Lys Ile Ile
    210                 215                 220

Ala His Ile Arg Glu Ile Ala Gly Gly Asn Leu Ala Asn Thr Leu Thr
225                 230                 235                 240

Ile Asp Gly Arg Ser Glu Met Gly Asp Leu Ala Gln Ser Val Ser His
                245                 250                 255

Met Ala Ala Gly Val Lys Gln Leu Arg Gly Val Arg Thr Leu Leu Met
            260                 265                 270

Ala Gly Val Ser His Asp Leu Arg Thr Pro Leu Thr Val Leu Gln Gly
        275                 280                 285

Tyr Leu Glu Met Met Asn Glu Gln Pro Leu Glu Gly Ala Val Arg Glu
    290                 295                 300

Lys Ala Leu His Thr Met Arg Glu Gln Thr Gln Arg Met Asn Ala Ile
305                 310                 315                 320
```

```
Ile Glu Gln Phe Ile Asp Tyr Leu Arg Thr Gly Gln Glu Met Pro Met
                325                 330                 335

Glu Met Ala Asp Leu Asn Ala Val Leu Gly Glu Val Ile Ala Ala Glu
            340                 345                 350

Ser Gly Tyr Glu Arg Glu Ile Glu Thr Ala Leu Tyr Pro Gly Ser Ile
        355                 360                 365

Glu Val Lys Met His Pro Leu Ser Ile Lys Arg Ala Val Ala Asn Met
    370                 375                 380

Val Val Asn Ala Ala Arg Tyr Gly Asn Gly Trp Ile Lys Val Ser Ser
385                 390                 395                 400

Gly Thr Glu Pro Asn Arg Ala Trp Phe Gln Val Glu Asp Asp Gly Pro
                405                 410                 415

Gly Ile Ala Pro Glu Gln Arg Lys His Leu Phe Gln Pro Phe Val Arg
            420                 425                 430

Gly Asp Ser Ala Arg Thr Ile Ser Gly Thr Gly Leu Gly Leu Ala Ile
        435                 440                 445

Val Gln Arg Ile Val Asp Asn His Asn Gly Met Leu Glu Leu Gly Thr
    450                 455                 460

Ser Glu Arg Gly Gly Leu Ser Ile Arg Ala Trp Leu Pro Val Pro Val
465                 470                 475                 480

Thr Arg Ala Gln Gly Thr Thr Lys Glu Gly
                485                 490

<210> SEQ ID NO 23
<211> LENGTH: 1473
<212> TYPE: DNA
<213> ORGANISM: Artificial Sequence
<220> FEATURE:
<223> OTHER INFORMATION: Fusion protein coding sequence

<400> SEQUENCE: 23
atgattaacc gtatacgcgt agtcacgctg ttggtaatgg tcctgggggt attcgcactg      60
ttacagctta tttccggcag tctgtttttt tcttcccttc accatagcca gaagagcttt     120
gtggtttcca atcaattacg ggaacagcag ggcgagctga cgtcaacctg ggatttaatg     180
ctgcaaacgc gcattaacct gagtcgttca gcggtacgga tgatgatgga ttcctccaat     240
caacaaagta cgccaaagt tgaattgctc gatagcgcca ggaaaacatt ggcgcaggca     300
gcgacgcatt ataaaaaatt caaaagcatg caccgttac tgaaatggt cgctaccagt     360 cgtaatattg atgaaaaata taaaaactat tacacagcgt taactgaact gattgattat     420
ctagattatg caatactgg agcttatttc gctcagccaa cccagggaat gcaaaatgca     480
atgggcgaac ggtttgctca gtacgccctc agcagtgaaa aactgtatcg cgatattgtc     540
actgacaacg cagatgatta ccgatttgcc cagtggcaac tggcggttat cgcactagtg     600
gtggtattga ttctgctggg ggcgtggtac ggcattcgcc gtatgttgct tactccgctg     660
gcaaaaatta ttgctcacat tcgcgaaatc gccgtggca acctggcgaa taccctgacc     720
attgacgggc gcagtgaaat gggcgacctg gcgcagagcg tttcacatat ggcggctggt     780
gttaagcaac tggtgtggcg gcgcacgctg ctgatggcgg ggtaagtca cgacttgcgc     840 acgccgctga cggtgttaca gggttacctg agatgatga tgagcagcc gctggaaggc     900 gcggtacgcg aaaaagcgtt gcacaccatg cgcgagcaga cccagcggat gaacgccatc     960
attgagcagt ttatcgacta cctgcgcacc gggcaggaga tgccgatgga aatggcggat    1020
cttaatgcag tactcggtga ggtgattgct gccgaaagtg gctatgagcg ggaaattgaa    1080
```

```
accgcgcttt accccggatc cattgaagtg aaaatgcacc cgctgtcgat caaacgcgcg    1140
gtggcgaata tggtggtcaa cgccgcccgt tatggcaatg gctggatcaa agtcagcagc    1200
ggaacggagc cgaatcgcgc ctggttccag gtggaagatg acggtccggg aattgcgccg    1260
gaacaacgta agcacctgtt ccagccgttt gtccgcggcg acagtgcgcg caccattagc    1320
ggcacgggat tagggctggc aattgtgcag cgtatcgtgg ataaccataa cgggatgctg    1380
gagcttggca ccagcgagcg gggcgggctt tccattcgcg cctggctgcc agtgccggta    1440
acgcgggcgc agggcacgac aaaagaaggg taa                                 1473
```

<210> SEQ ID NO 24
<211> LENGTH: 490
<212> TYPE: PRT
<213> ORGANISM: Artificial Sequence
<220> FEATURE:
<223> OTHER INFORMATION: Fusion protein

<400> SEQUENCE: 24

```
Met Ile Asn Arg Ile Arg Val Val Thr Leu Leu Val Met Val Leu Gly
1               5                   10                  15

Val Phe Ala Leu Leu Gln Leu Ile Ser Gly Ser Leu Phe Phe Ser Ser
            20                  25                  30

Leu His His Ser Gln Lys Ser Phe Val Val Ser Asn Gln Leu Arg Glu
        35                  40                  45

Gln Gln Gly Glu Leu Thr Ser Thr Trp Asp Leu Met Leu Gln Thr Arg
    50                  55                  60

Ile Asn Leu Ser Arg Ser Ala Val Arg Met Met Met Asp Ser Ser Asn
65                  70                  75                  80

Gln Gln Ser Asn Ala Lys Val Glu Leu Leu Asp Ser Ala Arg Lys Thr
                85                  90                  95

Leu Ala Gln Ala Ala Thr His Tyr Lys Lys Phe Lys Ser Met Ala Pro
            100                 105                 110

Leu Pro Glu Met Val Ala Thr Ser Arg Asn Ile Asp Glu Lys Tyr Lys
        115                 120                 125

Asn Tyr Tyr Thr Ala Leu Thr Glu Leu Ile Asp Tyr Leu Asp Tyr Gly
    130                 135                 140

Asn Thr Gly Ala Tyr Phe Ala Gln Pro Thr Gln Gly Met Gln Asn Ala
145                 150                 155                 160

Met Gly Glu Arg Phe Ala Gln Tyr Ala Leu Ser Ser Glu Lys Leu Tyr
                165                 170                 175

Arg Asp Ile Val Thr Asp Asn Ala Asp Asp Tyr Arg Phe Ala Gln Trp
            180                 185                 190

Gln Leu Ala Val Ile Ala Leu Val Val Val Leu Ile Leu Leu Val Ala
        195                 200                 205

Trp Tyr Gly Ile Arg Arg Met Leu Leu Thr Pro Leu Ala Lys Ile Ile
    210                 215                 220

Ala His Ile Arg Glu Ile Ala Gly Gly Asn Leu Ala Asn Thr Leu Thr
225                 230                 235                 240

Ile Asp Gly Arg Ser Glu Met Gly Asp Leu Ala Gln Ser Val Ser His
                245                 250                 255

Met Ala Ala Gly Val Lys Gln Leu Val Trp Arg Arg Thr Leu Leu Met
            260                 265                 270

Ala Gly Val Ser His Asp Leu Arg Thr Pro Leu Thr Val Leu Gln Gly
        275                 280                 285

Tyr Leu Glu Met Met Asn Glu Gln Pro Leu Glu Gly Ala Val Arg Glu
```

```
        290             295             300
Lys Ala Leu His Thr Met Arg Glu Gln Thr Gln Arg Met Asn Ala Ile
305                 310                 315                 320

Ile Glu Gln Phe Ile Asp Tyr Leu Arg Thr Gly Gln Glu Met Pro Met
                325                 330                 335

Glu Met Ala Asp Leu Asn Ala Val Leu Gly Glu Val Ile Ala Ala Glu
                340                 345                 350

Ser Gly Tyr Glu Arg Glu Ile Glu Thr Ala Leu Tyr Pro Gly Ser Ile
            355                 360                 365

Glu Val Lys Met His Pro Leu Ser Ile Lys Arg Ala Val Ala Asn Met
        370                 375                 380

Val Val Asn Ala Ala Arg Tyr Gly Asn Gly Trp Ile Lys Val Ser Ser
385                 390                 395                 400

Gly Thr Glu Pro Asn Arg Ala Trp Phe Gln Val Glu Asp Asp Gly Pro
                405                 410                 415

Gly Ile Ala Pro Glu Gln Arg Lys His Leu Phe Gln Pro Phe Val Arg
            420                 425                 430

Gly Asp Ser Ala Arg Thr Ile Ser Gly Thr Gly Leu Gly Leu Ala Ile
        435                 440                 445

Val Gln Arg Ile Val Asp Asn His Asn Gly Met Leu Glu Leu Gly Thr
    450                 455                 460

Ser Glu Arg Gly Gly Leu Ser Ile Arg Ala Trp Leu Pro Val Pro Val
465                 470                 475                 480

Thr Arg Ala Gln Gly Thr Thr Lys Glu Gly
                485                 490

<210> SEQ ID NO 25
<211> LENGTH: 1296
<212> TYPE: DNA
<213> ORGANISM: E. coli

<400> SEQUENCE: 25
atgctggaac ggctgtcgtg aaaaggctg gtgctggagc tgctactttg ctgcctcccg      60
gctttcatcc tgggtgcatt ttttggttac ctgccctggt ttttgctggc atcggtaaca     120
ggactgctta tctggcattt ctggaattta ttgcgccttt catggtggct gtgggtggat     180
cgcagtatga ccccgccacc ggggcgtggt agctgggaac cgctactata cggcttacac     240
cagatgcagc tgcgaaataa aaacgccgc cgtgaactgg caatctgat taaacgcttt      300 cgtagcggcg cggagtcgct gcccgacgcg gtggtgctga ccacggaaga gggcggtatt     360
ttctggtgta acggtctggc gcaacaaatt cttggtttgc gctggccgga agataacggg     420
cagaacatcc ttaacctact gcgttacccg gagtttacgc aatatctgaa acgcgtgat     480 ttttctcgcc cgctcaatct ggtgctcaac accgggcggc atctggaaat cgcgtcatg     540 cctatacccc acaaacagtt gctgatggtg gcgcgtgatg tcacgcaaat gcatcaactg     600 gaagggcgc ggcgtaactt ttttgccaac gtgagccatg agttacgtac gccattgacc     660
gtgttacagg gttacctgga tgatgatgaat gagcagccgc tggaaggcgc ggtacgcgaa     720
aaagcgttgc acaccatgcg cgagcagacc cagcggatgg aaggactggt gaagcaattg     780
ctgacgctgt cgaaaataga agccgcaccg acgcatttgc tcaatgaaaa ggttgatgtg     840
ccgatgatgc tgcgcgttgt tgagcgcgag gctcagactc tgagtcagaa aaaacagaca     900 tttaccttg atagataaa cggcctcaag gtgtctggca acgaagatca gctacgcagt     960
gcgatttcga acctggtcta taacgccgtg aatcatacgc cggaaggcac gcatatcacc    1020
```

```
gtacgctggc agcgagtgcc gcacggtgcc gaatttagcg ttgaagataa cggaccgggc   1080
attgcaccgg agcatattcc gcgcctgacc gagcgttttt atcgcgttga taaagcgcgt   1140
tcccggcaaa ccggcggtag cggattaggg ttagcgatcg tgaaacatgc tgtgaatcat   1200
cacgaaagtc gcctgaatat tgagagtaca gtaggaaaag gaacacgttt cagttttgtt   1260
atcccggaac gtttaattgc caaaaacagc gattaa                              1296
```

<210> SEQ ID NO 26
<211> LENGTH: 431
<212> TYPE: PRT
<213> ORGANISM: E. coli

<400> SEQUENCE: 26

```
Val Leu Glu Arg Leu Ser Trp Lys Arg Leu Val Leu Glu Leu Leu
1               5                   10                  15

Cys Cys Leu Pro Ala Phe Ile Leu Gly Ala Phe Phe Gly Tyr Leu Pro
                20                  25                  30

Trp Phe Leu Leu Ala Ser Val Thr Gly Leu Leu Ile Trp His Phe Trp
            35                  40                  45

Asn Leu Leu Arg Leu Ser Trp Trp Leu Trp Val Asp Arg Ser Met Thr
50                  55                  60

Pro Pro Pro Gly Arg Gly Ser Trp Glu Pro Leu Leu Tyr Gly Leu His
65                  70                  75                  80

Gln Met Gln Leu Arg Asn Lys Lys Arg Arg Glu Leu Gly Asn Leu
                85                  90                  95

Ile Lys Arg Phe Arg Ser Gly Ala Glu Ser Leu Pro Asp Ala Val Val
                100                 105                 110

Leu Thr Thr Glu Glu Gly Gly Ile Phe Trp Cys Asn Gly Leu Ala Gln
            115                 120                 125

Gln Ile Leu Gly Leu Arg Trp Pro Glu Asp Asn Gly Gln Asn Ile Leu
        130                 135                 140

Asn Leu Leu Arg Tyr Pro Glu Phe Thr Gln Tyr Leu Lys Thr Arg Asp
145                 150                 155                 160

Phe Ser Arg Pro Leu Asn Leu Val Leu Asn Thr Gly Arg His Leu Glu
                165                 170                 175

Ile Arg Val Met Pro Tyr Thr His Lys Gln Leu Leu Met Val Ala Arg
            180                 185                 190

Asp Val Thr Gln Met His Gln Leu Glu Gly Ala Arg Arg Asn Phe Phe
        195                 200                 205

Ala Asn Val Ser His Glu Leu Arg Thr Pro Leu Thr Val Leu Gln Gly
    210                 215                 220

Tyr Leu Glu Met Met Asn Glu Gln Pro Leu Glu Gly Ala Val Arg Glu
225                 230                 235                 240

Lys Ala Leu His Thr Met Arg Glu Gln Thr Gln Arg Met Glu Gly Leu
                245                 250                 255

Val Lys Gln Leu Leu Thr Leu Ser Lys Ile Glu Ala Ala Pro Thr His
            260                 265                 270

Leu Leu Asn Glu Lys Val Asp Val Pro Met Met Leu Arg Val Val Glu
        275                 280                 285

Arg Glu Ala Gln Thr Leu Ser Gln Lys Gln Thr Phe Thr Phe Glu
    290                 295                 300

Ile Asp Asn Gly Leu Lys Val Ser Gly Asn Glu Asp Gln Leu Arg Ser
305                 310                 315                 320
```

```
Ala Ile Ser Asn Leu Val Tyr Asn Ala Val Asn His Thr Pro Glu Gly
            325                 330                 335

Thr His Ile Thr Val Arg Trp Gln Arg Val Pro His Gly Ala Glu Phe
        340                 345                 350

Ser Val Glu Asp Asn Gly Pro Gly Ile Ala Pro Glu His Ile Pro Arg
            355                 360                 365

Leu Thr Glu Arg Phe Tyr Arg Val Asp Lys Ala Arg Ser Arg Gln Thr
        370                 375                 380

Gly Gly Ser Gly Leu Gly Leu Ala Ile Val Lys His Ala Val Asn His
385                 390                 395                 400

His Glu Ser Arg Leu Asn Ile Glu Ser Thr Val Gly Lys Gly Thr Arg
            405                 410                 415

Phe Ser Phe Val Ile Pro Glu Arg Leu Ile Ala Lys Asn Ser Asp
        420                 425                 430

<210> SEQ ID NO 27
<211> LENGTH: 1641
<212> TYPE: DNA
<213> ORGANISM: E. coli

<400> SEQUENCE: 27
atgaatacaa ctccctcaca gcgattaggt tttttgcatc acatcaggtt ggttccgtta      60
tttgcctgca ttctaggcgg tatcttagtt ctattcgcat taagttcagc cctggctggc    120
tatttcctct ggcaggccga tcgcgatcag cgtgatgtta ctgcggagat tgagattcgg    180
accgggttag cgaacagttc agatttttg cgttcagccc ggatcaatat gattcaggcc    240
ggggctgcga gtcgtattgc ggaaatggaa gcaatgaagc gaaatattgc gcaagccgaa    300
tcggagatta acagtcgca gcaaggttat cgtgcttatc agaatcgacc ggtgaaaaca    360
cctgctgatg aagccctcga cactgaatta aatcaacgct tcaggctta tcacgggt      420 atgcaaccta tgttgaaata tgccaaaaat ggcatgtttg aagcgattat caatcatgaa    480
agtgagcaga tccgaccgct ggataatgct tataccgata ttttgaacaa agccgttaag    540
atacgtagca ccagagccaa ccaactggcg gaactggccc atcagcgcac ccgcctgggt    600
gggatgttca tgattggcgc gtttgtgctt gccctggtca tgacgctgat aacatttatg    660
gtgctacgtc ggatcgtcat tcgtccactg caacatgccg cacaacggat tgaaaaaatc    720
gccagtggcg atctgacgat gaatgatgaa ccggcgggtc gtaatgaaat cggtcgctta    780
agtcgtcatt tacagcaaat gcagcattca ctggggatga cagtagggac tgttcgacag    840
ggcgcggaag agatttatcg tggcaccagc gaaatttcag ctggcaatgc ggacctgtca    900
tctcgcaccg aagaacaagc ggcggctatc gaacaaactg ccgcagcat ggagcaactc     960 actgcgacgg tgaaacagaa tgcggataac gcgcatcatg ccagcaaact ggcgcaagag   1020
gcttctatta aagccagcga tggcgggcag acggtttccg gtgtagtaaa aacgatgggc   1080
gctatctcca cgagttcgaa gaaaatttct gagatcaccg ccgtcatcaa cagtattgct   1140
ttccagacga atattctggc actgaatgct gccgttgaag ccgcgcgagc gggtgagcaa   1200
gggcgtggat tgccgttgt cgccagcgaa gtacggacac tcgcaagtcg cagcgctcag   1260
gcggcgaaag agattgaagg cttgatcagt gaatcagtca ggttaattga cctggggtcg   1320
gatgaggtgg caacggccgg gaaaaccatg agcactattg ttgatgccgt cgcgagtgtc   1380
acacatatca tgcaggaaat cgccgccgcc tcggatgaac aaagtagagg cataacgcag   1440
gttagccagg cgatttctga aatggataag gtgacgcaac agaatgcttc tctggtagaa   1500
```

```
gaggcctcag cggcggcggt gtcccttgaa gaacaggcgg cacgattaac tgaggcggtg   1560
gatgtattcc gtctgcacaa acattctgtg tcggcagaac ctcgcggagc gggtgaacca   1620
gttagtttcg ctacggtgtg a                                             1641
```

<210> SEQ ID NO 28
<211> LENGTH: 546
<212> TYPE: PRT
<213> ORGANISM: E. coli

<400> SEQUENCE: 28

```
Met Asn Thr Thr Pro Ser Gln Arg Leu Gly Phe Leu His His Ile Arg
1               5                   10                  15

Leu Val Pro Leu Phe Ala Cys Ile Leu Gly Gly Ile Leu Val Leu Phe
            20                  25                  30

Ala Leu Ser Ser Ala Leu Ala Gly Tyr Phe Leu Trp Gln Ala Asp Arg
        35                  40                  45

Asp Gln Arg Asp Val Thr Ala Glu Ile Glu Ile Arg Thr Gly Leu Ala
    50                  55                  60

Asn Ser Ser Asp Phe Leu Arg Ser Ala Arg Ile Asn Met Ile Gln Ala
65                  70                  75                  80

Gly Ala Ala Ser Arg Ile Ala Glu Met Glu Ala Met Lys Arg Asn Ile
                85                  90                  95

Ala Gln Ala Glu Ser Glu Ile Lys Gln Ser Gln Gln Gly Tyr Arg Ala
            100                 105                 110

Tyr Gln Asn Arg Pro Val Lys Thr Pro Ala Asp Glu Ala Leu Asp Thr
        115                 120                 125

Glu Leu Asn Gln Arg Phe Gln Ala Tyr Ile Thr Gly Met Gln Pro Met
    130                 135                 140

Leu Lys Tyr Ala Lys Asn Gly Met Phe Glu Ala Ile Ile Asn His Glu
145                 150                 155                 160

Ser Glu Gln Ile Arg Pro Leu Asp Asn Ala Tyr Thr Asp Ile Leu Asn
                165                 170                 175

Lys Ala Val Lys Ile Arg Ser Thr Arg Ala Asn Gln Leu Ala Glu Leu
            180                 185                 190

Ala His Gln Arg Thr Arg Leu Gly Gly Met Phe Met Ile Gly Ala Phe
        195                 200                 205

Val Leu Ala Leu Val Met Thr Leu Ile Thr Phe Met Val Leu Arg Arg
    210                 215                 220

Ile Val Ile Arg Pro Leu Gln His Ala Ala Gln Arg Ile Glu Lys Ile
225                 230                 235                 240

Ala Ser Gly Asp Leu Thr Met Asn Asp Glu Pro Ala Gly Arg Asn Glu
                245                 250                 255

Ile Gly Arg Leu Ser Arg His Leu Gln Met Gln His Ser Leu Gly
            260                 265                 270

Met Thr Val Gly Thr Val Arg Gln Gly Ala Glu Glu Ile Tyr Arg Gly
        275                 280                 285

Thr Ser Glu Ile Ser Ala Gly Asn Ala Asp Leu Ser Ser Arg Thr Glu
    290                 295                 300

Glu Gln Ala Ala Ala Ile Glu Gln Thr Ala Ala Ser Met Glu Gln Leu
305                 310                 315                 320

Thr Ala Thr Val Lys Gln Asn Ala Asp Asn Ala His His Ala Ser Lys
                325                 330                 335

Leu Ala Gln Glu Ala Ser Ile Lys Ala Ser Asp Gly Gly Gln Thr Val
            340                 345                 350
```

```
Ser Gly Val Val Lys Thr Met Gly Ala Ile Ser Ser Lys Lys
        355                 360                 365
Ile Ser Glu Ile Thr Ala Val Ile Asn Ser Ile Ala Phe Gln Thr Asn
    370                 375                 380
Ile Leu Ala Leu Asn Ala Ala Val Glu Ala Ala Arg Ala Gly Glu Gln
385                 390                 395                 400
Gly Arg Gly Phe Ala Val Val Ala Ser Glu Val Arg Thr Leu Ala Ser
                405                 410                 415
Arg Ser Ala Gln Ala Ala Lys Glu Ile Glu Gly Leu Ile Ser Glu Ser
            420                 425                 430
Val Arg Leu Ile Asp Leu Gly Ser Asp Glu Val Ala Thr Ala Gly Lys
        435                 440                 445
Thr Met Ser Thr Ile Val Asp Ala Val Ala Ser Val Thr His Ile Met
    450                 455                 460
Gln Glu Ile Ala Ala Ala Ser Asp Glu Gln Ser Arg Gly Ile Thr Gln
465                 470                 475                 480
Val Ser Gln Ala Ile Ser Glu Met Asp Lys Val Thr Gln Gln Asn Ala
                485                 490                 495
Ser Leu Val Glu Glu Ala Ser Ala Ala Val Ser Leu Glu Glu Gln
            500                 505                 510
Ala Ala Arg Leu Thr Glu Ala Val Asp Val Phe Arg Leu His Lys His
        515                 520                 525
Ser Val Ser Ala Glu Pro Arg Gly Ala Gly Glu Pro Val Ser Phe Ala
    530                 535                 540
Thr Val
545

<210> SEQ ID NO 29
<211> LENGTH: 1662
<212> TYPE: DNA
<213> ORGANISM: E. coli

<400> SEQUENCE: 29
atgattaacc gtatccgcgt agtcacgctg ttggtaatgg tgctgggggt attcgcactg      60
ttacagctta tttccggcag tctgtttttt tcttcccttc accatagcca aagagctt     120 gtggtttcca atcaattacg ggaacagcag ggcgagctga cgtcaacctg ggatttaatg    180
ctgcaaacgc gcattaacct gagtcgttca gcggtacgga tgatgatgga ttcctccaat    240
caacaaagta acgccaaagt tgaattgctc gatagcgcca ggaaaacatt ggcgcaggca    300
gcgacgcatt ataaaaaatt caaaagcatg gcaccgttac ctgaaatggt cgctaccagt    360
cgtaatattg atgaaaaata taaaaactat tacacagcgt taactgaact gattgattat    420
ctagattatg caatactgg agcttatttc gctcagccaa cccagggaat gcaaaatgca    480
atgggcgaag cgtttgctca gtacgccctc agcagtgaaa aactgtatcg cgatatcgtc    540
actgacaacg cagatgatta ccgatttgcc cagtggcaac tggcggttat cgcgctggtg    600
gtggtattga ttctgctggt ggcgtggtac ggcattcgcc gtatgttgct tactccgctg    660
gcaaaaatta ttgctcacat tcgcgaaatc gccggtggta acctggcgaa taccctgacc    720
attgacgggc gcagtgaaat gggcgacctg gcgcagagcg tttcacatat gcaacgctct    780
ttgactgaca ccgtcactca tgtccgcgaa ggttcagatg ccatctatgc cggtacccgt    840
gaaattgcgg cggcaacac cgatctttcc tcccgtactg aacagcaggc atccgcgctg    900
gaagaaactg ccgccagcat ggagcagctc accgcgacag tgaagcaaaa cgccgataac    960
```

```
gcccgccagg cctcgcaact ggcgcaaagt gcctccgaca ccgcccagca cggcggcaaa    1020
gtggtggatg cgtagtgaa acgatgcat gagatcgccg atagttcgaa gaaaattgcc       1080
gacattatca gcgttatcga cggtattgcc ttccagacta atatcctcgc gctgaatgcc     1140
gcggttgaag ccgcgcgtgc gggtgaacag ggccgtggtt ttgccgtggt ggcgggtgaa     1200
gtgcgtaatc ttgccagtcg cagcgcccag gcggcaaaag agatcaaagc cctcattgaa     1260
gactccgtct cacgcgttga taccggttcg gtgctggtcg aaagcgccgg ggaaacaatg     1320
aacaatatcg tcaatgctgt cactcgcgtg actgacatta tgggcgagat tgcatcggca     1380
tcggatgaac agagccgtgg catcgatcaa gtcgcattgg cggtttcgga atggatcgc      1440 gtcacgcaac agaacgcatc gctggtgcag gaatcagctg ccgccgccgc tgcgctggaa     1500
gaacaggcga tcgtttaac gcaagcagtt tccgcgttcc gtctggcagc cagcccactc      1560
accaataaac cgcaaacacc atcccgtcct gccagtgagc aaccaccggc tcagccacga     1620
ctgcgaattg ctgaacaaga tccaaactgg gaaacatttt ga                        1662
```

<210> SEQ ID NO 30
<211> LENGTH: 553
<212> TYPE: PRT
<213> ORGANISM: E. coli

<400> SEQUENCE: 30

```
Met Ile Asn Arg Ile Arg Val Val Thr Leu Leu Val Met Val Leu Gly
1               5                   10                  15

Val Phe Ala Leu Leu Gln Leu Ile Ser Gly Ser Leu Phe Phe Ser Ser
            20                  25                  30

Leu His His Ser Gln Lys Ser Phe Val Val Ser Asn Gln Leu Arg Glu
        35                  40                  45

Gln Gln Gly Glu Leu Thr Ser Thr Trp Asp Leu Met Leu Gln Thr Arg
    50                  55                  60

Ile Asn Leu Ser Arg Ser Ala Val Arg Met Met Met Asp Ser Ser Asn
65                  70                  75                  80

Gln Gln Ser Asn Ala Lys Val Glu Leu Leu Asp Ser Ala Arg Lys Thr
                85                  90                  95

Leu Ala Gln Ala Ala Thr His Tyr Lys Lys Phe Lys Ser Met Ala Pro
            100                 105                 110

Leu Pro Glu Met Val Ala Thr Ser Arg Asn Ile Asp Glu Lys Tyr Lys
        115                 120                 125

Asn Tyr Tyr Thr Ala Leu Thr Glu Leu Ile Asp Tyr Leu Asp Tyr Gly
    130                 135                 140

Asn Thr Gly Ala Tyr Phe Ala Gln Pro Thr Gln Gly Met Gln Asn Ala
145                 150                 155                 160

Met Gly Glu Ala Phe Ala Gln Tyr Ala Leu Ser Ser Glu Lys Leu Tyr
                165                 170                 175

Arg Asp Ile Val Thr Asp Asn Ala Asp Asp Tyr Arg Phe Ala Gln Trp
            180                 185                 190

Gln Leu Ala Val Ile Ala Leu Val Val Val Leu Ile Leu Leu Val Ala
        195                 200                 205

Trp Tyr Gly Ile Arg Arg Met Leu Leu Thr Pro Leu Ala Lys Ile Ile
    210                 215                 220

Ala His Ile Arg Glu Ile Ala Gly Gly Asn Leu Ala Asn Thr Leu Thr
225                 230                 235                 240

Ile Asp Gly Arg Ser Glu Met Gly Asp Leu Ala Gln Ser Val Ser His
```

|  |  |  |  | 245 |  |  |  |  | 250 |  |  |  |  | 255 |  |
|---|---|---|---|---|---|---|---|---|---|---|---|---|---|---|---|

Met Gln Arg Ser Leu Thr Asp Thr Val Thr His Val Arg Glu Gly Ser
                     260                 265                 270

Asp Ala Ile Tyr Ala Gly Thr Arg Glu Ile Ala Ala Gly Asn Thr Asp
            275                 280                 285

Leu Ser Ser Arg Thr Glu Gln Gln Ala Ser Ala Leu Glu Glu Thr Ala
290                 295                 300

Ala Ser Met Glu Gln Leu Thr Ala Thr Val Lys Gln Asn Ala Asp Asn
305                 310                 315                 320

Ala Arg Gln Ala Ser Gln Leu Ala Gln Ser Ala Ser Asp Thr Ala Gln
                325                 330                 335

His Gly Gly Lys Val Asp Gly Val Val Lys Thr Met His Glu Ile
            340                 345                 350

Ala Asp Ser Ser Lys Lys Ile Ala Asp Ile Ile Ser Val Ile Asp Gly
            355                 360                 365

Ile Ala Phe Gln Thr Asn Ile Leu Ala Leu Asn Ala Ala Val Glu Ala
            370                 375                 380

Ala Arg Ala Gly Glu Gln Gly Arg Gly Phe Ala Val Val Ala Gly Glu
385                 390                 395                 400

Val Arg Asn Leu Ala Ser Arg Ser Ala Gln Ala Ala Lys Glu Ile Lys
                405                 410                 415

Ala Leu Ile Glu Asp Ser Val Ser Arg Val Asp Thr Gly Ser Val Leu
            420                 425                 430

Val Glu Ser Ala Gly Glu Thr Met Asn Asn Ile Val Asn Ala Val Thr
            435                 440                 445

Arg Val Thr Asp Ile Met Gly Glu Ile Ala Ser Ala Ser Asp Glu Gln
            450                 455                 460

Ser Arg Gly Ile Asp Gln Val Ala Leu Ala Val Ser Glu Met Asp Arg
465                 470                 475                 480

Val Thr Gln Gln Asn Ala Ser Leu Val Gln Glu Ser Ala Ala Ala Ala
                485                 490                 495

Ala Ala Leu Glu Glu Gln Ala Ser Arg Leu Thr Gln Ala Val Ser Ala
            500                 505                 510

Phe Arg Leu Ala Ala Ser Pro Leu Thr Asn Lys Pro Gln Thr Pro Ser
            515                 520                 525

Arg Pro Ala Ser Glu Gln Pro Ala Gln Pro Arg Leu Arg Ile Ala
            530                 535                 540

Glu Gln Asp Pro Asn Trp Glu Thr Phe
545                 550

<210> SEQ ID NO 31
<211> LENGTH: 1353
<212> TYPE: DNA
<213> ORGANISM: E. coli

<400> SEQUENCE: 31

```
atgaggcgat tgcgcttctc gccacgaagt tcatttgccc gtacgttatt gctcatcgtc      60
accttgctgt tcgccagcct ggtgacgact tatctggtgg tgctgaactt cgcgattttg     120
ccgagcctcc agcagtttaa taaagtcctc gcgtacgaag tgcgtatgtt gatgaccgac     180
aaactgcaac tggaggacgg cacgcagttg gttgtgcctc ccgctttccg tcgggagatc     240
taccgtgagc tggggatctc tctctactcc aacgaggctg ccgaagaggc aggtctgcgt     300
tgggcgcaac actatgaatt cttaagccat cagatggcgc agcaactggg cggcccgacg     360
```

```
gaagtgcgcg ttgaggtcaa caaaagttcg cctgtcgtct ggctgaaaac ctggctgtcg    420
cccaatatct gggtacgcgt gccgctgacc gaaattcatc agggcgattt ctctccgctg    480
ttccgctata cgctggcgat tatgctattg gcgataggcg gggcgtggct gtttattcgt    540
atccagaacc gaccgttggt cgatctcgaa cacgcagcct tgcaggttgg taaagggatt    600
attccgccgc cgctgcgtga gtatggcgct tcggaggtgc gttccgttac ccgtgccttt    660
aaccatatgg cggctggtgt taagcaactg gcggatgacc gcacgctgct gatgcgggg     720 gtaagtcacg acttgcgcac gccgctgacg cgtattcgcc tggcgactga gatgatgagc    780
gagcaggatg gctatctggc agaatcgatc aataaagata tcgaagagtg caacgccatc    840
attgagcagt ttatcgacta cctgcgcacc gggcaggaga tgccgatgga aatggcggat    900
cttaatgcag tactcggtga ggtgattgct gccgaaagtg gctatgagcg ggaaattgaa    960
accgcgcttt accccggcag cattgaagtg aaaatgcacc cgctgtcgat caaacgcgcg   1020
gtggcgaata tggtggtcaa cgccgcccgt tatggcaatg gctggatcaa agtcagcagc   1080
ggaacggagc cgaatcgcgc ctggttccag gtggaagatg acggtccggg aattgcgccg   1140
gaacaacgta agcacctgtt ccagccgttt gtccgcggcg acagtgcgcg caccattagc   1200
ggcacgggat tagggctggc aattgtgcag cgtatcgtgg ataaccataa cgggatgctg   1260
gagcttggca ccagcgagcg gggcgggctt tccattcgcg cctggctgcc agtgccggta   1320
acgcgggcgc agggcacgac aaaagaaggg taa                                 1353
```

<210> SEQ ID NO 32
<211> LENGTH: 450
<212> TYPE: PRT
<213> ORGANISM: E. coli

<400> SEQUENCE: 32

```
Met Arg Arg Leu Arg Phe Ser Pro Arg Ser Phe Ala Arg Thr Leu
1               5                   10                  15

Leu Leu Ile Val Thr Leu Leu Phe Ala Ser Leu Val Thr Thr Tyr Leu
            20                  25                  30

Val Val Leu Asn Phe Ala Ile Leu Pro Ser Leu Gln Gln Phe Asn Lys
        35                  40                  45

Val Leu Ala Tyr Glu Val Arg Met Leu Met Thr Asp Lys Leu Gln Leu
    50                  55                  60

Glu Asp Gly Thr Gln Leu Val Val Pro Ala Phe Arg Arg Glu Ile
65                  70                  75                  80

Tyr Arg Glu Leu Gly Ile Ser Leu Tyr Ser Asn Glu Ala Ala Glu Glu
                85                  90                  95

Ala Gly Leu Arg Trp Ala Gln His Tyr Glu Phe Leu Ser His Gln Met
            100                 105                 110

Ala Gln Gln Leu Gly Gly Pro Thr Glu Val Arg Val Glu Val Asn Lys
        115                 120                 125

Ser Ser Pro Val Val Trp Leu Lys Thr Trp Leu Ser Pro Asn Ile Trp
    130                 135                 140

Val Arg Val Pro Leu Thr Glu Ile His Gln Gly Asp Phe Ser Pro Leu
145                 150                 155                 160

Phe Arg Tyr Thr Leu Ala Ile Met Leu Leu Ala Ile Gly Gly Ala Trp
                165                 170                 175

Leu Phe Ile Arg Ile Gln Asn Arg Pro Leu Val Asp Leu Glu His Ala
            180                 185                 190

Ala Leu Gln Val Gly Lys Gly Ile Ile Pro Pro Leu Arg Glu Tyr
```

```
                    195                 200                 205
Gly Ala Ser Glu Val Arg Ser Val Thr Arg Ala Phe Asn His Met Ala
    210                 215                 220
Ala Gly Val Lys Gln Leu Ala Asp Asp Arg Thr Leu Leu Met Ala Gly
225                 230                 235                 240
Val Ser His Asp Leu Arg Thr Pro Leu Thr Arg Ile Arg Leu Ala Thr
                245                 250                 255
Glu Met Met Ser Glu Gln Asp Gly Tyr Leu Ala Glu Ser Ile Asn Lys
            260                 265                 270
Asp Ile Glu Glu Cys Asn Ala Ile Ile Glu Gln Phe Ile Asp Tyr Leu
        275                 280                 285
Arg Thr Gly Gln Glu Met Pro Met Glu Met Ala Asp Leu Asn Ala Val
    290                 295                 300
Leu Gly Glu Val Ile Ala Ala Glu Ser Gly Tyr Glu Arg Glu Ile Glu
305                 310                 315                 320
Thr Ala Leu Tyr Pro Gly Ser Ile Glu Val Lys Met His Pro Leu Ser
                325                 330                 335
Ile Lys Arg Ala Val Ala Asn Met Val Val Asn Ala Ala Arg Tyr Gly
            340                 345                 350
Asn Gly Trp Ile Lys Val Ser Ser Gly Thr Glu Pro Asn Arg Ala Trp
        355                 360                 365
Phe Gln Val Glu Asp Asp Gly Pro Gly Ile Ala Pro Glu Gln Arg Lys
    370                 375                 380
His Leu Phe Gln Pro Phe Val Arg Gly Asp Ser Ala Arg Thr Ile Ser
385                 390                 395                 400
Gly Thr Gly Leu Gly Leu Ala Ile Val Gln Arg Ile Val Asp Asn His
                405                 410                 415
Asn Gly Met Leu Glu Leu Gly Thr Ser Glu Arg Gly Leu Ser Ile
            420                 425                 430
Arg Ala Trp Leu Pro Val Pro Val Thr Arg Ala Gln Gly Thr Thr Lys
        435                 440                 445
Glu Gly
    450

<210> SEQ ID NO 33
<211> LENGTH: 2154
<212> TYPE: DNA
<213> ORGANISM: Xylella fastidiosa

<400> SEQUENCE: 33
atgctaaaga aagctaaatg gatatgcagt cggctatcgc agcggccaga tagtgagcat      60
gtacaaaatt taatcagatt tcttatcgcc tcgctcttca tcatctactt gagcgtatgt     120
tggcatggcg aaacggatct caatacatcg cgggtcatct ggttggtgtt gctgtccgat     180
cttggcgtgt cgctggcgct gatgcttgcg attgtcatgc atccgcagat ctcgcacgtg     240
cggcgttgta ttggcatcat tgccgactac acatcactga cggtgctgat gttgctgatg     300
ggcgaggcgg gttcaccgct gtatgtccta tgtttgtggg taaccatcgg taatggctta     360
cgttatggca gtgtgtattt gctggttact acgacccttg gtgcgttgag tttcctgacg     420
gtgatcctcg tttcagcgta ctggaagtcg aatccgtttc tggcttgggg attactgatt     480
ggtctgattg ccatcccttg gtatttccag tctctgttga aggcattgat ccaagccctt     540
aacgatgcac gtcatgctaa tgaggctaag agtcgcttct ggctaatat gagccatgaa     600 tttcgcacgc cgctgaatgg tttgtcgggt atgacggagg tgttggccac aacgcgtttg     660
```

```
gatgccgagc aaagggaatg cttgaaagcg atccaggcat cggtacacag cgtgttgtcc      720
ttgattgagg aagtgctcga catctcaaga attgaggcag gtaagatccg tatcctccac      780
gatactttct ccttgaagga ggtgattggc agtgtcggtc tgatcctgca accacagatc      840
cgcaataaag ccttggaata tcgtgtcgat gtggggttgg atgttcccga atggttgttc      900
ggcgatgctg gctatgtgcg tcaggtctta ttgaacattg tcggtaatgc ggtcaagttt      960
accgagcgtg gtcggattac attgtgtgtc agcgtgttga accgttctag acagcacagt     1020
gtggtgttgc gttttgaagt tgcagatact ggcattggtg tgccattggg aatgcggaat     1080
cggcttttcg acgtgttcga gcaggctgat gttggtttgg atcgccgtta tcaaggaagc     1140
ggactgggta ccacgattgc caagggttta attgaattga tgggtggaag catcgggttt     1200
gaggagaacg tcccttgtgg gagcttgttt tggttcgaat tgccgtttga acttgccaag     1260
gaacaggtgg ttgcgcaaga ggtatccgaa gcatcgcagt gtaccgaacc gagtaacgtt     1320
atcgcatttt ccaatccatt cctacggcat cgtgctcgtg tcaagagcat gcgcgtgctg     1380
gttgctgatg accatgaaac taaccgcatg gtgttatcca gaatccttga taaggcggga     1440
cacaagctgt tatgcgtgga tggtgcggaa gcagtgttgg attgttttgat cagtatggaa     1500 ttcgatgttg tgatcatcga cctgcacatg cctggaatga gcggtttgga catgctcaaa     1560
cagttgcggg tcatgcaaag ttccagtctg ccttatacac cggtgcttgt gctgagtgcc     1620
gatgcgacgt ccgattcgat ccgctgttgt gaagaggcag gagcgcgtgc ttttctgtcc     1680
aaacccgtgc ttgctactaa attgctggat gtacttgccg aaattgctga agggatggt      1740 ggtgcattac cttacgctgc attatcgcaa tcctcagttc agcagcatca ggtgttcgat     1800
ccggcgggtt tggatgatct ggctgagttg aatatggacg atgatttcga agagcggttc     1860
atagttcagt cttttcgaga tgccgaacac tgccagcaga caatgttgtc tgccgctgaa     1920
accaaccagt ggcaggaggt gcgggaagaa gcgcatgcac tgcgtggtgt gcttggtcat     1980 cttggttaa tgcgcgcttc gtcgctggcg gcagagttga tgcgtatccc agattggcag     2040
ttgcaattgg agtggtgtgc tcttgtccaa atgctggatg aagcactgct gtgtggtcgt     2100
gatgcgcttg aagcgcgccg acaggaacgc cggcgcagtg gggttttacg atga           2154
```

<210> SEQ ID NO 34
<211> LENGTH: 717
<212> TYPE: PRT
<213> ORGANISM: Xylella fastidiosa

<400> SEQUENCE: 34

Met Leu Lys Lys Ala Lys Trp Ile Cys Ser Arg Leu Ser Gln Arg Pro
1               5                   10                  15

Asp Ser Glu His Val Gln Asn Leu Ile Arg Phe Leu Ile Ala Ser Leu
            20                  25                  30

Phe Ile Ile Tyr Leu Ser Val Cys Trp His Gly Glu Thr Asp Leu Asn
        35                  40                  45

Thr Ser Arg Val Ile Trp Leu Val Leu Ser Asp Leu Gly Val Ser
    50                  55                  60

Leu Ala Leu Met Leu Ala Ile Val Met His Pro Gln Ile Ser His Val
65                  70                  75                  80

Arg Arg Cys Ile Gly Ile Ile Ala Asp Tyr Thr Ser Leu Thr Val Leu
                85                  90                  95

Met Leu Leu Met Gly Glu Ala Gly Ser Pro Leu Tyr Val Leu Cys Leu
            100                 105                 110

```
Trp Val Thr Ile Gly Asn Gly Leu Arg Tyr Gly Ser Val Tyr Leu Leu
            115                 120                 125

Val Thr Thr Thr Leu Gly Ala Leu Ser Phe Leu Thr Val Ile Leu Val
        130                 135                 140

Ser Ala Tyr Trp Lys Ser Asn Pro Phe Leu Ala Trp Gly Leu Leu Ile
145                 150                 155                 160

Gly Leu Ile Ala Ile Pro Trp Tyr Phe Gln Ser Leu Leu Lys Ala Leu
                165                 170                 175

Ile Gln Ala Leu Asn Asp Ala Arg His Ala Asn Glu Ala Lys Ser Arg
                180                 185                 190

Phe Leu Ala Asn Met Ser His Glu Phe Arg Thr Pro Leu Asn Gly Leu
            195                 200                 205

Ser Gly Met Thr Glu Val Leu Ala Thr Thr Arg Leu Asp Ala Glu Gln
        210                 215                 220

Arg Glu Cys Leu Lys Ala Ile Gln Ala Ser Val His Ser Val Leu Ser
225                 230                 235                 240

Leu Ile Glu Glu Val Leu Asp Ile Ser Arg Ile Glu Ala Gly Lys Ile
                245                 250                 255

Arg Ile Leu His Asp Thr Phe Ser Leu Lys Glu Val Ile Gly Ser Val
            260                 265                 270

Gly Leu Ile Leu Gln Pro Gln Ile Arg Asn Lys Ala Leu Glu Tyr Arg
        275                 280                 285

Val Asp Val Gly Leu Asp Val Pro Glu Trp Leu Phe Gly Asp Ala Gly
290                 295                 300

Tyr Val Arg Gln Val Leu Leu Asn Ile Val Gly Asn Ala Val Lys Phe
305                 310                 315                 320

Thr Glu Arg Gly Arg Ile Thr Leu Cys Val Ser Val Leu Asn Arg Ser
                325                 330                 335

Arg Gln His Ser Val Val Leu Arg Phe Glu Val Ala Asp Thr Gly Ile
            340                 345                 350

Gly Val Pro Leu Gly Met Arg Asn Arg Leu Phe Asp Val Phe Glu Gln
        355                 360                 365

Ala Asp Val Gly Leu Asp Arg Arg Tyr Gln Gly Ser Gly Leu Gly Thr
370                 375                 380

Thr Ile Ala Lys Gly Leu Ile Glu Leu Met Gly Gly Ser Ile Gly Phe
385                 390                 395                 400

Glu Glu Asn Val Pro Cys Gly Ser Leu Phe Trp Phe Glu Leu Pro Phe
                405                 410                 415

Glu Leu Ala Lys Glu Gln Val Val Ala Gln Glu Val Ser Glu Ala Ser
            420                 425                 430

Gln Cys Thr Glu Pro Ser Asn Val Ile Ala Phe Ser Asn Pro Phe Leu
        435                 440                 445

Arg His Arg Ala Arg Val Lys Ser Met Arg Val Leu Val Ala Asp Asp
450                 455                 460

His Glu Thr Asn Arg Met Val Leu Ser Arg Ile Leu Asp Lys Ala Gly
465                 470                 475                 480

His Lys Leu Leu Cys Val Asp Gly Ala Glu Ala Val Leu Asp Cys Leu
                485                 490                 495

Ile Ser Met Glu Phe Asp Val Val Ile Ile Asp Leu His Met Pro Gly
            500                 505                 510

Met Ser Gly Leu Asp Met Leu Lys Gln Leu Arg Val Met Gln Ser Ser
        515                 520                 525
```

| | | | |
|---|---|---|---|
| Ser | Leu Pro Tyr Thr Pro Val Leu Val Leu Ser Ala Asp Ala Thr Ser | | |
| 530 | 535 | 540 | |

Asp Ser Ile Arg Cys Cys Glu Glu Ala Gly Ala Arg Ala Phe Leu Ser
545                 550                 555                 560

Lys Pro Val Leu Ala Thr Lys Leu Leu Asp Val Leu Ala Glu Ile Ala
            565                 570                 575

Glu Gly Asp Gly Gly Ala Leu Pro Tyr Ala Ala Leu Ser Gln Ser Ser
            580                 585                 590

Val Gln Gln His Gln Val Phe Asp Pro Ala Gly Leu Asp Leu Ala
        595                 600                 605

Glu Leu Asn Met Asp Asp Phe Glu Glu Arg Phe Ile Val Gln Ser
    610                 615                 620

Phe Arg Asp Ala Glu His Cys Gln Gln Thr Met Leu Ser Ala Ala Glu
625                 630                 635                 640

Thr Asn Gln Trp Gln Glu Val Arg Glu Ala His Ala Leu Arg Gly
            645                 650                 655

Val Leu Gly His Leu Gly Leu Met Arg Ala Ser Ser Leu Ala Ala Glu
            660                 665                 670

Leu Met Arg Ile Pro Asp Trp Gln Leu Gln Leu Glu Trp Cys Ala Leu
            675                 680                 685

Val Gln Met Leu Asp Glu Ala Leu Leu Cys Gly Arg Asp Ala Leu Glu
        690                 695                 700

Ala Arg Arg Gln Glu Arg Arg Ser Gly Val Leu Arg
705                 710                 715

<210> SEQ ID NO 35
<211> LENGTH: 1485
<212> TYPE: DNA
<213> ORGANISM: Artificial Sequence
<220> FEATURE:
<223> OTHER INFORMATION: Fusion protein coding sequence

<400> SEQUENCE: 35

```
atgaatacaa ctccctcaca gcgattaggt ttttgcatc acatcaggtt ggttccgtta      60
tttgcctgca ttctaggcgg tatcttagtt ctattcgcat taagttcagc cctggctggc    120
tatttcctct ggcaggccga tcgcgatcag cgtgatgtta ctgcggagat tgagattcgg    180
accgggttag cgaacagttc agattttttg cgttcagccc ggatcaatat gattcaggcc    240
ggggctgcga gtcgtattgc ggaaatggaa gcaatgaagc gaaatattgc gcaagccgaa    300
tcggagatta acagtcgca gcaaggttat cgtgcttatc agaatcgacc ggtgaaaaca    360
cctgctgatg aagccctcga cactgaatta aatcaacgct tcaggctta tcacgggt      420
atgcaaccta tgttgaaata tgccaaaaat ggcatgtttg aagcgattat caatcatgaa    480
agtgagcaga tccgaccgct ggataatgct tataccgata ttttgaacaa agccgttaag    540
atacgtagca ccagagccaa ccaactggcg gaactggccc atcagcgcac cgcctgggt    600
gggatgttca tgattggcgc gtttgtgctt gccctggtca tgacgctgat aacatttatg    660
gtgctacgtc ggatcgtcat tcgtccactg caacatgccg cacaacggat tgaaaaaatc    720
gccagtggcg atctgacgat gaatgatgaa ccggcgggtc gtaatgaaat cggtcgctta    780
agtcgtcatt tacagcatat ggcggctggt gttaagcaac tggcggatga ccgcacgctg    840
ctgatggcgg gggtaagtca cgacttgcgc acgccgctga cgcgtattcg cctggcgact    900
gagatgatga cgagcagga tggctatctg cagaatcga tcaataaaga tatcgaagag    960
tgcaacgcca tcattgagca gtttatcgac tacctgcgca ccgggcagga gatgccgatg   1020
```

```
gaaatggcgg atcttaatgc agtactcggt gaggtgattg ctgccgaaag tggctatgag    1080
cgggaaattg aaaccgcgct ttaccccggc agcattgaag tgaaaatgca cccgctgtcg    1140
atcaaacgcg cggtggcgaa tatggtggtc aacgccgccc gttatggcaa tggctggatc    1200
aaagtcagca gcggaacgga gccgaatcgc gcctggttcc aggtggaaga tgacggtccg    1260
ggaattgcgc cggaacaacg taagcacctg ttccagccgt ttgtccgcgg cgacagtgcg    1320
cgcaccatta gcgcacgggg attagggctg caattgtgc agcgtatcgt ggataaccat    1380
aacgggatgc tggagcttgg caccagcgag cggggcgggc tttccattcg cgcctggctg    1440
ccagtgccgg taacgcgggc gcagggcacg acaaaagaag ggtaa                    1485
```

<210> SEQ ID NO 36
<211> LENGTH: 494
<212> TYPE: PRT
<213> ORGANISM: Artificial Sequence
<220> FEATURE:
<223> OTHER INFORMATION: Fusion protein

<400> SEQUENCE: 36

```
Met Asn Thr Thr Pro Ser Gln Arg Leu Gly Phe Leu His His Ile Arg
1               5                   10                  15

Leu Val Pro Leu Phe Ala Cys Ile Leu Gly Gly Ile Leu Val Leu Phe
            20                  25                  30

Ala Leu Ser Ser Ala Leu Ala Gly Tyr Phe Leu Trp Gln Ala Asp Arg
        35                  40                  45

Asp Gln Arg Asp Val Thr Ala Glu Ile Glu Ile Arg Thr Gly Leu Ala
    50                  55                  60

Asn Ser Ser Asp Phe Leu Arg Ser Ala Arg Ile Asn Met Ile Gln Ala
65                  70                  75                  80

Gly Ala Ala Ser Arg Ile Ala Glu Met Glu Ala Met Lys Arg Asn Ile
                85                  90                  95

Ala Gln Ala Glu Ser Glu Ile Lys Gln Ser Gln Gly Tyr Arg Ala
            100                 105                 110

Tyr Gln Asn Arg Pro Val Lys Thr Pro Ala Asp Glu Ala Leu Asp Thr
        115                 120                 125

Glu Leu Asn Gln Arg Phe Gln Ala Tyr Ile Thr Gly Met Gln Pro Met
    130                 135                 140

Leu Lys Tyr Ala Lys Asn Gly Met Phe Glu Ala Ile Ile Asn His Glu
145                 150                 155                 160

Ser Glu Gln Ile Arg Pro Leu Asp Asn Ala Tyr Thr Asp Ile Leu Asn
                165                 170                 175

Lys Ala Val Lys Ile Arg Ser Thr Arg Ala Asn Gln Leu Ala Glu Leu
            180                 185                 190

Ala His Gln Arg Thr Arg Leu Gly Gly Met Phe Met Ile Gly Ala Phe
        195                 200                 205

Val Leu Ala Leu Val Met Thr Leu Ile Thr Phe Met Val Leu Arg Arg
    210                 215                 220

Ile Val Ile Arg Pro Leu Gln His Ala Ala Gln Arg Ile Glu Lys Ile
225                 230                 235                 240

Ala Ser Gly Asp Leu Thr Met Asn Asp Glu Pro Ala Gly Arg Asn Glu
                245                 250                 255

Ile Gly Arg Leu Ser Arg His Leu Gln His Met Ala Ala Gly Val Lys
            260                 265                 270

Gln Leu Ala Asp Asp Arg Thr Leu Leu Met Ala Gly Val Ser His Asp
```

```
              275                 280                 285
Leu Arg Thr Pro Leu Thr Arg Ile Arg Leu Ala Thr Glu Met Met Ser
        290                 295                 300
Glu Gln Asp Gly Tyr Leu Ala Glu Ser Ile Asn Lys Asp Ile Glu Glu
305                 310                 315                 320
Cys Asn Ala Ile Ile Glu Gln Phe Ile Asp Tyr Leu Arg Thr Gly Gln
                325                 330                 335
Glu Met Pro Met Glu Met Ala Asp Leu Asn Ala Val Leu Gly Glu Val
                340                 345                 350
Ile Ala Ala Glu Ser Gly Tyr Glu Arg Glu Ile Glu Thr Ala Leu Tyr
                355                 360                 365
Pro Gly Ser Ile Glu Val Lys Met His Pro Leu Ser Ile Lys Arg Ala
            370                 375                 380
Val Ala Asn Met Val Val Asn Ala Ala Arg Tyr Gly Asn Gly Trp Ile
385                 390                 395                 400
Lys Val Ser Ser Gly Thr Glu Pro Asn Arg Ala Trp Phe Gln Val Glu
                405                 410                 415
Asp Asp Gly Pro Gly Ile Ala Pro Glu Gln Arg Lys His Leu Phe Gln
                420                 425                 430
Pro Phe Val Arg Gly Asp Ser Ala Arg Thr Ile Ser Gly Thr Gly Leu
            435                 440                 445
Gly Leu Ala Ile Val Gln Arg Ile Val Asp Asn His Asn Gly Met Leu
450                 455                 460
Glu Leu Gly Thr Ser Glu Arg Gly Gly Leu Ser Ile Arg Ala Trp Leu
465                 470                 475                 480
Pro Val Pro Val Thr Arg Ala Gln Gly Thr Thr Lys Glu Gly
                485                 490
```

<210> SEQ ID NO 37
<211> LENGTH: 1455
<212> TYPE: DNA
<213> ORGANISM: Artificial Sequence
<220> FEATURE:
<223> OTHER INFORMATION: Fusion protein coding sequence

<400> SEQUENCE: 37

```
atgattaacc gtatccgcgt agtcacgctg ttggtaatgg tcctgggggt attcgcactg      60
ttacagctta tttccggcag tctgtttttt cttcccttc accatagcca gaagagcttt     120
gtggtttcca atcaattacg ggaacagcag ggcgagctga cgtcaacctg ggatttaatg     180
ctgcaaacgc gcattaacct gagtcgttca gcggtacgga tgatgatgga ttcctccaat     240
caacaaagta acgccaaagt tgaattgctc gatagcgcca ggaaaacatt ggcgcaggca     300
gcgacgcatt ataaaaaatt caaaagcatg caccgttac tgaaatggt cgctaccagt     360
cgtaatattg atgaaaaata taaaaactat tacacagcgt taactgaact gattgattat     420
ctagattatg caatactgg agcttatttc gctcagccaa cccagggaat gcaaaatgca     480
atgggcgaac ggtttgctca gtacgccctc agcagtgaaa aactgtatcg cgatatcgtc     540
actgacaacg cagatgatta ccgatttgcc cagtggcaac tggcggttat cgcgctggtg     600
gtggtattga ttctgctggt ggcgtggtac ggcattcgcc gtatgttgct tactccgctg     660
gcaaaaatta ttgctcacat tgcgaaatc gccggtggta acctggcgaa taccctgacc     720
attgacgggc gcagtgaaat gggcgacctg gcgcagagcg tttcacatat ggcggctggt     780
gttaagcaac tggcggatga ccgcacgctg ctgatggcgg gggtaagtca cgacttgcgc     840
```

```
acgccgctga cgcgtattcg cctggcgact gagatgatga gcgagcagga tggctatctg    900
gcagaatcga tcaataaaga tatcgaagag tgcaacgcca tcattgagca gtttatcgac    960
tacctgcgca ccgggcagga gatgccgatg gaaatggcgg atcttaatgc agtactcggt   1020
gaggtgattg ctgccgaaag tggctatgag cgggaaattg aaaccgcgct ttaccccggc   1080
agcattgaag tgaaaatgca cccgctgtcg atcaaacgcg cggtggcgaa tatggtggtc   1140
aacgccgccc gttatggcaa tggctggatc aaagtcagca gcggaacgga gccgaatcgc   1200
gcctggttcc aggtggaaga tgacggtccg ggaattgcgc cggaacaacg taagcacctg   1260
ttccagccgt ttgtccgcgg cgacagtgcg cgcaccatta gcggcacggg attagggctg   1320
gcaattgtgc agcgtatcgt ggataaccat aacgggatgc tggagcttgg caccagcgag   1380
cggggcgggc tttccattcg cgcctggctg ccagtgccgg taacgcgggc gcagggcacg   1440
acaaaagaag ggtaa                                                    1455
```

<210> SEQ ID NO 38
<211> LENGTH: 484
<212> TYPE: PRT
<213> ORGANISM: Artificial Sequence
<220> FEATURE:
<223> OTHER INFORMATION: Fusion protein

<400> SEQUENCE: 38

```
Met Ile Asn Arg Ile Arg Val Val Thr Leu Leu Val Met Val Leu Gly
1               5                  10                  15

Val Phe Ala Leu Leu Gln Leu Ile Ser Gly Ser Leu Phe Phe Ser Ser
            20                  25                  30

Leu His His Ser Gln Lys Ser Phe Val Val Ser Asn Gln Leu Arg Glu
        35                  40                  45

Gln Gln Gly Glu Leu Thr Ser Thr Trp Asp Leu Met Leu Gln Thr Arg
    50                  55                  60

Ile Asn Leu Ser Arg Ser Ala Val Arg Met Met Met Asp Ser Ser Asn
65                  70                  75                  80

Gln Gln Ser Asn Ala Lys Val Glu Leu Leu Asp Ser Ala Arg Lys Thr
                85                  90                  95

Leu Ala Gln Ala Ala Thr His Tyr Lys Lys Phe Lys Ser Met Ala Pro
            100                 105                 110

Leu Pro Glu Met Val Ala Thr Ser Arg Asn Ile Asp Glu Lys Tyr Lys
        115                 120                 125

Asn Tyr Tyr Thr Ala Leu Thr Glu Leu Ile Asp Tyr Leu Asp Tyr Gly
    130                 135                 140

Asn Thr Gly Ala Tyr Phe Ala Gln Pro Thr Gln Gly Met Gln Asn Ala
145                 150                 155                 160

Met Gly Glu Arg Phe Ala Gln Tyr Ala Leu Ser Glu Lys Leu Tyr
            165                 170                 175

Arg Asp Ile Val Thr Asp Asn Ala Asp Asp Tyr Arg Phe Ala Gln Trp
        180                 185                 190

Gln Leu Ala Val Ile Ala Leu Val Val Leu Ile Leu Leu Val Ala
    195                 200                 205

Trp Tyr Gly Ile Arg Arg Met Leu Leu Thr Pro Leu Ala Lys Ile Ile
        210                 215                 220

Ala His Ile Arg Glu Ile Ala Gly Gly Asn Leu Ala Asn Thr Leu Thr
225                 230                 235                 240

Ile Asp Gly Arg Ser Glu Met Gly Asp Leu Ala Gln Ser Val Ser His
                245                 250                 255
```

```
Met Ala Ala Gly Val Lys Gln Leu Ala Asp Asp Arg Thr Leu Leu Met
                260                 265                 270

Ala Gly Val Ser His Asp Leu Arg Thr Pro Leu Thr Arg Ile Arg Leu
            275                 280                 285

Ala Thr Glu Met Met Ser Glu Gln Asp Gly Tyr Leu Ala Glu Ser Ile
        290                 295                 300

Asn Lys Asp Ile Glu Glu Cys Asn Ala Ile Ile Glu Gln Phe Ile Asp
305                 310                 315                 320

Tyr Leu Arg Thr Gly Gln Glu Met Pro Met Glu Met Ala Asp Leu Asn
                325                 330                 335

Ala Val Leu Gly Glu Val Ile Ala Ala Glu Ser Gly Tyr Glu Arg Glu
            340                 345                 350

Ile Glu Thr Ala Leu Tyr Pro Gly Ser Ile Glu Val Lys Met His Pro
        355                 360                 365

Leu Ser Ile Lys Arg Ala Val Ala Asn Met Val Val Asn Ala Ala Arg
370                 375                 380

Tyr Gly Asn Gly Trp Ile Lys Val Ser Ser Gly Thr Glu Pro Asn Arg
385                 390                 395                 400

Ala Trp Phe Gln Val Glu Asp Asp Gly Pro Gly Ile Ala Pro Glu Gln
                405                 410                 415

Arg Lys His Leu Phe Gln Pro Phe Val Arg Gly Asp Ser Ala Arg Thr
            420                 425                 430

Ile Ser Gly Thr Gly Leu Gly Leu Ala Ile Val Gln Arg Ile Val Asp
        435                 440                 445

Asn His Asn Gly Met Leu Glu Leu Gly Thr Ser Glu Arg Gly Gly Leu
450                 455                 460

Ser Ile Arg Ala Trp Leu Pro Val Pro Val Thr Arg Ala Gln Gly Thr
465                 470                 475                 480

Thr Lys Glu Gly

<210> SEQ ID NO 39
<211> LENGTH: 1455
<212> TYPE: DNA
<213> ORGANISM: Artificial Sequence
<220> FEATURE:
<223> OTHER INFORMATION: Fusion protein coding sequence

<400> SEQUENCE: 39
atgccgggcc gctccaagtg gtatagacgc tggcggccgc gctcgttgca ggcccgccag      60
ctgctggccg ccagcctcag tctggtggcc ttcctggcgc tggcgggtta cgcgctggat     120
gtggcgtttg ccgacaccgc cgaaaagaat ctgcgcgagc ggctgaagaa ctacgcttcc     180
gcgtatgcgg ccaatatcga tttcgtacgc gacggctcgc tgtacatcgg cgggcaaccg     240
cccgacccgc gtttcgatgt gcctggcggc gggctctatg tcgaagttgt acgtcccgac     300
gaaagctgga cctcgatgtc ggccgaaggc ccgaatattc gcacggccg catgctggag      360 ccgcgccagg aagagttcat cggcccgctg aaatgaccc agatcgacgg cagcctgggc     420
cagctgtatc gctacggcct gggcgtgagt tatgtcgaac gcaacacgg tggcgagatt      480 ccgtacacca tctatgtgat ggaagatgcg cgctcgatgg gcgcgcagct gcgcgtgttc     540
cgtggtgcgg tgtggttcta cctcggtagc gctggcgtgg tgttgctggt gttgcaggcc     600
ttcattctgc aatggagcct gcgtccgctg cggcgggtca tcaacgagct gaccaaggtg     660
cagcgcggcg agatccagcg catgagcgag cagcatccgc gcgagctgga gccgctgacc     720
```

```
gacagcatca atgcctttat cgagagcgtt aagcaactgg aaggggcgcg gcgtaacttt    780
tttgccaacg tgagccatga gttacgtacg ccattgaccg tgttacaggg ctacctggag    840
atgatgaatg agcagccgct ggaaggcgcg gtacgcgaaa aagcgttgca caccatgcgc    900
gagcagaccc agcggatgga aggactggtg aagcaattgc tgacgctgtc gaaaatagaa    960
gccgcaccga cgcatttgct caatgaaaag gttgatgtgc cgatgatgct gcgcgttgtt   1020
gagcgcgagg ctcagactct gagtcagaaa aacagacat ttacctttga gatagataac    1080
ggcctcaagg tgtctggcaa cgaagatcag ctacgcagtg cgatttcgaa cctggtctat   1140
aacgccgtga atcatacgcc ggaaggcacg catatcaccg tacgctggca gcgagtgccg   1200
cacggtgccg aatttagcgt tgaagataac ggaccgggca ttgcaccgga gcatattccg   1260
cgcctgaccg agcgttttta tcgcgttgat aaagcgcgtt cccggcaaac cggcggtagc   1320
ggattagggt tagcgatcgt gaaacatgct gtgaatcatc acgaaagtcg cctgaatatt   1380
gagagtacag taggaaaagg aacacgtttc agttttgtta tcccggaacg tttaattgcc   1440
aaaaacagcg attaa                                                    1455
```

<210> SEQ ID NO 40
<211> LENGTH: 484
<212> TYPE: PRT
<213> ORGANISM: Artificial Sequence
<220> FEATURE:
<223> OTHER INFORMATION: Fusion protein

<400> SEQUENCE: 40

```
Met Pro Gly Arg Ser Lys Trp Tyr Arg Arg Trp Arg Pro Arg Ser Leu
1               5                   10                  15

Gln Ala Arg Gln Leu Leu Ala Ala Ser Leu Ser Leu Val Ala Phe Leu
            20                  25                  30

Ala Leu Ala Gly Tyr Ala Leu Asp Val Ala Phe Ala Asp Thr Ala Glu
        35                  40                  45

Lys Asn Leu Arg Glu Arg Leu Lys Asn Tyr Ala Ser Ala Tyr Ala Ala
    50                  55                  60

Asn Ile Asp Phe Val Arg Asp Gly Ser Leu Tyr Ile Gly Gly Gln Pro
65                  70                  75                  80

Pro Asp Pro Arg Phe Asp Val Pro Gly Gly Gly Leu Tyr Val Glu Val
                85                  90                  95

Val Arg Pro Asp Glu Ser Trp Thr Ser Met Ser Ala Glu Gly Pro Asn
            100                 105                 110

Ile Pro His Gly Arg Met Leu Glu Pro Arg Gln Glu Glu Phe Ile Gly
        115                 120                 125

Pro Leu Glu Met Thr Gln Ile Asp Gly Ser Leu Gly Gln Leu Tyr Arg
    130                 135                 140

Tyr Gly Leu Gly Val Ser Tyr Val Glu Arg Glu His Gly Gly Glu Ile
145                 150                 155                 160

Pro Tyr Thr Ile Tyr Val Met Glu Asp Ala Arg Ser Met Gly Ala Gln
                165                 170                 175

Leu Arg Val Phe Arg Gly Ala Val Trp Phe Tyr Leu Gly Ser Ala Gly
            180                 185                 190

Val Val Leu Leu Val Leu Gln Ala Phe Ile Leu Gln Trp Ser Leu Arg
        195                 200                 205

Pro Leu Arg Arg Val Ile Asn Glu Leu Thr Lys Val Gln Arg Gly Glu
    210                 215                 220

Ile Gln Arg Met Ser Glu Gln His Pro Arg Glu Leu Glu Pro Leu Thr
```

```
                    225                 230                 235                 240
Asp Ser Ile Asn Ala Phe Ile Glu Ser Val Lys Gln Leu Gly Ala
                245                 250                 255
Arg Arg Asn Phe Phe Ala Asn Val Ser His Glu Leu Arg Thr Pro Leu
            260                 265                 270
Thr Val Leu Gln Gly Tyr Leu Glu Met Met Asn Glu Gln Pro Leu Glu
            275                 280                 285
Gly Ala Val Arg Glu Lys Ala Leu His Thr Met Arg Glu Gln Thr Gln
    290                  295                 300
Arg Met Glu Gly Leu Val Lys Gln Leu Leu Thr Leu Ser Lys Ile Glu
305                 310                 315                 320
Ala Ala Pro Thr His Leu Leu Asn Glu Lys Val Asp Val Pro Met Met
                325                 330                 335
Leu Arg Val Val Glu Arg Glu Ala Gln Thr Leu Ser Gln Lys Lys Gln
            340                 345                 350
Thr Phe Thr Phe Glu Ile Asp Asn Gly Leu Lys Val Ser Gly Asn Glu
            355                 360                 365
Asp Gln Leu Arg Ser Ala Ile Ser Asn Leu Val Tyr Asn Ala Val Asn
    370                 375                 380
His Thr Pro Glu Gly Thr His Ile Thr Val Arg Trp Gln Arg Val Pro
385                 390                 395                 400
His Gly Ala Glu Phe Ser Val Glu Asp Asn Gly Pro Gly Ile Ala Pro
                405                 410                 415
Glu His Ile Pro Arg Leu Thr Glu Arg Phe Tyr Arg Val Asp Lys Ala
            420                 425                 430
Arg Ser Arg Gln Thr Gly Gly Ser Gly Leu Gly Leu Ala Ile Val Lys
            435                 440                 445
His Ala Val Asn His His Glu Ser Arg Leu Asn Ile Glu Ser Thr Val
        450                 455                 460
Gly Lys Gly Thr Arg Phe Ser Phe Val Ile Pro Glu Arg Leu Ile Ala
465                 470                 475                 480
Lys Asn Ser Asp

<210> SEQ ID NO 41
<211> LENGTH: 2133
<212> TYPE: DNA
<213> ORGANISM: Artificial Sequence
<220> FEATURE:
<223> OTHER INFORMATION: Fusion protein coding sequence

<400> SEQUENCE: 41
atgactacta ctcgttctaa tatcaagaaa cgccgttcgt tggctaccct gatcaccaaa      60
attatcatcc tggtgctggc gccgattatt ctgggcatct tcatccagag ttactacttc     120
tctaaacaaa tcatctggca ggaagtggat cgcactaaac agcagacctc tgccctgatt     180
cacaacatct tgactcgca cttcgcagca atccagatcc accacgattc taactccaaa      240
tccgaagtta ttcgtgactt ctataccgat cgtgacacgg atgttctgaa cttcttcttc     300
ctgagcattg atcagagcga cccttctcat actccggaat ttcgcttcct gaccgaccac     360
aaaggtatca tctgggacga tggtaacgct cacttttacg cgttaacga cttgatcctg      420 gatagcctgg ctaaccgtgt gtctttcagc aacaactggt actatatcaa cgttatgacg     480
tccattgggt cccgacacat gctggttcgc cgtgtaccga tcctggatcc gtccaccggc     540
gaagttctgg gtttctcctt caatgcggta gttctggaca caacttcgc cctgatggaa      600
```

```
aaactgaaat ctgaatctaa cgttgacaac gttgtgctgg tagctaactc tgttccgctg    660
gcgaactctc tgatcggcga cgagccatat aacgtagctg acgtactgca acgcaaatcc    720
tccgataaac gtctggacaa actgctggtg atcgaaaccc cgatcgttgt taacgctgtt    780
accaccgagc tgtgcctgct gaccgttcaa gataaccaat cggttgtaac cctgcagatt    840
caacacatcc tggctatgct ggcaagcatc atcggcatga ttatgattgc gctgatgtct    900
cgcgagtgga tcgaatccaa agtgagcgca caactggaat ctctgatgtc ctatacccgt    960
agcgcgcgtg aagagaaagg tttcgaacgt ttcggtggtt cggacatcga agagttcgac   1020
catatcggct ccaccctgga atctaccttc gaagaactgg aagcgcagaa aaaatctttc   1080
cgtgacctgt ttaacttcgc gctgtctccg atcatggtgt ggagtgaaga atccgtgctg   1140
atccagatga atccagcagc gcgtaaagag ctggtaatcg aagacgacca cgaaattatg   1200
cacccggtgt tccaaggctt taaggagaaa ctaaccccgc acctgaaaat ggctgctcag   1260
ggtgctaccc ttaccggtgt aaatgtcccg atcggtaaca aaatctaccg ctggaacctg   1320
tctccgattc gtgtcgacgg tgacatctcc ggcattatcg ttcagggtca ggacattact   1380
accctgattg aagctgagaa acaaagcaat attgctcgcc gtgaagttaa gcaactggaa   1440
ggggcgcggc gtaactttt tgccaacgtg agccatgagt tacgtacgcc attgaccgtg   1500
ttacagggct acctggagat gatgaatgag cagccgctgg aaggcgcggt acgcgaaaaa   1560
gcgttgcaca ccatgcgcga gcagacccag cggatggaag gactggtgaa gcaattgctg   1620
acgctgtcga aaatagaagc cgcaccgacg catttgctca tgaaaaggt tgatgtgccg   1680 atgatgctgc gcgttgttga gcgcgaggct cagactctga gtcagaaaaa acagacattt   1740
acctttgaga tagataacgg cctcaaggtg tctggcaacg aagatcagct acgcagtgcg   1800
atttcgaacc tggtctataa cgccgtgaat catacgccgg aaggcacgca tatcaccgta   1860
cgctggcagc gagtgccgca cggtgccgaa tttagcgttg aagataacgg accgggcatt   1920
gcaccggagc atattccgcg cctgaccgag cgttttatc gcgttgataa agcgcgttcc   1980
cggcaaaccg gcggtagcgg attagggtta gcgatcgtga acatgctgt gaatcatcac   2040 gaaagtcgcc tgaatattga gagtacagta ggaaaaggaa cacgtttcag ttttgttatc   2100
ccggaacgtt taattgccaa aaacagcgat taa                                 2133
```

<210> SEQ ID NO 42
<211> LENGTH: 710
<212> TYPE: PRT
<213> ORGANISM: Artificial Sequence
<220> FEATURE:
<223> OTHER INFORMATION: Fusion protein

<400> SEQUENCE: 42

```
Met Thr Thr Thr Arg Ser Asn Ile Lys Lys Arg Ser Leu Ala Thr
1               5                   10                  15

Leu Ile Thr Lys Ile Ile Ile Leu Val Leu Ala Pro Ile Ile Leu Gly
            20                  25                  30

Ile Phe Ile Gln Ser Tyr Tyr Phe Ser Lys Gln Ile Ile Trp Gln Glu
        35                  40                  45

Val Asp Arg Thr Lys Gln Gln Thr Ser Ala Leu Ile His Asn Ile Phe
    50                  55                  60

Asp Ser His Phe Ala Ala Ile Gln Ile His His Asp Ser Asn Ser Lys
65                  70                  75                  80

Ser Glu Val Ile Arg Asp Phe Tyr Thr Asp Arg Asp Thr Asp Val Leu
                85                  90                  95
```

-continued

```
Asn Phe Phe Phe Leu Ser Ile Asp Gln Ser Asp Pro Ser His Thr Pro
            100                 105                 110
Glu Phe Arg Phe Leu Thr Asp His Lys Gly Ile Ile Trp Asp Asp Gly
            115                 120                 125
Asn Ala His Phe Tyr Gly Val Asn Asp Leu Ile Leu Asp Ser Leu Ala
        130                 135                 140
Asn Arg Val Ser Phe Ser Asn Asn Trp Tyr Tyr Ile Asn Val Met Thr
145                 150                 155                 160
Ser Ile Gly Ser Arg His Met Leu Val Arg Arg Val Pro Ile Leu Asp
                165                 170                 175
Pro Ser Thr Gly Glu Val Leu Gly Phe Ser Phe Asn Ala Val Val Leu
            180                 185                 190
Asp Asn Asn Phe Ala Leu Met Glu Lys Leu Lys Ser Glu Ser Asn Val
        195                 200                 205
Asp Asn Val Val Leu Val Ala Asn Ser Val Pro Leu Ala Asn Ser Leu
    210                 215                 220
Ile Gly Asp Glu Pro Tyr Asn Val Ala Asp Val Leu Gln Arg Lys Ser
225                 230                 235                 240
Ser Asp Lys Arg Leu Asp Lys Leu Leu Val Ile Glu Thr Pro Ile Val
                245                 250                 255
Val Asn Ala Val Thr Thr Glu Leu Cys Leu Leu Thr Val Gln Asp Asn
            260                 265                 270
Gln Ser Val Val Thr Leu Gln Ile Gln His Ile Leu Ala Met Leu Ala
        275                 280                 285
Ser Ile Ile Gly Met Ile Met Ile Ala Leu Met Ser Arg Glu Trp Ile
    290                 295                 300
Glu Ser Lys Val Ser Ala Gln Leu Glu Ser Leu Met Ser Tyr Thr Arg
305                 310                 315                 320
Ser Ala Arg Glu Glu Lys Gly Phe Glu Arg Phe Gly Gly Ser Asp Ile
                325                 330                 335
Glu Glu Phe Asp His Ile Gly Ser Thr Leu Glu Ser Thr Phe Glu Glu
            340                 345                 350
Leu Glu Ala Gln Lys Lys Ser Phe Arg Asp Leu Phe Asn Phe Ala Leu
        355                 360                 365
Ser Pro Ile Met Val Trp Ser Glu Glu Ser Val Leu Ile Gln Met Asn
    370                 375                 380
Pro Ala Ala Arg Lys Glu Leu Val Ile Glu Asp Asp His Glu Ile Met
385                 390                 395                 400
His Pro Val Phe Gln Gly Phe Lys Glu Lys Leu Thr Pro His Leu Lys
                405                 410                 415
Met Ala Ala Gln Gly Ala Thr Leu Thr Gly Val Asn Val Pro Ile Gly
            420                 425                 430
Asn Lys Ile Tyr Arg Trp Asn Leu Ser Pro Ile Arg Val Asp Gly Asp
        435                 440                 445
Ile Ser Gly Ile Ile Val Gln Gly Gln Asp Ile Thr Thr Leu Ile Glu
    450                 455                 460
Ala Glu Lys Gln Ser Asn Ile Ala Arg Arg Glu Val Lys Gln Leu Glu
465                 470                 475                 480
Gly Ala Arg Arg Asn Phe Phe Ala Asn Val Ser His Glu Leu Arg Thr
                485                 490                 495
Pro Leu Thr Val Leu Gln Gly Tyr Leu Glu Met Met Asn Glu Gln Pro
            500                 505                 510
```

| | | | | | | | | | | | |
|---|---|---|---|---|---|---|---|---|---|---|---|
|Leu|Glu|Gly|Ala|Val|Arg|Glu|Lys|Ala|Leu|His|Thr|Met|Arg|Glu|Gln|
| |515| | | |520| | | |525| | | | | | |

Thr Gln Arg Met Glu Gly Leu Val Lys Gln Leu Leu Thr Leu Ser Lys
        530                     535                     540

Ile Glu Ala Ala Pro Thr His Leu Leu Asn Glu Lys Val Asp Val Pro
545                     550                     555                 560

Met Met Leu Arg Val Val Glu Arg Glu Ala Gln Thr Leu Ser Gln Lys
                565                     570                     575

Lys Gln Thr Phe Thr Phe Glu Ile Asp Asn Gly Leu Lys Val Ser Gly
                580                     585                     590

Asn Glu Asp Gln Leu Arg Ser Ala Ile Ser Asn Leu Val Tyr Asn Ala
                595                     600                     605

Val Asn His Thr Pro Glu Gly Thr His Ile Thr Val Arg Trp Gln Arg
        610                     615                     620

Val Pro His Gly Ala Glu Phe Ser Val Glu Asp Asn Gly Pro Gly Ile
625                     630                     635                 640

Ala Pro Glu His Ile Pro Arg Leu Thr Glu Arg Phe Tyr Arg Val Asp
                645                     650                     655

Lys Ala Arg Ser Arg Gln Thr Gly Gly Ser Gly Leu Gly Leu Ala Ile
                660                     665                     670

Val Lys His Ala Val Asn His His Glu Ser Arg Leu Asn Ile Glu Ser
        675                     680                     685

Thr Val Gly Lys Gly Thr Arg Phe Ser Phe Val Ile Pro Glu Arg Leu
        690                     695                     700

Ile Ala Lys Asn Ser Asp
705                 710

<210> SEQ ID NO 43
<211> LENGTH: 1461
<212> TYPE: DNA
<213> ORGANISM: E. coli

<400> SEQUENCE: 43

```
atgaaaaaat tactgcgtct ttttttcccg ctctcgctgc gggtacgttt tctgttggca      60
acggcagcgg tagtactggt gctttcgctt gcctacggaa tggtcgcgct gatcggttat     120
agcgtcagtt tcgataaaac tacgtttcgg ctgttacgtg gcgagagcaa tctgttctat     180
accctttgcga agtgggaaaa caataagttg catgtcgagt acccgaaaaa tatcgacaag     240
caaagcccca ccatgacgct aatttatgat gagaacgggc agcttttatg gcgcaacgt      300
gacgtgccct ggctgatgaa gatgatccag cctgactggc tgaaatcgaa tggttttcat     360
gaaattgaag cggatgttaa cgataccagc ctcttgctga gtggagatca ttcgatacag     420
caacagttgc aggaagtgcg ggaagatgat gacgacgcgg agatgaccca ctcggtggca     480
gtaaacgtct acccggcaac atcgcggatg ccaaaattaa ccattgtggt ggtggatacc     540
attccggtgg agctaaaaag ttcctatatg gtctggagct ggtttatcta tgtgctctca     600
gccaatctgc tgttagtgat cccgctgctg tgggtcgccg cctggtggag tttacgcccc     660
atcgaagccc tggcaaaaga agtccgcgaa ctggaagaac ataaccgcga attgctcaat     720
ccagccacaa cgcgagaact gaccagtctg gtacgaaacc tgaaccgatt gttaaaaagt     780
gaacgcgaac gttacgacaa ataccgtacg acgctcaccg acctgaccca tagtctgaaa     840
acgccactgg cggtgctgca agtacgctgc cgttctctgc gtagtgaaaa gatgagcgtc     900
agtgatgctg agccggtaat gctggagcaa atcagccgca tttcacagca aattggctac     960
```

-continued

```
tacctgcatc gtgccagtat gcgcggcggg acattgctca gccgcgagct gcatccggtc  1020
gccccactgc tggacaatct cacctcagcg ctgaacaaag tgtatcaacg caaagggggtc  1080 aatatctctc tcgatatttc gccagagatc agctttgtcg gtgagcagaa cgattttgtc  1140
gaggtgatgg gcaacgtgct ggataatgcc tgtaaatatt gcctcgagtt tgtcgaaatt  1200
tctgcaaggc aaaccgacga gcatctctat attgtggtcg aggatgatgg ccccggtatt  1260
ccattaagca agcgagaggt catttttcgac cgtggtcaac gggttgatac tttacgccct  1320
gggcaaggtg tagggctggc ggtagcccgc gaaatcaccg agcaatatga gggtaaaatc  1380
gtcgccggag agagcatgct gggcggtgcg cggatggagg tgattttttgg tcgccagcat  1440 tctgcgccga aagatgaata a                                             1461
```

<210> SEQ ID NO 44
<211> LENGTH: 486
<212> TYPE: PRT
<213> ORGANISM: E. coli

<400> SEQUENCE: 44

```
Met Lys Lys Leu Leu Arg Leu Phe Phe Pro Leu Ser Leu Arg Val Arg
1               5                   10                  15

Phe Leu Leu Ala Thr Ala Ala Val Val Leu Val Leu Ser Leu Ala Tyr
            20                  25                  30

Gly Met Val Ala Leu Ile Gly Tyr Ser Val Ser Phe Asp Lys Thr Thr
        35                  40                  45

Phe Arg Leu Leu Arg Gly Glu Ser Asn Leu Phe Tyr Thr Leu Ala Lys
    50                  55                  60

Trp Glu Asn Asn Lys Leu His Val Glu Leu Pro Glu Asn Ile Asp Lys
65                  70                  75                  80

Gln Ser Pro Thr Met Thr Leu Ile Tyr Asp Glu Asn Gly Gln Leu Leu
                85                  90                  95

Trp Ala Gln Arg Asp Val Pro Trp Leu Met Lys Met Ile Gln Pro Asp
            100                 105                 110

Trp Leu Lys Ser Asn Gly Phe His Glu Ile Glu Ala Asp Val Asn Asp
        115                 120                 125

Thr Ser Leu Leu Leu Ser Gly Asp His Ser Ile Gln Gln Gln Leu Gln
    130                 135                 140

Glu Val Arg Glu Asp Asp Asp Ala Glu Met Thr His Ser Val Ala
145                 150                 155                 160

Val Asn Val Tyr Pro Ala Thr Ser Arg Met Pro Lys Leu Thr Ile Val
                165                 170                 175

Val Val Asp Thr Ile Pro Val Glu Leu Lys Ser Ser Tyr Met Val Trp
            180                 185                 190

Ser Trp Phe Ile Tyr Val Leu Ser Ala Asn Leu Leu Val Ile Pro
        195                 200                 205

Leu Leu Trp Val Ala Ala Trp Trp Ser Leu Arg Pro Ile Glu Ala Leu
    210                 215                 220

Ala Lys Glu Val Arg Glu Leu Glu Glu His Asn Arg Glu Leu Leu Asn
225                 230                 235                 240

Pro Ala Thr Thr Arg Glu Leu Thr Ser Leu Val Arg Asn Leu Asn Arg
                245                 250                 255

Leu Leu Lys Ser Glu Arg Glu Arg Tyr Asp Lys Tyr Arg Thr Thr Leu
            260                 265                 270

Thr Asp Leu Thr His Ser Leu Lys Thr Pro Leu Ala Val Leu Gln Ser
        275                 280                 285
```

```
Thr Leu Arg Ser Leu Arg Ser Glu Lys Met Ser Val Ser Asp Ala Glu
    290                 295                 300
Pro Val Met Leu Glu Gln Ile Ser Arg Ile Ser Gln Gln Ile Gly Tyr
305                 310                 315                 320
Tyr Leu His Arg Ala Ser Met Arg Gly Gly Thr Leu Leu Ser Arg Glu
                325                 330                 335
Leu His Pro Val Ala Pro Leu Leu Asp Asn Leu Thr Ser Ala Leu Asn
            340                 345                 350
Lys Val Tyr Gln Arg Lys Gly Val Asn Ile Ser Leu Asp Ile Ser Pro
        355                 360                 365
Glu Ile Ser Phe Val Gly Glu Gln Asn Asp Phe Val Glu Val Met Gly
    370                 375                 380
Asn Val Leu Asp Asn Ala Cys Lys Tyr Cys Leu Glu Phe Val Glu Ile
385                 390                 395                 400
Ser Ala Arg Gln Thr Asp Glu His Leu Tyr Ile Val Val Glu Asp Asp
                405                 410                 415
Gly Pro Gly Ile Pro Leu Ser Lys Arg Glu Val Ile Phe Asp Arg Gly
            420                 425                 430
Gln Arg Val Asp Thr Leu Arg Pro Gly Gln Gly Val Gly Leu Ala Val
        435                 440                 445
Ala Arg Glu Ile Thr Glu Gln Tyr Glu Gly Lys Ile Val Ala Gly Glu
    450                 455                 460
Ser Met Leu Gly Gly Ala Arg Met Glu Val Ile Phe Gly Arg Gln His
465                 470                 475                 480
Ser Ala Pro Lys Asp Glu
                485

<210> SEQ ID NO 45
<211> LENGTH: 2580
<212> TYPE: DNA
<213> ORGANISM: Vibrio harveyi

<400> SEQUENCE: 45
atgacaacaa cgcgatcaaa cattaaaaag cgtcgctcgc tggcgacgct cataacaaag    60
atcatcattt tagttcttgc cccaattatt ctggggattt tcattcagag ctattacttc   120
tccaagcaaa tcatttggca agaagtagac cgaaccaaac agcaaacctc tgcactgatc   180
cacaatatat ttgatagcca ctttgcggcg atccagatac atcatgacag taattccaag   240
agcgaagtca ttcgtgattt ctacactgat cgcgacacgg atgtgctcaa cttttcttc   300 ctcagtatcg accaaagcga tccgtcgcac acaccagaat tccgttttct aacggaccac   360
aaaggcatca tttgggacga tggaaatgcg catttctatg gtgtgaacga ccttatcctt   420
gatagccttg ccaatcgggt cagtttcagt aacaactggt attacattaa tgtcatgacc   480
tccattggtt ctagacacat gctcgtgcgc gtgtgccga tcctagaccc ttcaacagga   540
gaggtgcttg gtttctcatt taatgccgtc gtcttagaca caacttcgc tttgatggaa   600 aagctcaaga gtgaaagtaa cgtcgacaat gtggtgctgg ttgctaatag cgttcctta   660 gcaaactctt tgattggtga tgagccatat aacgttgctg atgtattgca gcgtaaaagt   720
tcagacaaaa gactcgataa gctgttggta atagaaacgc caatcgtcgt aaatgcagtg   780
actaccgagc tttgcttgtt gacggtacaa gacaatcaga gtgtggtgac attacaaatc   840
caacatattc tagccatgct tgcatcgatc atcggtatga tcatgattgc cttaatgagt   900
agggaatgga ttgagagtaa agtttcggcg cagttagaat cttttgatgtc ttacacccgc   960
```

-continued

```
tctgctcgtg aggaaaaagg gtttgaacga tttggcggtt cggatattga agagtttgat   1020
cacatcggtt caaccettga agtacattc gaagagcttg aagcgcagaa gaagtcgttc   1080
cgagatctgt ttaattttgc cttatcaccc atcatggttt ggtctgaaga gagtgtcctg   1140
attcagatga accctgccgc gcgcaaagaa ttagtgatcg aagacgatca tgaaatcatg   1200
catccggtct ccaaggctt taaagagaaa ttgaccccac acctcaaaat ggcggctcaa    1260
ggtgcgacgt tgactggggt gaacgtgcct attggtaata agatctaccg atggaacttg   1320
tcgccaattc gtgttgatgg cgatatcagt ggcattattg tgcaaggcca agacattaca   1380
acacttatcg aagccgagaa gcagagtaac attgcgcgta gagaagcaga aaaatcggcg   1440
caagcacgtg cagacttcct tgctaaaatg agccatgaaa ttcgtacgcc aatcaacggc   1500
attttaggtg tcgcccaatt attgaaagat tctgtcgata cacaagagca gaagaatcaa   1560
atcgacgtcc tgtgccacag tggcgagcac ttgcttgcag tactgaacga tattctcgat   1620
ttctcaaaga tagagcaggg caagttcaat attcagaaac cccgttctc cttcaccgat   1680
accatgcgta cattggaaaa tatttatcgt ccgatttgca caaataaggg ggtggagttg   1740
gtcatcgaga atgagcttga cccgaatgtt gaaatcttca ccgatcaagt ccgcttgaat   1800
cagattctat ttaacttagt gagtaatgcc gttaagttca cgccgattgg ctcgattcga   1860
ctgcacgcag aacttgaaca attctatggt gcggagaaca gcgtgttagt tgtggaactg   1920
actgatactg gcatcggcat tgaaagcgat aagctcgacc aaatgttcga acctttgtg    1980
caagaagagt cgacaaccac acgcgaatat ggcggtagcg gcctaggtt tgaccatcgtt   2040
aagaacctag tcgatatgtt agaaggtgat gttcaggtcc gcagtagcaa gggggggggg   2100
acaacatttg ttataacact tccagtaaaa gatcgtgagc gtgtcttaag gcctctggag   2160
gtcagtcaac gtatcaagcc ggaagccttg tttgatgaaa gtttaaaagt gctactggtg   2220
gaagataacc ataccaatgc gtttatcctt caggctttct gtaagaagta taaaatgcag   2280
gtggattggg cgaaagatgg gctggacgcg atggagctcc tttctgatac cacctacgat   2340
ctgatcctca tggataacca attaccccac cttggtggta ttgagaccac gcacgagatt   2400
cgccagaact tgaggcttgg aacgccaatt tacgcgtgta cagcagacac cgcgaaagaa   2460
accagtgatg cgtttatggc ggcaggtgca aactatgtca tgctgaagcc aattaaagag   2520
aatgcgttac atgaggcgtt tgtcgatttc aaacaacgtt tcttggtaga aagaacctaa   2580
```

<210> SEQ ID NO 46
<211> LENGTH: 859
<212> TYPE: PRT
<213> ORGANISM: Vibrio harveyi

<400> SEQUENCE: 46

```
Met Thr Thr Thr Arg Ser Asn Ile Lys Lys Arg Arg Ser Leu Ala Thr
1               5                   10                  15

Leu Ile Thr Lys Ile Ile Ile Leu Val Leu Ala Pro Ile Ile Leu Gly
            20                  25                  30

Ile Phe Ile Gln Ser Tyr Tyr Phe Ser Lys Gln Ile Ile Trp Gln Glu
        35                  40                  45

Val Asp Arg Thr Lys Gln Gln Thr Ser Ala Leu Ile His Asn Ile Phe
    50                  55                  60

Asp Ser His Phe Ala Ala Ile Gln Ile His His Asp Ser Asn Ser Lys
65                  70                  75                  80

Ser Glu Val Ile Arg Asp Phe Tyr Thr Asp Arg Asp Thr Asp Val Leu
```

```
            85                  90                  95
Asn Phe Phe Leu Ser Ile Asp Gln Ser Asp Pro Ser His Thr Pro
            100                 105                 110
Glu Phe Arg Phe Leu Thr Asp His Lys Gly Ile Ile Trp Asp Asp Gly
            115                 120                 125
Asn Ala His Phe Tyr Gly Val Asn Asp Leu Ile Leu Asp Ser Leu Ala
    130                 135                 140
Asn Arg Val Ser Phe Ser Asn Asn Trp Tyr Tyr Ile Asn Val Met Thr
145                 150                 155                 160
Ser Ile Gly Ser Arg His Met Leu Val Arg Arg Val Pro Ile Leu Asp
                165                 170                 175
Pro Ser Thr Gly Glu Val Leu Gly Phe Ser Phe Asn Ala Val Val Leu
            180                 185                 190
Asp Asn Asn Phe Ala Leu Met Glu Lys Leu Lys Ser Glu Ser Asn Val
            195                 200                 205
Asp Asn Val Val Leu Val Ala Asn Ser Val Pro Leu Ala Asn Ser Leu
    210                 215                 220
Ile Gly Asp Glu Pro Tyr Asn Val Ala Asp Val Leu Gln Arg Lys Ser
225                 230                 235                 240
Ser Asp Lys Arg Leu Asp Lys Leu Leu Val Ile Glu Thr Pro Ile Val
                245                 250                 255
Val Asn Ala Val Thr Thr Glu Leu Cys Leu Leu Thr Val Gln Asp Asn
            260                 265                 270
Gln Ser Val Val Thr Leu Gln Ile Gln His Ile Leu Ala Met Leu Ala
            275                 280                 285
Ser Ile Ile Gly Met Ile Met Ile Ala Leu Met Ser Arg Glu Trp Ile
    290                 295                 300
Glu Ser Lys Val Ser Ala Gln Leu Glu Ser Leu Met Ser Tyr Thr Arg
305                 310                 315                 320
Ser Ala Arg Glu Glu Lys Gly Phe Glu Arg Phe Gly Gly Ser Asp Ile
                325                 330                 335
Glu Glu Phe Asp His Ile Gly Ser Thr Leu Glu Ser Thr Phe Glu Glu
            340                 345                 350
Leu Glu Ala Gln Lys Lys Ser Phe Arg Asp Leu Phe Asn Phe Ala Leu
            355                 360                 365
Ser Pro Ile Met Val Trp Ser Glu Glu Ser Val Leu Ile Gln Met Asn
    370                 375                 380
Pro Ala Ala Arg Lys Glu Leu Val Ile Glu Asp Asp His Glu Ile Met
385                 390                 395                 400
His Pro Val Phe Gln Gly Phe Lys Glu Lys Leu Thr Pro His Leu Lys
                405                 410                 415
Met Ala Ala Gln Gly Ala Thr Leu Thr Gly Val Asn Val Pro Ile Gly
            420                 425                 430
Asn Lys Ile Tyr Arg Trp Asn Leu Ser Pro Ile Arg Val Asp Gly Asp
            435                 440                 445
Ile Ser Gly Ile Ile Val Gln Gly Gln Asp Ile Thr Thr Leu Ile Glu
    450                 455                 460
Ala Glu Lys Gln Ser Asn Ile Ala Arg Arg Glu Ala Glu Lys Ser Ala
465                 470                 475                 480
Gln Ala Arg Ala Asp Phe Leu Ala Lys Met Ser His Glu Ile Arg Thr
                485                 490                 495
Pro Ile Asn Gly Ile Leu Gly Val Ala Gln Leu Leu Lys Asp Ser Val
            500                 505                 510
```

Asp Thr Gln Glu Gln Lys Asn Gln Ile Asp Val Leu Cys His Ser Gly
        515                 520                 525

Glu His Leu Leu Ala Val Leu Asn Asp Ile Leu Asp Phe Ser Lys Ile
530                 535                 540

Glu Gln Gly Lys Phe Asn Ile Gln Lys His Pro Phe Ser Phe Thr Asp
545                 550                 555                 560

Thr Met Arg Thr Leu Glu Asn Ile Tyr Arg Pro Ile Cys Thr Asn Lys
            565                 570                 575

Gly Val Glu Leu Val Ile Glu Asn Glu Leu Asp Pro Asn Val Glu Ile
        580                 585                 590

Phe Thr Asp Gln Val Arg Leu Asn Gln Ile Leu Phe Asn Leu Val Ser
    595                 600                 605

Asn Ala Val Lys Phe Thr Pro Ile Gly Ser Ile Arg Leu His Ala Glu
610                 615                 620

Leu Glu Gln Phe Tyr Gly Ala Glu Asn Ser Val Leu Val Glu Leu
625                 630                 635                 640

Thr Asp Thr Gly Ile Gly Ile Glu Ser Asp Lys Leu Asp Gln Met Phe
            645                 650                 655

Glu Pro Phe Val Gln Glu Ser Thr Thr Arg Glu Tyr Gly Gly
        660                 665                 670

Ser Gly Leu Gly Leu Thr Ile Val Lys Asn Leu Val Asp Met Leu Glu
    675                 680                 685

Gly Asp Val Gln Val Arg Ser Ser Lys Gly Gly Thr Thr Phe Val
        690                 695                 700

Ile Thr Leu Pro Val Lys Asp Arg Glu Arg Val Leu Arg Pro Leu Glu
705                 710                 715                 720

Val Ser Gln Arg Ile Lys Pro Glu Ala Leu Phe Asp Glu Ser Leu Lys
            725                 730                 735

Val Leu Leu Val Glu Asp Asn His Thr Asn Ala Phe Ile Leu Gln Ala
                740                 745                 750

Phe Cys Lys Lys Tyr Lys Met Gln Val Asp Trp Ala Lys Asp Gly Leu
    755                 760                 765

Asp Ala Met Glu Leu Leu Ser Asp Thr Thr Tyr Asp Leu Ile Leu Met
770                 775                 780

Asp Asn Gln Leu Pro His Leu Gly Gly Ile Glu Thr His Glu Ile
785                 790                 795                 800

Arg Gln Asn Leu Arg Leu Gly Thr Pro Ile Tyr Ala Cys Thr Ala Asp
            805                 810                 815

Thr Ala Lys Glu Thr Ser Asp Ala Phe Met Ala Ala Gly Ala Asn Tyr
                820                 825                 830

Val Met Leu Lys Pro Ile Lys Glu Asn Ala Leu His Glu Ala Phe Val
    835                 840                 845

Asp Phe Lys Gln Arg Phe Leu Val Glu Arg Thr
850                 855

<210> SEQ ID NO 47
<211> LENGTH: 22
<212> TYPE: DNA
<213> ORGANISM: Artificial Sequence
<220> FEATURE:
<223> OTHER INFORMATION: PhoB recognition sequence
<220> FEATURE:
<221> NAME/KEY: misc_feature
<222> LOCATION: (22)..(22)
<223> OTHER INFORMATION: n is a, c, g, or t

```
<400> SEQUENCE: 47
ctgtcataya yctgtcacay yn                                              22

<210> SEQ ID NO 48
<211> LENGTH: 28
<212> TYPE: PRT
<213> ORGANISM: Artificial Sequence
<220> FEATURE:
<223> OTHER INFORMATION: Fusion protein peptide fragment

<400> SEQUENCE: 48

Ser Arg His Leu Gln His Met Ala Ala Gly Val Lys Gln Leu Ala Asp
1               5                   10                  15

Asp Arg Thr Leu Leu Met Ala Gly Val Ser His Asp
            20                  25

<210> SEQ ID NO 49
<211> LENGTH: 28
<212> TYPE: PRT
<213> ORGANISM: Artificial Sequence
<220> FEATURE:
<223> OTHER INFORMATION: PhoR protein peptide fragment

<400> SEQUENCE: 49

Leu Leu Met Val Ala Arg Asp Val Thr Gln Met His Gln Leu Glu Gly
1               5                   10                  15

Ala Arg Arg Asn Phe Phe Ala Asn Val Ser His Glu
            20                  25

<210> SEQ ID NO 50
<211> LENGTH: 28
<212> TYPE: PRT
<213> ORGANISM: Artificial Sequence
<220> FEATURE:
<223> OTHER INFORMATION: EnvZ protein peptide fragment

<400> SEQUENCE: 50

Thr Arg Ala Phe Asn His Met Ala Ala Gly Val Lys Gln Leu Ala Asp
1               5                   10                  15

Asp Arg Thr Leu Leu Met Ala Gly Val Ser His Asp
            20                  25

<210> SEQ ID NO 51
<211> LENGTH: 28
<212> TYPE: PRT
<213> ORGANISM: Artificial Sequence
<220> FEATURE:
<223> OTHER INFORMATION: Fusion protein peptide fragment

<400> SEQUENCE: 51

Ser Arg His Leu Gln Gln Met Gln His Ser Leu Gly Met Thr Val Gly
1               5                   10                  15

Thr Val Arg Gln Gly Ala Glu Glu Ile Tyr Arg Gly
            20                  25

<210> SEQ ID NO 52
<211> LENGTH: 28
<212> TYPE: PRT
<213> ORGANISM: Artificial Sequence
<220> FEATURE:
<223> OTHER INFORMATION: Fusion protein peptide fragment

<400> SEQUENCE: 52

Ser Glu His Leu Gln His Met Ala Ala Gly Val Lys Gln Leu Ala Asp
```

```
                1               5                  10                  15
Asp Arg Thr Leu Leu Met Ala Gly Val Ser His Asp
            20                  25
```

<210> SEQ ID NO 53
<211> LENGTH: 28
<212> TYPE: PRT
<213> ORGANISM: Artificial Sequence
<220> FEATURE:
<223> OTHER INFORMATION: PhoR protein peptide fragment

<400> SEQUENCE: 53

```
Leu Leu Met Val Ala Arg Asp Val Thr Gln Met His Gln Leu Glu Gly
1               5                  10                  15
Ala Arg Arg Asn Phe Phe Ala Asn Val Ser His Glu
            20                  25
```

<210> SEQ ID NO 54
<211> LENGTH: 28
<212> TYPE: PRT
<213> ORGANISM: Artificial Sequence
<220> FEATURE:
<223> OTHER INFORMATION: Fusion protein peptide fragment

<400> SEQUENCE: 54

```
Ser Arg His Leu Gln Gln Met Gln His Ser Leu Gly Met Thr Glu Gly
1               5                  10                  15
Ala Arg Arg Asn Phe Phe Ala Asn Val Ser His Glu
            20                  25
```

<210> SEQ ID NO 55
<211> LENGTH: 28
<212> TYPE: PRT
<213> ORGANISM: Artificial Sequence
<220> FEATURE:
<223> OTHER INFORMATION: Fusion protein peptide fragment

<400> SEQUENCE: 55

```
Ser Arg His Leu Gln His Met Ala Ala Gly Val Lys Gln Leu Glu Gly
1               5                  10                  15
Ala Arg Arg Asn Phe Phe Ala Asn Val Ser His Glu
            20                  25
```

<210> SEQ ID NO 56
<211> LENGTH: 28
<212> TYPE: PRT
<213> ORGANISM: Artificial Sequence
<220> FEATURE:
<223> OTHER INFORMATION: Fusion protein peptide fragment

<400> SEQUENCE: 56

```
Ser Arg His Leu Gln His Met Ala Ala Gly Val Lys Gln Leu Ala Asp
1               5                  10                  15
Asp Arg Thr Leu Leu Phe Ala Asn Val Ser His Glu
            20                  25
```

<210> SEQ ID NO 57
<211> LENGTH: 28
<212> TYPE: PRT
<213> ORGANISM: Artificial Sequence
<220> FEATURE:
<223> OTHER INFORMATION: Fusion protein peptide fragment

<400> SEQUENCE: 57

-continued

Ser Arg His Leu Gln His Met Val Thr Gln Met His Gln Leu Glu Gly
1               5                   10                  15

Ala Arg Arg Asn Phe Phe Ala Asn Val Ser His Glu
            20                  25

<210> SEQ ID NO 58
<211> LENGTH: 28
<212> TYPE: PRT
<213> ORGANISM: Artificial Sequence
<220> FEATURE:
<223> OTHER INFORMATION: Fusion protein peptide fragment

<400> SEQUENCE: 58

Ser Arg His Leu Gln His Met Ala Ala Gly Met His Gln Leu Glu Gly
1               5                   10                  15

Ala Arg Arg Asn Phe Phe Ala Asn Val Ser His Glu
            20                  25

<210> SEQ ID NO 59
<211> LENGTH: 28
<212> TYPE: PRT
<213> ORGANISM: Artificial Sequence
<220> FEATURE:
<223> OTHER INFORMATION: Fusion protein peptide fragment

<400> SEQUENCE: 59

Ser Arg His Leu Gln His Met Ala Ala Gly Val His Gln Leu Glu Gly
1               5                   10                  15

Ala Arg Arg Asn Phe Phe Ala Asn Val Ser His Glu
            20                  25

<210> SEQ ID NO 60
<211> LENGTH: 28
<212> TYPE: PRT
<213> ORGANISM: Artificial Sequence
<220> FEATURE:
<223> OTHER INFORMATION: Fusion protein peptide fragment

<400> SEQUENCE: 60

Ser Arg His Leu Gln His Met Ala Ala Gly Val Lys Gln Leu Glu Gly
1               5                   10                  15

Ala Arg Arg Asn Phe Phe Ala Asn Val Ser His Glu
            20                  25

<210> SEQ ID NO 61
<211> LENGTH: 28
<212> TYPE: PRT
<213> ORGANISM: Artificial Sequence
<220> FEATURE:
<223> OTHER INFORMATION: Fusion protein peptide fragment

<400> SEQUENCE: 61

Ser Arg His Leu Gln His Met Gln His Ser Val His Gln Leu Glu Gly
1               5                   10                  15

Ala Arg Arg Asn Phe Phe Ala Asn Val Ser His Glu
            20                  25

<210> SEQ ID NO 62
<211> LENGTH: 28
<212> TYPE: PRT
<213> ORGANISM: Artificial Sequence
<220> FEATURE:
<223> OTHER INFORMATION: Fusion protein peptide fragment

<400> SEQUENCE: 62

Ser Arg His Leu Gln His Met Ala Ala Gly Met His Gln Leu Glu Gly
1               5                   10                  15

Ala Arg Arg Asn Phe Phe Ala Asn Val Ser His Glu
            20                  25

<210> SEQ ID NO 63
<211> LENGTH: 28
<212> TYPE: PRT
<213> ORGANISM: Artificial Sequence
<220> FEATURE:
<223> OTHER INFORMATION: Fusion protein peptide fragment

<400> SEQUENCE: 63

Ser Arg His Leu Gln His Met Ala Ala Gly Met His Gln Leu Glu Gly
1               5                   10                  15

Ala Arg Arg Asn Phe Phe Ala Asn Val Ser His Glu
            20                  25

<210> SEQ ID NO 64
<211> LENGTH: 28
<212> TYPE: PRT
<213> ORGANISM: Artificial Sequence
<220> FEATURE:
<223> OTHER INFORMATION: Fusion protein peptide fragment

<400> SEQUENCE: 64

Ser Arg His Leu Gln His Met Gln His Ser Val His Gln Leu Glu Gly
1               5                   10                  15

Ala Arg Arg Asn Phe Phe Ala Asn Val Ser His Glu
            20                  25

<210> SEQ ID NO 65
<211> LENGTH: 28
<212> TYPE: PRT
<213> ORGANISM: Artificial Sequence
<220> FEATURE:
<223> OTHER INFORMATION: Fusion protein peptide fragment

<400> SEQUENCE: 65

Ser Arg His Leu Gln His Met Gln His Ser Gly His Gln Leu Glu Gly
1               5                   10                  15

Ala Arg Arg Asn Phe Phe Ala Asn Val Ser His Glu
            20                  25

<210> SEQ ID NO 66
<211> LENGTH: 28
<212> TYPE: PRT
<213> ORGANISM: Artificial Sequence
<220> FEATURE:
<223> OTHER INFORMATION: Fusion protein peptide fragment

<400> SEQUENCE: 66

Ser Arg His Leu Gln His Met Gln His Ser Ala His Gln Leu Glu Gly
1               5                   10                  15

Ala Arg Arg Asn Phe Phe Ala Asn Val Ser His Glu
            20                  25

<210> SEQ ID NO 67
<211> LENGTH: 28
<212> TYPE: PRT
<213> ORGANISM: Artificial Sequence
<220> FEATURE:
<223> OTHER INFORMATION: Fusion protein peptide fragment

```
<400> SEQUENCE: 67

Ser Arg His Leu Gln His Met Gln His Ser Leu His Gln Leu Glu Gly
1               5                   10                  15

Ala Arg Arg Asn Phe Phe Ala Asn Val Ser His Glu
            20                  25

<210> SEQ ID NO 68
<211> LENGTH: 28
<212> TYPE: PRT
<213> ORGANISM: Artificial Sequence
<220> FEATURE:
<223> OTHER INFORMATION: Fusion protein peptide fragment

<400> SEQUENCE: 68

Ser Arg His Leu Gln His Met Gln His Ser Ile His Gln Leu Glu Gly
1               5                   10                  15

Ala Arg Arg Asn Phe Phe Ala Asn Val Ser His Glu
            20                  25

<210> SEQ ID NO 69
<211> LENGTH: 28
<212> TYPE: PRT
<213> ORGANISM: Artificial Sequence
<220> FEATURE:
<223> OTHER INFORMATION: Fusion protein peptide fragment

<400> SEQUENCE: 69

Ser Arg His Leu Gln His Met Gln His Ser Glu His Gln Leu Glu Gly
1               5                   10                  15

Ala Arg Arg Asn Phe Phe Ala Asn Val Ser His Glu
            20                  25

<210> SEQ ID NO 70
<211> LENGTH: 28
<212> TYPE: PRT
<213> ORGANISM: Artificial Sequence
<220> FEATURE:
<223> OTHER INFORMATION: Fusion protein peptide fragment

<400> SEQUENCE: 70

Ser Arg His Leu Gln His Met Gln His Ser Thr His Gln Leu Glu Gly
1               5                   10                  15

Ala Arg Arg Asn Phe Phe Ala Asn Val Ser His Glu
            20                  25

<210> SEQ ID NO 71
<211> LENGTH: 28
<212> TYPE: PRT
<213> ORGANISM: Artificial Sequence
<220> FEATURE:
<223> OTHER INFORMATION: Fusion protein peptide fragment

<400> SEQUENCE: 71

Thr Arg Ala Phe Asn His Met Ala Ala Gly Val Lys Gln Leu Ala Asp
1               5                   10                  15

Asp Arg Thr Leu Leu Met Ala Gly Val Ser His Asp
            20                  25

<210> SEQ ID NO 72
<211> LENGTH: 28
<212> TYPE: PRT
<213> ORGANISM: Artificial Sequence
<220> FEATURE:
<223> OTHER INFORMATION: Fusion protein peptide fragment
```

<400> SEQUENCE: 72

```
Leu Leu Met Val Ala Arg Asp Val Thr Gln Met His Gln Leu Glu Gly
1               5                   10                  15

Ala Arg Arg Asn Phe Phe Ala Asn Val Ser His Glu
            20                  25
```

<210> SEQ ID NO 73
<211> LENGTH: 1152
<212> TYPE: DNA
<213> ORGANISM: Artificial Sequence
<220> FEATURE:
<223> OTHER INFORMATION: Protein coding sequence

<400> SEQUENCE: 73

| | | | | | |
|---|---|---|---|---|---|
| atggaaagac | ctttcggatg | cttcttcatc | ttgctcctca | tctcttacac | cgtggttgct | 60 |
| aagatcgaag | agggaaagct | cgtgatctgg | ggaactggat | ctggtggact | taatggactt | 120 |
| gctgaggtgg | gaagaagtt | cgagaaggat | accggaacca | agtgaccgt | tgagggacct | 180 |
| gataagctcg | aagagaagtt | ccctcaagtg | gctgctactg | gtgatggacc | tgatattatc | 240 |
| ttcggacctc | acgctaggtt | cggaggatat | gctcaatctg | gacttctcgc | tgagatcacc | 300 |
| cctgataagg | ctttccagga | taagctctac | cctttcacct | gggatgctgt | gaggtacaac | 360 |
| ggaaagttga | tcgcttaccc | tatcgctgtt | gaggctctct | ctttgatcta | caacgaggat | 420 |
| ctcctcccaa | accctcctaa | gacctgggag | gaaattcctg | atcctggaaa | gtgtgctctc | 480 |
| atgttcaacc | tccaagagtg | gtggttcacc | tggcctccta | ttgctgctga | tggtggatac | 540 |
| gctttcaagt | acgagaacgg | aaagtacgat | attaaggatg | tgggagtgga | taacgctggt | 600 |
| gctaaggctg | gacttacttt | cctcgtggat | ctcatcgaga | caagcacat | gaacgctgat | 660 |
| accgattact | ctatcgctga | ggctgctctc | aacaagggtg | agactgctat | gaccatcaac | 720 |
| ggaccttggg | cttggtctaa | cattgatacc | tctaaggtga | actacggtgt | gaccgtgctc | 780 |
| cctactttta | agggacaacc | ttctaagcct | ttcgtgggag | ttgctgctgc | tggaatcaat | 840 |
| gctgcttctc | ctaacaaaga | gcttgctaaa | gagttccttg | agaactacct | cctcaccgat | 900 |
| gaaggacttg | aggctgtgaa | caaggataag | cctggtggtg | cttgggctct | caagtcttac | 960 |
| gaagaggaac | tcgctaaaga | tccaaggatc | gctgctacta | tggaaaacgc | tcaaaagggt | 1020 |
| gagatcatgc | ctaacatccc | tcagatgtct | gctttcgctt | acgctgtgag | aaccgctgtt | 1080 |
| atcaacgctg | cttctggtag | acagactgtg | gatgaggctc | tcaaggatgc | tcagaccagg | 1140 |
| attaccaagt | ga | | | | | 1152 |

<210> SEQ ID NO 74
<211> LENGTH: 2934
<212> TYPE: DNA
<213> ORGANISM: Artificial Sequence
<220> FEATURE:
<223> OTHER INFORMATION: Protein coding sequence

<400> SEQUENCE: 74

| | | | | | |
|---|---|---|---|---|---|
| atgagtagaa | ctcgacttcc | ttctccaccg | gcgccttcac | cggcttctc | tgccgactcg | 60 |
| ttctccgatc | tacttaggca | atttgatccg | agccttttta | acacgagttt | gttcgatagt | 120 |
| ctccctccgt | tcgggctca | tcacacagaa | gctgcgaccg | gagaatggga | tgaagtacaa | 180 |
| agcggactac | gtgccgcaga | tgctccgccc | ccgactatgc | gtgtcgcagt | tacggctgct | 240 |
| agaccgcctc | gtgccaagcc | tgcacccagg | cgtagggcag | ctcaaccgtc | ggatgctagt | 300 |

```
ccagcagcac aagtagactt gcgtactctg ggatattctc aacagcaaca ggaaaaaatt    360
aagcccaaag ttagaagtac agtagctcaa caccatgagg cgcttgttgg acatggcttt    420
actcatgcac atattgtggc actatcacaa caccccgcgg cacttggaac tgttgctgtc    480
aagtaccagg acatgattgc agcattacct gaagcaaccc acgaagcgat agtaggagtg    540
ggaaaacaat ggtcaggtgc tcgtgcactt gaggcattat taactgtggc tggcgaactg    600
cgtgggccac ctcttcaatt ggatacaggg cagttgctta aaatcgctaa gaggggagga    660
gttacagccg ttgaggcagt tcatgcatgg aggaacgctt taactggagc gccgttaaat    720
cttacgccag aacaggtggt tgcgattgcg tctaatatag gggggaagca ggctcttgag    780
actgtccaac gacttcttcc tgtgttgtgt caggcacatg gtttaactcc ggagcaggtt    840
gttgcaatag ctagccatga tgggggtaaa caagcccttg agacagttca aagacttctt    900
ccagtattat gtcaggctca tgggcttact ccagaacaag ttgtagcaat cgcttcgaac    960
ggaggtggaa agcaggctct tgaaacggtg caaagattgc ttcctgtgct ttgtcaggca   1020
cacggactaa ctcctgagca ggtagtagct attgcatcga acaacggggg taagcaggct   1080
ttggagactg ttcagagact ccttccggtg ttatgccaag cgcatggact taccccctgag  1140 caggttgtgg cgattgctag taacggagga ggtaaacaag cactggaaac cgttcagcgt   1200
cttcttcctg tgttgtgtca agcacacgga ttgaccccag agcaagttgt ggcaatagca   1260
tcacacgatg gaggtaagca agctcttgag actgttcaaa ggctgctacc tgttttgtgt   1320
caagcacatg gtcttacccc tgagcaagtc gttgctatcg catcacacga tgggggtaag   1380
caagcattgg agactgtcca acgactctta cctgttctct gccaagcaca tggacttacg   1440
cccgaacaag tagttgcgat tgcttccaac ggtggtggaa acaagctct cgaaacagtt    1500 cagcgtttac tacctgtttt tgtgtcaggct catggcctaa cgcctgaaca ggttgttgct   1560
attgcttccc atgatggtgg aaagcaagct ctcgaaacgg tccaaagatt acttcctgtc   1620
ctttgccagg ctcatggact cacccctgaa caggtcgttg ctatagccag tcatgacggt   1680
ggtaagcagg cacttgaaac cgtacaaagg ctattgcctg ttttgtgtca agctcatgga   1740
cttaccccag agcaggttgt agctatagca tcaaataacg gaggaaagca agcactagag   1800
actgtccagc gacttctacc ggtgttgtgt caggctcatg gtctaaccc tgagcaggtt    1860 gtggctattg ccagcaatat aggtggtaag caagctcttg agactgtgca aagattgctc   1920
cctgtcctat gccaagctca tggacttact cctgaacagg tcgtggcgat cgcatctaat   1980
aacggtggta acaagcgct tgagacggtc aaagattgc tacctgtctt atgccaggcc    2040
cacggactga cacctgaaca agttgtggct atcgcgtcaa atggtggtgg taagcaagct   2100
ctggagacag tgcagcgttt gcttcctgtg ctatgtcaag ctcatggact gacaccagag   2160
caagtagtgg ccattgctag tcatgatggg ggaaggcctg cgcttgagag catcgttgct   2220
caactttccc gaccagaccc agctttggct gcacttacca acgatcatct agttgcactt   2280
gcttgtctcg gaggaagacc cgcattggat gctgtaaaaa aaggttttgcc acatgctcct   2340 gctttaatca agagaacaaa tagaaggatt ccggaacgaa cgtctcatag ggtggcggac   2400
catgcacaag ttgtgagagt cttgggtttc tttcagtgtc attctcatcc tgcacaggct   2460
tttgacgacg ccatgactca gttcggaatg tcgagacatg gcctccttca gctgttcagg   2520
agagtgggag ttactgagct agaggcaaga agcgggacat tgccgccagc gtctcaacga   2580
tgggacagga ttctacaggc ttcaggaatg aaaaaggcta aacctagtcc gacttcaaca   2640
cagactccag atcaggcttc actccatgct tttgctgatt cattggagag agacttggat   2700
```

```
gctccatccc caatgcatga aggtgaccag acgcgtgcct cgggatcacc aaaaaagaaa    2760
agaaaggtgg gtagcgacgc attggatgat ttcgaccttg acatgttggg aagtgatgca    2820
ctagatgatt ttgacttgga tatgctcggt tccgatgctt tagatgactt tgatcttgac    2880
atgctaggta gtgatgcttt ggatgacttt gaccttgata tgctcggaag ttaa          2934
```

<210> SEQ ID NO 75
<211> LENGTH: 627
<212> TYPE: DNA
<213> ORGANISM: Artificial Sequence
<220> FEATURE:
<223> OTHER INFORMATION: Protein coding sequence

<400> SEQUENCE: 75

```
atgaagttgt taagttctat tgaacaggct tgtgatattt gtagattgaa gaagctcaag     60
tgtagtaaag agaaacctaa gtgcgctaag tgtcttaaaa ataactggga gtgcagatat    120
tctcctaaga ctaagagatc acctcttact agggctcatc tcacagaggt ggagtctagg    180
cttgagagat tggagcagtt gttccttttg attttccaa gagaagatct tgatatgatt     240
cttaagatgg attctcttca agatattaag gctcttctta ctggtttatt cgttcaagat    300
aatgtgaata aggatgcagt gactgataga cttgcatcag ttgaaactga tatgcctctt    360
acattaagac aacacaggat ttctgctact tcaagttctg aagaaagttc taataagggt    420
caaaggcaat taaccgtttc tgccgacgcg ctggacgatt cgatctcga catgctgggt     480 tctgatgccc tcgatgactt tgacctggat atgttgggaa cgacgcatt ggatgacttt     540 gatctggaca tgctcggctc cgatgctctg gacgatttcg atctcgatat gttaggttcc    600
cctaagaaga aaggaaggt gggttga                                          627
```

<210> SEQ ID NO 76
<211> LENGTH: 1653
<212> TYPE: DNA
<213> ORGANISM: Artificial Sequence
<220> FEATURE:
<223> OTHER INFORMATION: Protein coding sequence

<400> SEQUENCE: 76

```
atggaggatg ctaagaacat aaagaaggga cctgcaccat tttacccact tgaggatgga     60
actgctggag aacaattaca taaggctatg aagagatatg ctcttgttcc tggtactatc    120
gcattcacag atgctcatat agaggtgaac ataacttacg ctgagtactt cgaaatgtct    180
gttaggctcg ctgaagctat gaagagatac ggattaaata caaccacag gattgttgtg     240 tgtagtgaga actctttgca atttttcatg cctgttcttg gagctttgtt cataggagtg    300
gctgttgcac cagctaacga tatctataac gagagagaac ttttgaactc tatgaatatc    360
agtcaaccta ctgttgtgtt tgtgtctaag aaaggtcttc aaaagatatt gaacgttcag    420
aagaaacttc caattatcca gaagataatt atcatggatt caaaaacaga ttaccaaggt    480
ttccagtcaa tgtacacctt tgtgactagt catttgcctc ctggattcaa tgagtacgat    540
ttcgttccag aaagttttga tagagataag actattgctc tcatcatgaa ctcttcagga    600
tctacaggtc ttcctaaggg tgtggcattg ccacatagaa ccgcttgtgt taggttctct    660
cacgcaagag atcctatctt tggaaaccag ataattccag atacagctat tttgtcagtt    720
gtgcctttcc atcacggatt tggaatgttc actacactcg atatcttat ctgcggttt      780 agggttgtgc tcatgtacag attcgaagag gaactctttt taagatcttt acaagattat    840
```

-continued

```
aagatacagt cagcactctt agttccaacc cttttctctt tctttgctaa gtcaactttg      900
attgataagt acgatctttc taacttgcat gagatcgcaa gtggaggtgc tcctctttct      960
aaggaagtgg gtgaagcagt tgctaaaagg tttcacttgc caggaatcag acaaggatat     1020
ggacttactg aaactacttc tgctatcttg ataaccctg  aaggagatga taagccagga     1080
gcagttggta aagttgtgcc tttctttgaa gctaaggttg tggatctcga tacaggaaaa     1140
accttaggtg tgaatcagag gggagagctt tgcgttagag gtcctatgat aatgagtgga     1200
tatgttaata acccagaagc aactaacgct cttatagata aggatggatg gttgcattca     1260
ggagatattg cttactggga tgaggatgaa cactttttca ttgtggatag gctcaagtca     1320
ttaatcaagt ataagggata ccaagttgca cctgctgaac ttgaaagtat ccttttgcag     1380
catccaaaca tattcgatgc aggagttgct ggtcttcctg atgatgatgc tggtgaactt     1440
ccagctgcag ttgtggtttt agaacacgga aagactatga cagagaaaga aattgtggat     1500
tacgttgcat ctcaagttac aaccgctaag aaattgagag gtggtgtggt ttttgtggat     1560
gaagttccaa agggactcac aggtaaatta gatgctagaa aaatcagaga aatactcata     1620
aaggctaaaa aaggtggtaa atcaaaactc taa                                  1653
```

RECEPTOR/HISTIDINE KINASE FUSION CONSTRUCTS AND USES THEREOF

CROSS-REFERENCE TO RELATED APPLICATIONS

This application claims the priority of U.S. Provisional Appl. Ser. No. 62/701,396, filed Jul. 20, 2018, the entire disclosure of which is incorporated herein by reference.

STATEMENT REGARDING FEDERALLY SPONSORED RESEARCH OR DEVELOPMENT

This invention was made with government support under grant W911NF-09-1-0526 awarded by Army Research Office and grant N00014-07-1-0180 awarded by the Office of Naval Research. The government has certain rights in the invention.

INCORPORATION OF SEQUENCE LISTING

A sequence listing contained in the file named "CSUV004US.txt" which is 172 kilobytes (measured in MS-Windows®) and created on Jun. 18, 2019, is filed electronically herewith and incorporated by reference in its entirety.

FIELD OF THE INVENTION

The present disclosure relates to the field of molecular biology, more specifically compositions and methods involved in signal transduction from outside of a cell to the nucleus and to systems for sensing a target substance of interest in the environment and inducing gene expression in response thereto, useful for detection of biological and chemical agents, pathogens and their products and environmental pollutants especially with plants and plant sentinels.

BACKGROUND

Current detectors of biological and chemical agents and environmental pollutants involve electronic and/or vacuum-like mechanisms to sample the air or the environment. All current means to detect harmful biological or chemical agents and environmental pollutants are costly and require continuous maintenance. The high and continuous cost significantly limits the ability to detect biological and chemical agents, pathogens and their products, as well as environmental pollutants.

Therefore there is an increasing need for simple and robust detectors for harmful biological or chemical agents, pathogens and their products, and environmental pollutants.

SUMMARY OF THE INVENTION

The present disclosure provides a fusion protein comprising a chemotactic receptor protein, or a receptor involved in quorum sensing, or a receptor from a receptor histidine kinase operably linked at the A/D position to a histidine kinase protein, wherein the fusion protein comprises a kinase activation region. In certain embodiments the chemotactic receptor protein is Trg, Tar, Tap or Tsr. In other embodiments the receptor involved in quorum sensing is the Xylella DSF receptor RpfC or the LuxPQ receptor LuxP. In additional embodiments the histidine kinase protein is PhoR or EnvZ, while in further embodiments the histidine kinase protein is a EnvZ/PhoR chimera. In some embodiments the kinase activation region of the fusion protein has been engineered to restore inducible kinase activity or engineered to allow the interaction of maltose-bound maltose binding protein with the receptor to functionally activate kinase activity.

In particular embodiments the histidine kinase protein is activated when the chemotactic receptor protein or the receptor involved in quorum sensing binds to a sensor protein bound to a target substance or a target substance itself. Because of the diversity that nature provides from histidine kinases and with the ability afforded by computational design of proteins such as demonstrated here, in certain embodiments the fusions can be made where the target substance is a chemical agent, a heavy metal, a poison, a pollutant, a toxin, an herbicide, a polycyclic aromatic hydrocarbon, a benzene, a toluene, a xylene, a halogenated hydrocarbon, a steroid or other hormone, an explosive, or a degradation product of one of the foregoing compounds, most small molecules as enabled with computational design. In further embodiments the fusion protein further comprises a plasma membrane targeting signal sequence operably linked to an N-terminus of the chemotactic receptor protein or receptor involved in quorum sensing. Quorum sensing molecules are found in pathogen and their related products as demonstrated here and expanded with computational design abilities, hence our embodiments here and with computational abilities provide means to sense and respond to pathogens.

The present disclosure also provides a DNA construct comprising a nucleic acid segment that encodes a fusion protein comprising a chemotactic receptor protein, a receptor involved in quorum sensing, or a receptor from a receptor histidine kinase operably linked at the A/D position to a histidine kinase protein, wherein the fusion protein comprises a kinase activation region. In some embodiments the nucleic acid segment is operably linked to a heterologous or homologous promoter. In further embodiments the chemotactic receptor protein or the receptor involved in quorum sensing are or can be computationally designed.

The present disclosure further provides a transgenic plant or a plant cell comprising a first DNA construct comprising a first plant operable promoter operably linked to a nucleic acid segment encoding a sensor protein, the protein comprising a secretory sequence for directing the protein to the extracellular space of a plant cell and a binding region specific for a target substance of interest, wherein the protein undergoes a conformational change when the target substance is bound, a second DNA construct comprising a second plant operable promoter operably linked to a nucleic acid segment encoding a protein that comprises the following domains: a plasma membrane targeting signal sequence, an extracellular domain for binding the sensor protein, a transmembrane domain and a histidine kinase domain for phosphorylating a protein with nuclear shuttling or transcriptional activating functions, wherein the histidine kinase is activated when the sensor protein binds to the extracellular domain, and a third DNA construct comprising a third plant operable promoter operably linked to a nucleic acid segment encoding a detectable marker or a response gene, wherein the third plant operative promoter is responsive to the transcriptional activator protein, and wherein the detectable marker is expressed when the external target substance of interest is bound to the sensor protein. In particular embodiments the extracellular domain for binding the sensor protein comprises a chemotactic receptor protein, a receptor involved in quorum sensing, or a receptor from a receptor histidine kinase, and the extracellular domain or the transmembrane domain is operably linked at the A/D position to a histidine kinase protein, wherein the second DNA construct encodes a fusion protein comprising a kinase activation region.

In certain embodiments the extracellular domain, the transmembrane domain and/or the histidine kinase domain of the second DNA construct are derived from one or more bacterial genes, and the membrane targeting signal sequence of the second DNA construct is derived from a plant gene. The derived bacterial genes can be subjected to refactoring (codon optimization, removal of splice sites, post-translational regulatory elements, etc.) as is typical for one skilled in the field. In some embodiments the detectable marker of the third DNA construct is a chlorophyll degradation enzyme or a functional fragment thereof. In other embodiments the plant loses detectable green color when the detectable marker is expressed. In yet other embodiments the chlorophyll degradation enzyme is selected from the group consisting of red chlorophyll catabolite reductase (RCCR), pheophorbide a oxygenase (PaO), and chlorophyllase. In still other embodiments the third DNA construct comprises a plant operable promoter responsive to a transcription activator protein operably linked to a nucleic acid sequence encoding an interfering RNA molecule specific for a chlorophyll biosynthesis coding sequence. In further embodiments the chlorophyll biosynthesis coding sequence encodes chlorophyll synthetase, protochlorophyllide oxidoreductase (POR) or GUN4. In other embodiments the response or readout is non-visible but detectable by various systems including webcams and high altitude platforms.

In particular embodiments the secretory sequence is from pollen extension-like protein (PEX). In certain embodiments the membrane targeting signal sequence is from FLS2. In further embodiments the histidine kinase domain comprises segments derived from a non-plant organism or segments derived from a non-plant organism and a plant. In additional embodiments the plant operable promoter comprises a PhoB binding sequence.

In further embodiments the transgenic plant or plant cell further comprises a fourth DNA construct comprising a nucleic acid encoding a chlorophyll degradation enzyme or a functional fragment thereof operably linked to a plant operable promoter responsive to the transcription activator protein, and wherein the promoter is not in nature associated with the sequence encoding a chlorophyll degradation enzyme. In yet further embodiments the transgenic plant or plant cell further comprises a fourth DNA construct comprising a plant operable promoter operably linked to a nucleic acid sequence encoding a plant operable transcriptional activator, wherein the transcriptional activator is activated when phosphorylated by a histidine kinase.

In certain embodiments the detectable marker is a functional RNA. In some embodiments the functional RNA is an interfering RNA molecule. In other embodiments the functional RNA inhibits expression of a chlorophyll biosynthesis coding sequence. In particular embodiments the chlorophyll biosynthesis coding sequence encodes chlorophyll synthetase, protochlorophyllide oxidoreductase (POR) or GUN4. In additional embodiments the detectable marker is a chlorophyll degradation enzyme. In certain embodiments the chlorophyll degradation enzyme is red chlorophyll catabolite reductase (RCCR), pheophorbide a oxygenase (PaO), or chlorophyllase. In yet other embodiments the detectable marker is a β-glucuronidase, a β-galactosidase or a green or yellow fluorescent protein.

In some embodiments the transcription activator protein comprises a response regulator domain. In certain embodiments the response regulator domain is derived from PhoB. In particular embodiments the transcription activator protein is a PhoB:VP64 translational fusion protein. In further embodiments the detectable marker is a functional RNA that inhibits expression of a chlorophyll biosynthesis coding sequence. In still further embodiments the plant loses green color due to inhibition of chlorophyll biosynthesis and enhanced breakdown of chlorophyll upon induction of a gene encoding a chlorophyll degradation enzyme. In other embodiments the enhanced breakdown of chlorophyll is achieved by expressing at least one enzyme selected from the group consisting of red chlorophyll catabolite reductase (RCCR), pheide a oxygenase (PaO), and chlorophyllase. In yet other embodiments the inhibition of chlorophyll biosynthesis is achieved by inhibiting expression of at least one enzyme selected from the group consisting of protochlorophyllide oxidoreductase (POR), chlorophyll synthetase and GUN4. In certain embodiments the inhibition of POR is achieved by producing an interfering RNA molecule that contains a sequence derived from the coding sequence of POR. In further embodiments the plant loses green color by inhibiting POR and stimulating RCCR and chlorophyllase. In other embodiments the response or readout is non-visible but detectable by various systems including webcams and high altitude platforms.

The present disclosure additionally provides a plant cell comprising a first DNA construct comprising a first promoter functional in a plant operably linked to a recombinant nucleic acid encoding a first repressor, a second DNA construct comprising a second promoter functional in a plant operably linked to a nucleic acid encoding a detectable marker or response gene encoding a fusion protein comprising a chemotactic receptor protein, a receptor involved in quorum sensing, or a receptor from a receptor histidine kinase operably linked at the A/D position to a histidine kinase protein, wherein the fusion protein comprises a kinase activation region, wherein the second promoter is repressible by a second repressor, and a third DNA construct comprising a third promoter functional in a plant operably linked to a nucleic acid encoding the first repressor, wherein the third promoter is constitutive and repressible by the second repressor, wherein the first repressor or second repressor comprise at least one EAR 1 or EAR 2 repressor domain, or a transgenic plant comprising the plant cell. In further embodiments the plant cell comprises a fourth DNA construct comprising a fourth promoter operable in a plant operably linked to a nucleic acid encoding the second repressor, wherein the fourth promoter is constitutive and repressible.

In certain embodiments the fourth promoter is repressible by the first repressor. In some embodiments repression of the fourth promoter by the first repressor reduces expression of the second repressor. In other embodiments reduced expression of the second repressor increases expression of the detectable marker or response gene. In yet other embodiments the fourth promoter is a recombinant polynucleotide comprising nucleic acid sequence from a non-plant organism. In still other embodiments the nucleic acid encoding the first repressor is a recombinant polynucleotide. In particular embodiments the nucleic acid encoding the first repressor comprises nucleic acid sequences encoding at least one GAL4 DNA binding domain. In further embodiments the nucleic acid encoding the second repressor is a recombinant polynucleotide. In yet further embodiments the first promoter is a recombinant polynucleotide. In still further embodiments the first promoter is induced by a transcription activator protein activated by an external signal.

In additional embodiments the transcription activator protein is a fusion protein encoded by a polynucleotide sequence derived from a non-plant organism. In other embodiments the polynucleotide sequence encoding the fusion protein comprises at least one nucleic acid sequence encoding a PhoB binding domain. In some embodiments the fusion protein is encoded by a polynucleotide sequence comprising a nucleic acid sequence encoding a polypeptide sequence of VP64. In further embodiments the plant cell comprises a fifth DNA construct comprising a plant operable promoter operably linked to a nucleic acid sequence encoding a sensor protein that recognizes the external signal. In certain embodiments the second promoter is a recombinant polynucleotide.

The present disclosure also provides a method for detecting an external substance of interest, the method comprising exposing a transgenic plant or a plant cell comprising a first DNA construct comprising a first plant operable promoter operably linked to a nucleic acid segment encoding a sensor protein, the protein comprising a secretory sequence for directing the protein to the extracellular space of a plant cell and a binding region specific for a target substance of interest, wherein the protein undergoes a conformational change when the target substance is bound, a second DNA construct comprising a second plant operable promoter operably linked to a nucleic acid segment encoding a protein that comprises the following domains: a plasma membrane targeting signal sequence, an extracellular domain for binding the sensor protein, a transmembrane domain and a histidine kinase domain for phosphorylating a protein with nuclear shuttling and/or transcriptional activating functions, wherein the histidine kinase is activated when the sensor protein binds to the extracellular domain, and a third DNA construct comprising a third plant operable promoter operably linked to a nucleic acid segment encoding a detectable marker or a response gene, wherein the third plant operative promoter is responsive to the transcriptional activator protein, and wherein the detectable marker is expressed when the external target substance of interest is bound to the sensor protein, wherein the extracellular domain for binding the sensor protein comprises a chemotactic receptor protein, a receptor involved in quorum sensing, or a receptor from a receptor histidine kinase, and the extracellular domain or the transmembrane domain is operably linked at the A/D position to a histidine kinase protein, wherein the second DNA construct encodes a fusion protein comprising a kinase activation region to an external substance of interest, and detecting a change resulting from expression of the detectable marker.

In certain embodiments the detectable marker is a functional RNA. In some embodiments the functional RNA is an interfering RNA molecule. In other embodiments the functional RNA inhibits expression of a chlorophyll biosynthesis coding sequence. In yet other embodiments the chlorophyll biosynthesis coding sequence encodes chlorophyll synthetase, protochlorophyllide oxidoreductase (POR) or GUN4. In still other embodiments the detectable marker is a chlorophyll degradation enzyme. In further embodiments the chlorophyll degradation enzyme is red chlorophyll catabolite reductase (RCCR), pheophorbide a oxygenase (PaO), or chlorophyllase. In still further embodiments the detectable marker is a β-glucuronidase, a β-galactosidase or a green or yellow fluorescent protein. In other embodiments the response or readout is non-visible but detectable by various systems including webcams and high altitude platforms. In additional embodiments the transcription activator protein is a PhoB protein or is derived from a PhoB protein.

In some embodiments the transcription activator protein is a PhoB:VP64 translational fusion protein.

In certain embodiments the change is degreening of the transgenic plant. In some embodiments the degreening of the transgenic plant is detected visually or by detecting properties selected from the group consisting of chlorophyll fluorescence, photosynthetic properties and properties related to reactive oxygen species and their damage. In other embodiments the degreening is detected by imaging selected from the group consisting of hyper-spectral imaging, infrared imaging, near-infra-red imaging and multi-spectral imaging. In further embodiments the transgenic plant regreens after removal of the external substance of interest. In other embodiments the response or readout is non-visible but detectable by various systems including webcams and high altitude platforms. In another embodiment the external signal is detectable after a single exposure of the transgenic plant or plant cell to the external signal.

BRIEF DESCRIPTION OF THE DRAWINGS

For a more complete understanding of the features and advantages of the present disclosure, reference is now made to the detailed description of the disclosure along with the accompanying figures. The drawings described herein are for illustration purposes only and are not intended to limit the scope of the present teachings in any way.

FIG. 1A. "Simple" bacterial TCS—Extracellular input is provided by a transmembrane histidine kinase (HK). In the HK molecule a histidine residue in the dimerization and histidine phosphorylation (DHP) domain auto-phosphorylates in response to ligand binding. The high energy phosphoryl group is then transferred to a cytoplasmically localized response regulator (RR). FIG. 1B. Hybrid HK signaling found in plants and bacteria—These systems have more complex HKs and signaling components. In response to a ligand binding on the HK, a histidine residue in the DHP domain auto-phosphorylates. The high energy phosphoryl group is then transferred internally to an aspartate in the receiver domain, and subsequently to a histidine in a cytoplasmic Hpt protein which then phosphorylates an RR on its aspartate residue. FIG. 1C. Bacterial chemotactic TCS—A chemotactic receptor (e.g., Trg) binds a PBP-ligand complex or directly binds a ligand. This binding event initiates a signal that is transmitted to a cytoplasm-localized histidine kinase CheA. CheW acts as an adaptor protein for the chemotactic receptor/CheA complex. CheA then phosphorylates RRs that do not activate transcription.

FIG. 3A. End-on view looking from N terminus. The interface between the α-helices derives primarily from hydrophobic residues in core positions a and d, although there are also some salt bridges formed between residues e and g. FIG. 3B. The core interface viewed parallel to the coiled-coil axis shows how residues from one chain occupy the spaces between the corresponding residues from the second chain to give "knobs in holes" packing. FIG. 3C. Representation of a coiled coil structure.

FIG. 4. Predicted HK coiled coil element in Trz (SEQ ID NO:48) and PhoR (SEQ ID NO:53). Note that the methionine used in the HAMP fusion between Trg and EnvZ (underlined) is adjacent to the start of coiled coil heptad number 3.

FIG. 8. Coiled coil D position mutants TrzHAMP+M (SEQ ID NO:62), TrzHAMP+V (SEQ ID NO:63), TrgHAMP+V (SEQ ID NO:64), TrgHAMP+G (SEQ ID NO:65), TrgHAMP+A (SEQ ID NO:66), TrgHAMP+L (SEQ ID NO:67), TrgHAMP+I (SEQ ID NO:68), TrgHAMP+E (SEQ ID NO:69), and TrgHAMP+T (SEQ ID NO:70). Proteins used in the fusions are Trz (SEQ ID NO:52); Trg (SEQ ID NO:51); and PhoR (SEQ ID NO:53). TrgHAMP+G and TrgHAMP+A tested the effect of putting a smaller hydrophobic D position residue in place of the Valine. TrgHAMP+L,I,E or T tested the effect of placing a naturally occurring A/D residue from the 10 HKs found in E. coli that have the HAMP position A/D position HK Coiled coil architecture.

FIG. 9A and FIG. 9B. Imaging of a luciferase gene reporter in transgenic Arabidopsis with the signaling circuit Ribose Binding Protein (RBP)→TrzPhoR→PhoBVP64 activating a plant pho promoter: luciferase reporter gene FIG. 9A. Four transgenic Arabidopsis lines at 0 hours (no exposure to ribose) top panel and 24 hours after exposure to ribose bottom panel. FIG. 9B. Quantification of luciferase activity from FIG. 9A.

FIG. 11A. Paired detached leaf assay on a split plate with luciferase reporter readout, 24 hour exposure to DSF. Two leaves from 7 independent RpfCTrzPhoR transgenic lines were detached and placed on media without (left side) and with (right side) DSF extracted from Xylella. The signaling circuit is DSF→RpfCTrzPhoR-→PhoBVP64 activating a plant pho promoter. FIG. 11B. Quantification of luciferase activity. Mean activity of all 7 leaves.

FIG. 12A. Split plate assay showing $Mg^{2+}$ induction of PhoQTrzPhoR. Left=background signaling from 2 mM $MgSO_4$ present in media, Right=signaling increase seen with addition of 10 mM $MgCl_2$. FIG. 12B. β-galactosidase activity of PhoQTrzPhoR. Yellow=background signaling from $Mg^{2+}$ in media, Blue=signaling with additional 10 mM $Mg^{2+}$.

FIG. 13A. β-galactosidase activity of TrzChim3. Yellow=control, Blue=ribose. FIG. 13B. β-galactosidase activity of the TrzChim3 ADD→EGA mutant. Yellow=control, Blue=ribose.

FIG. 14. Alignment between EnvZ (SEQ ID NO:71) and PhoR (SEQ ID NO:72) indicating the ADD residues (275-277) of EnvZ and the corresponding EGA residues of PhoR in bold underline.

FIG. 17A and FIG. 17B. Normalized GFP reporter gene fluorescence showing maltose induction of the TarHK fusion variants TazPhoR (FIG. 17A) and TAC (FIG. 17B).

BRIEF DESCRIPTION OF THE SEQUENCES

Figure 1:
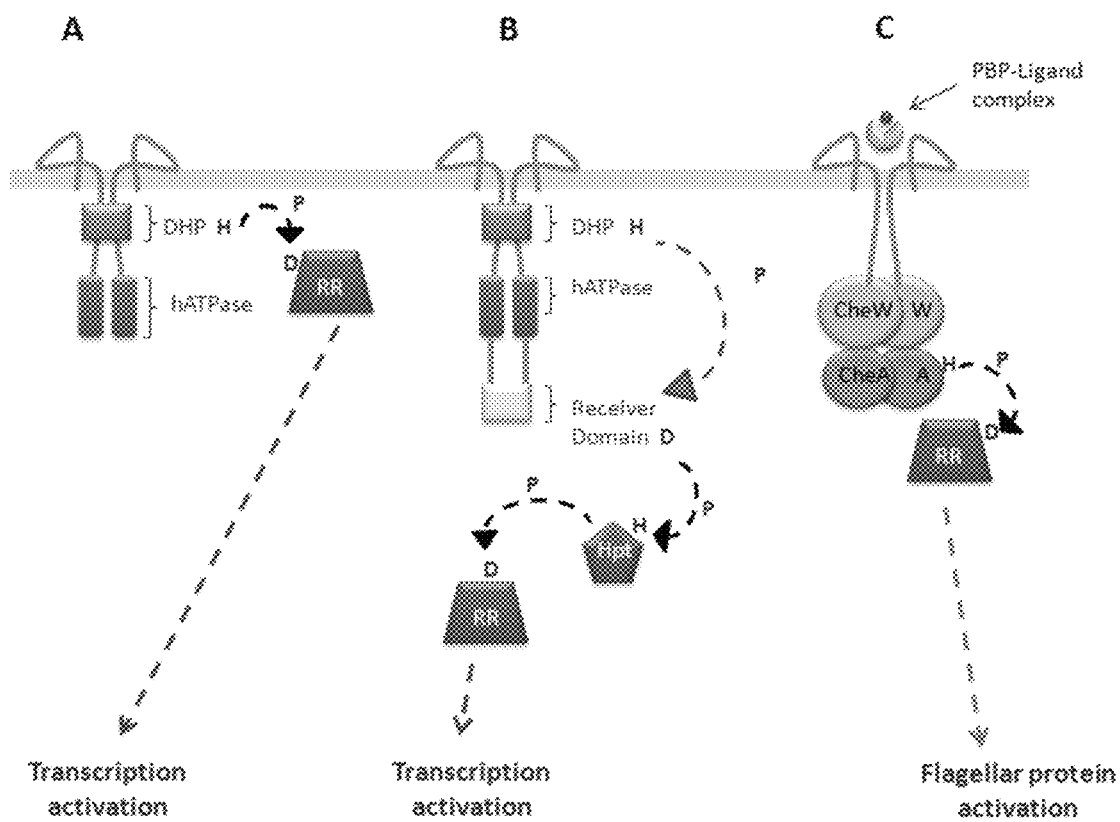
FIG. 1A, FIG. 1B and FIG. 1C: Diagrams of two component systems (TCS).

SEQ ID NO:1—DNA coding sequence of TrzPhoR coiled coil based fusion of Trz (Trg chemotactic receptor/EnvZ histidine kinase fusion) to PhoR histidine kinase *Escherichia coli* sequence.

SEQ ID NO:2—Protein sequence of TrzPhoR coiled coil based fusion of Trz (Trg chemotactic receptor/EnvZ histidine kinase fusion) to PhoR histidine kinase *Escherichia coli* sequence.

SEQ ID NO:3—DNA coding sequence of TrzPhoR: Trz HAMP domain+Valine A/D fusion to PhoR histidine kinase *Escherichia coli* sequence.

SEQ ID NO:4—Protein sequence of TrzPhoR: Trz HAMP domain+Valine A/D fusion (SEQ ID NO:48) to PhoR histidine kinase *Escherichia coli* sequence (SEQ ID NO:49).

SEQ ID NO:5—DNA coding sequence of RpfCPhoR Fusion of *Xylella fastidiosa* RpfC quorum sensing receptor to PhoR HK at A/D valine position, *Arahidopsis* codon optimized sequence.

SEQ ID NO:6—Protein sequence of RpfCPhoR Fusion of *Xylella fastidiosa* RpfC quorum sensing receptor to PhoR HK at A/D valine position, *Arabidopsis* codon optimized sequence.

SEQ ID NO:7—DNA coding sequence of TrzChim3: Trz with partial substitution of PhoR DHP domain *Escherichia coli* sequence.

SEQ ID NO:8—Protein sequence of TrzChim3: Trz with partial substitution of PhoR DHP domain *Escherichia coli* sequence.

SEQ ID NO:9—DNA coding sequence of TrzChim3 ADD to EGA variant *Escherichia coli* sequence.

SEQ ID NO:10—Protein sequence of TrzChim3 ADD to EGA variant *Escherichia coli* sequence.

SEQ ID NO:11—DNA coding sequence of TrzChim3-8 Directed evolution variant of TrzChim3 with restored on/off functionality *Escherichia coli* sequence.

SEQ ID NO:12—Protein sequence of TrzChim3-8 Directed evolution variant of TrzChim3 with restored on/off functionality *Escherichia coli* sequence.

SEQ ID NO:13—DNA coding sequence of TrzChim3-10 Directed evolution variant of TrzChim3 with restored on/off functionality *Escherichia coli* sequence.

SEQ ID NO:14—Protein sequence of TrzChim3-10 Directed evolution variant of TrzChim3 with restored on/off functionality *Escherichia coli* sequence.

SEQ ID NO:15—DNA coding sequence of TazPhoR: TrzPhoR fusion with the Tar chemotactic receptor replacing the Trg chemotactic receptor *Escherichia coli* sequence.

SEQ ID NO:16—Protein sequence of TazPhoR: TrzPhoR fusion with the Tar chemotactic receptor replacing the Trg chemotactic receptor *Escherichia coli* sequence.

SEQ ID NO:17—DNA coding sequence of TazPhoR 61: Maltose inducible directed evolution variant of TazPhoR *Escherichia coli* sequence.

SEQ ID NO:18—Protein sequence of TazPhoR 61: Maltose inducible directed evolution variant of TazPhoR *Escherichia coli* sequence.

SEQ ID NO:19—DNA coding sequence of TazPhoR 86: Maltose inducible directed evolution variant of TazPhoR *Escherichia coli* sequence.

SEQ ID NO:20—Protein sequence of TazPhoR 86: Maltose inducible directed evolution variant of TazPhoR *Escherichia coli* sequence.

SEQ ID NO:21—DNA coding sequence of Tac8: TrzChim3-8 with the chemotactic receptor Tar replacing the chemotactic receptor Trg *Escherichia coli* sequence.

SEQ ID NO:22—Protein sequence of Tac8: TrzChim3-8 with the chemotactic receptor Tar replacing the chemotactic receptor Trg *Escherichia coli* sequence.

SEQ ID NO:23—DNA coding sequence of Tac40: Maltose inducible directed evolution variant of Tac8.

SEQ ID NO:24—Protein sequence of Tac40: Maltose inducible directed evolution variant of Tac8.

SEQ ID NO:25—DNA coding sequence of PhoR Phosphate regulon sensor Histidine Kinase from *Escherichia coli.*

SEQ ID NO:26—Protein sequence of PhoR Phosphate regulon sensor Histidine Kinase from *Escherichia coli.*

SEQ ID NO:27—DNA coding sequence of Trg Ribose responsive chemotactic receptor that interacts with ribose binding protein (RBP) from *Escherichia coli.*

SEQ ID NO:28—Protein sequence of Trg Ribose responsive chemotactic receptor that interacts with ribose binding protein (RBP) from *Escherichia coli.*

SEQ ID NO:29—DNA coding sequence of Tar Aspartate and Maltose responsive chemotactic receptor that interacts with maltose binding protein from *Escherichia coli.*

SEQ ID NO:30—Protein sequence of Tar Aspartate and Maltose responsive chemotactic receptor that interacts with maltose binding protein from *Escherichia coli.*

SEQ ID NO:31—DNA coding sequence of EnvZ Histidine kinase involved in osmotic sensing from *Escherichia coli.*

SEQ ID NO:32—Protein sequence of EnvZ Histidine kinase involved in osmotic sensing from *Escherichia coli.*

SEQ ID NO:33—DNA coding sequence of RpfC Quorum sensing histidine kinase that senses diffusible signaling factor DSF from *Xylella fastidiosa.*

SEQ ID NO:34—Protein sequence of RpfC Quorum sensing histidine kinase that senses diffusible signaling factor DSF from *Xylella fastidiosa.*

SEQ ID NO:35—DNA coding sequence of Trz-Trg chemotactic receptor fused to EnvZ histidine kinase at conserved HAMP domain: Trg nt 1-801_EnvZ nt 802-end.

SEQ ID NO:36—Protein sequence of Trz-Trg chemotactic receptor fused to EnvZ histidine kinase at conserved HAMP domain: Trg aa 1-275_EnvZ aa 276-end.

SEQ ID NO:37—DNA coding sequence of Taz-Tar chemotactic receptor fused to EnvZ histidine kinase at conserved HAMP domain:Tar nt 1-778_EnvZ nt 779-end.

SEQ ID NO:38—Protein sequence of Taz-Tar chemotactic receptor fused to EnvZ histidine kinase at conserved HAMP domain:Tar aa 1-262_EnvZ aa 263-end.

SEQ ID NO:39—DNA coding sequence of PhoQTrzPhoR: $Mg^{2+}$ responsive PhoQ receptor fused to TzyPhoR at the D position. *Escherichia coli* sequence.

SEQ ID NO:40—Protein sequence of PhoQTrzPhoR: $Mg^{2+}$ responsive PhoQ receptor fused to TzyPhoR at the D position. *Escherichia coli* sequence.

SEQ ID NO:41—DNA coding sequence of LuxQTrzPhoR: D position fusion of receptor histidine kinase LuxA which quorum senses AI-2 and TrzPhoR LuxQ codon optimized for *Escherichia coli*. TrzPhoR *Escherichia coli* sequence.

SEQ ID NO:42—Protein sequence of LuxQTrzPhoR: D position fusion of receptor histidine kinase LuxA which quorum senses AI-2 and TrzPhoR LuxQ codon optimized for *Escherichia coli*. TrzPhoR *Escherichia coli* sequence.

SEQ ID NO:43—PhoQ DNA coding sequence from *Escherichia coli.*

SEQ ID NO:44—PhoQ protein sequence from *Escherichia coli*.

SEQ ID NO:45—DNA coding sequence of LuxQ Receptor Histidine Kinase involved in quorum sensing from *Vibrio harveyi*.

SEQ ID NO:46—Protein sequence of LuxQ Receptor Histidine Kinase involved in quorum sensing from *Vibrio harveyi*.

SEQ ID NO:47—DNA recognition sequence for PhoB.

SEQ ID NO:48—Partial protein sequence of TrzPhoR: Trz HAMP domain+Valine A/D fusion.

SEQ ID NO:49—Partial protein sequence of PhoR histidine kinase *Escherichia coli* sequence.

SEQ ID NO:50—Partial EnvZ protein sequence spanning fusion region.

SEQ ID NO:51—Partial Trg protein sequence spanning fusion region.

SEQ ID NO:52—Partial Trz protein sequence spanning fusion region.

SEQ ID NO:53—Partial PhoR protein sequence spanning fusion region.

SEQ ID NO:54—Partial protein sequence of coiled coil test construct Trg"CC"Pho.

SEQ ID NO:55—Partial protein sequence of coiled coil test construct TrzEnvZCC.

SEQ ID NO:56—Partial protein sequence of coiled coil test construct TrzEnvZcc2&3.

SEQ ID NO:57—Partial protein sequence of coiled coil test construct TrgPhoRcc3.

SEQ ID NO:58—Partial protein sequence of coiled coil test construct TrzHAMPPhoR fusion.

SEQ ID NO:59—Partial protein sequence of coiled coil test construct TrzHAMP+V PhoR.

SEQ ID NO:60—Partial protein sequence of coiled coil test construct TrzHAMP+VK.

SEQ ID NO:61—Partial protein sequence of coiled coil test construct TrgHAMP+V.

SEQ ID NO:62—Partial protein sequence of coiled coil D position mutants TrzHAMP+M.

SEQ ID NO:63—Partial protein sequence of coiled coil D position mutants TrzHAMP+V.

SEQ ID NO:64—Partial protein sequence of coiled coil D position mutants TrgHAMP+V.

SEQ ID NO:65—Partial protein sequence of coiled coil D position mutants TrgHAMP+G.

SEQ ID NO:66—Partial protein sequence of coiled coil D position mutants TrgHAMP+A.

SEQ ID NO:67—Partial protein sequence of coiled coil D position mutants TrgHAMP+L.

SEQ ID NO:68—Partial protein sequence of coiled coil D position mutants TrgHAMP+I.

SEQ ID NO:69—Partial protein sequence of coiled coil D position mutants TrgHAMP+E.

SEQ ID NO:70—Partial protein sequence of coiled coil D position mutants TrgHAMP+T.

SEQ ID NO:71—Partial protein sequence of EnvZ (SEQ ID NO:71) spanning the ADD residues (275-277) of EnvZ.

SEQ ID NO:72—Partial protein sequence of PhoR (SEQ ID NO:72) spanning the EGA residues corresponding to the ADD residues (275-277) of EnvZ.

SEQ ID NO:73—DNA coding sequence of MBP 6.1-5.

SEQ ID NO:74—DNA coding sequence for TAL transcription factor engineered to bind Gal4 binding sites.

SEQ ID NO:75—DNA coding sequence for Gal4VP64 codon optimized for *Arabidopsis*.

SEQ ID NO:76—DNA coding sequence for Firefly luciferase codon optimized for *Arabidopsis*.

DETAILED DESCRIPTION

The present disclosure provides novel receptor fusions with the histidine kinase PhoR for use in synthetic signaling systems with both high throughput systems (e.g., bacteria) and in plants. The source of the receptors may be other histidine kinase receptors such as those from pathogenic bacteria, e.g., the quorum sensing receptor RpfC. Because of the inventors' robust abilities with computational protein design, the receptor component can now be computationally designed. Alternatively, the receptors may be derived from chemoreceptor involved in periplasmic binding protein (PBPs) mediated chemotaxis such as Trg or Tar. Either the PBPs or the receptors have computationally re-designed binding pockets or are able to be entirely computationally redesigned, allowing the detection of novel, man-made substances in the environment and/or metabolic products of pathogens and/or metabolic products of biological organisms in general. The present disclosure also establishes the ability to convert nonfunctioning receptor histidine kinase fusions into functional fusions by manipulating a specific region of the histidine kinase, the CA interacting region. One application of the present disclosure is for use in detecting novel environmental signals using detector plants enabled with the present synthetic signaling system.

Plants, bacteria, and fungi can sense aspects of their environment through two-component or histidine kinase (HK) signal transduction systems that transmit information via protein to protein phosphoryl-transfer. Two component signal transduction systems respond to specific inputs such as the presence of ligands, osmotic conditions, oxidative conditions, or factors contributing to pathogenesis. The simplest two-component systems (TCS) use a plasma membrane localized histidine kinase and an intracellular response regulator (RR) protein. The RR functions to both receive the phosphoryl signal at an aspartate residue and initiate a transcriptional response upon becoming phosphorylated (FIG. 1A). More complex hybrid two component systems found in bacteria and plants involve additional components (FIG. 1B). TCS have been used in synthetic biology and biotechnology applications, primarily as components in synthetic signaling pathways.

Typically sensing of an environmental aspect through a TCS consists of three distinct phases, signal transmission, signal dependent kinase activation and signal transduction. In signal transmission a membrane localized receptor senses an environmental stimulus or binds to a molecular signal (ligand). The sensing event causes a conformational change in the receptor and the conformational change propagates across the membrane (trans-membrane signaling) to the cytoplasmically localized portion of the histidine kinase. Signal dependent kinase activation occurs when the receptor signal acts upon a distinct region of the histidine kinase causing a conformational change. The conformational change triggers a switch from a kinase "off" to a kinase "on" configuration of the HK. Activation of kinase activity results in autophosphorylation of a conserved Histidine residue. Signal transduction occurs when a RR interacts with the HK, resulting in a transfer of the phosphoryl group from the HK to the RR. The phosphorylated RR undergoes a conformational change which allows it to activate transcription of genes that will allow the plant, bacteria or fungus to respond to the environmental stimulus.

Figure 2:
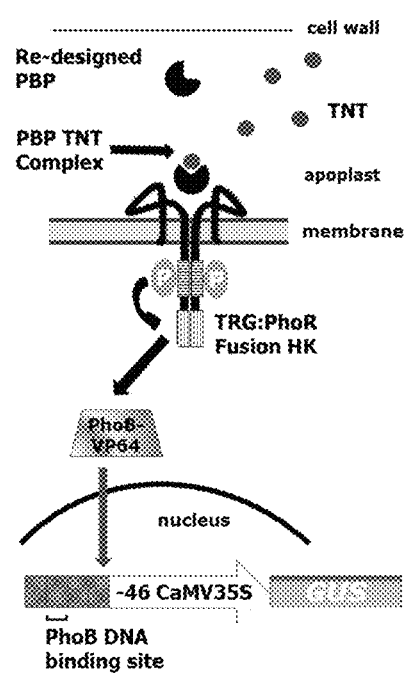
FIG. 2. Synthetic Signaling System Used In Detector Plants. In the apoplast, computationally re-designed PBPs bind TNT. The PBP-TNT complex interacts with a membrane-localized Trg-PhoR (DHP8) fusion, causing it to auto-phosphorylate and transfer the high energy phosphate to PhoB-VP64. PhoB-VP64 translocates to the nucleus and activates the PlantPho promoter.

The inventors previously described a synthetic two-component signaling system in plants based on bacterial derived histidine kinases and the bacterial RR PhoB (U.S. Pat. Nos. 8,148,605 and 9,062,320, both of which are incorporated herein by reference in their entirety). In this synthetic system, computationally designed receptors based on bacterial periplasmic binding proteins bind a substance of interest e.g., the explosive TNT. Periplasmic binding proteins (PBPs) are involved in binding of a wide variety of substances in gram negative bacteria. A subset of PBPs interact with the chemotactic receptors Trg, Tar, and Tap and initiate a signaling cascade (FIG. 1C) that allows the bacteria to respond to the presence of certain sugars (glucose, ribose, maltose, galactose) and amino acids (dipeptides, asp, glu, ser, ala and gly) by directing the cells to environments containing these nutrients. The ligand binding sites of ribose binding protein (RBP) and maltose binding protein (MBP) have been computationally re-designed to bind a variety of substances, among them a nerve toxin agent surrogate, the metal zinc and 2,4,6 trinitrotoluene (TNT) (Looger, et al., *Nature* 423:185-190, 2003; Feng, et al., *eLife* 4:e10606, 2015; Bick, et al., *eLife* 6; e28909, 2017; Strauch, et al., *Nat. Biotechnol.* 35:667-671, 2017). When a PBP binds its ligand a conformational change is produced, leading to increased affinity of the PBP-ligand complex for the extracellular domain of a bacterial chemotactic receptor, Trg in the case of RBP and Tar in the case of MBP. In this synthetic signaling system a chimeric fusion between the chemotactic receptor Trg with the cognate HK for PhoB, PhoR allows direction of the signal through PhoB. The inventors discovered that PhoB translocates to the plant's nucleus in a signal dependent manner. In this plant system PhoB has been modified to activate the transcription of plant genes (FIG. 2). In one aspect of the system, this synthetic two component signal transduction pathway activates a set of genes which breaks down chlorophyll (de-greening circuit). This results in the ability to produce a monitor or detector plant which de-greens specifically in the presence of a substance of interest. This synthetic signal transduction system allows one to artificially control biological input-output in plants as well as test, monitor and perfect components in bacteria.

The present disclosure exploits cells or plants' sensing mechanisms for extracellular signals, with the development of cells or plants that respond to a variety of biological, chemical, and environmental pollutants for substances of interest to produce a readily detectable response or phenotype. In a particular embodiment the plants disclosed herein lose green color when exposed to a specific substance; the degreening is an easily detectable biomarker and does not require sophisticated instrumentation. The modularity of the system allows a wide variety of responses, both visible and non-visible, to be produced in response to a detection event. These plants function as "sentinels" and are especially useful for widespread monitoring of substances in the environment whether interior or exterior.

For the plants to be useful as degreening biomarkers to detect specific chemical agents or to monitor environmental factors, an appropriate input circuit was produced. This input circuit is useful for linking detection to response. The modularity of the system allows a wide variety of responses, both visible and non-visible, to be produced in response to a detection event. When the input circuit is linked to the degreening circuit, a plant detector is produced. In addition, the ability to control response of plants and biological organisms to specific substances provides a useful tool for biotechnology allowing, for example, co-ordination of crop plants, facilitating harvesting and controlling other developmental, tissue or environmental responses.

The present disclosure provides a highly specific and sensitive method for cells or plants to detect a target substance of interest in their environment, transmit the sensing from outside the cell or plant to the nucleus, induce a specific transcriptional response and a type of output (for example controlled degreening) that provides detection to humans. In one embodiment of the present disclosure, the regulatory circuits have two components, referred to herein as input and output circuits. In another embodiment of the present disclosure, the input circuit has an ability to specifically recognize (bind) the target substance of interest and transmit a signal to the nucleus, where a specific response is initiated. The response can be a phenotypic and/or metabolic change of interest or a visible response to produce a plant sentinel. The modularity of the system allows a wide variety of responses, both visible and non-visible, to be produced in response to a detection event. In one embodiment of the present disclosure, one output circuit produces a degreening or other detectable phenotype in the transgenic plant containing the circuits. In one embodiment of the present disclosure the output circuit is also modular in that a variety of genes can be placed under control of the signal-inducible promoter. In one embodiment the input circuit is modular in that the receptor that is targeted to the extracellular space can be designed to provide specificity and selectivity for binding a given target substance of interest. One specific input circuit specifically exemplified herein provides detection of the explosive trinitrotoluene. One specific output circuit specifically exemplified herein serves as a simple and sensitive marker that can easily be recognized directly (visually), or by remote sensing and/or by monitoring changes in chlorophyll fluorescence, by changes in photosystem I and/or photosystem II, electron transport, by changes in hyperspectral imaging, and/or by changes in spectral properties. The modular nature of the system provides the ability to produce numerous types of responses or readouts including non-visible readouts that are detectable by webcam and high altitude platforms.

The input circuit comprises a sensor protein specifically targeted to the extracellular space of the cell or plant with a binding site specific for recognizing a target agent or a target substance of interest, a transmembrane histidine kinase protein, a nuclear shuttling protein, and a synthetically designed signal responsive promoter. Variations and elaborations described herein are found in various research publications, and known to those skilled in the art. One type of output circuit described herein activates the expression of one or more genes, which results in a degreening phenotype in transgenic plants containing the circuits.

The present disclosure provides a sensor protein or receptor at the cell surface, such that the sensor protein or receptor has a binding site specific for the target substance of interest. The transmembrane protein, a second component of the input circuit has three parts: an interacting domain, a transmembrane domain and a histidine kinase domain. Binding of the target substance of interest causes a conformational change in the sensor protein or receptor, so that it then binds to an interacting domain of the transmembrane protein on the exterior surface. The interaction of the sensor protein: target substance of interest complex results in activation of the histidine kinase, typically by an autophosphorylation mechanism. The interaction of the sensor protein or receptor with the interacting domain produces a conformational change in the transmembrane protein and/or transmembrane histidine kinase. The autophosphorylated histidine kinase domain of the transmembrane protein transfers a high energy phosphate group to a cytoplasmically located protein. A variety of proteins will function as shuttling proteins, including, but not limited to, a synthetically adapted shuttling protein such as PhoB:VP64, other shuttling proteins such as histidine phosphotransferases, *Arabidopsis* histidine phosphotransferase, and other natural proteins such as response regulators from plants, bacteria, fungi, and cyanobacteria systems, including adapted or synthetic proteins, or computationally designed proteins, that function in histidine kinase mediated signaling systems.

The shuttling protein typically has several functions including reception of the signal from the transmembrane protein, relay of this signal to the nucleus, or specific responding component, and/or activation of transcription. The protein may directly, or indirectly, bring about a cellular response. The typical cellular response is activation of transcription; however, other responses are possible including changes in membrane potential, cell expansion (in the case of engineering a response that would allow expansion of the xylem), or changes in the accumulation of a plant-derived product. At least some proteins are phosphorylated (directly) by the histidine kinase domain of the transmembrane protein. The phosphorylation of the proteins or protein components can cause an increase in binding affinity for a specific sequence of DNA as is the case for OmpR, or in the case of PhoB, allow a conformational change that removes repression, allowing the DNA binding domain to function. One type of response of this is a readout circuit that includes expression of the specifically regulated gene located in the nucleus of the plant and the production of a detectable phenotype, appearance or function of lack thereof or the readout can include activation of a gene controlling a trait of interest, for example, flowering or ripening.

The sensor protein or receptor can be derived from a bacterial (e.g., *Escherichia coli*) periplasmic binding protein (PBP), such as a maltose, ribose or galactose PBP, and the binding site for the target substance of interest can be a naturally occurring binding site or one that is the result of computational design. At the N-terminus there is also a signal peptide sequence for targeting the sensor protein to the exterior of the cell, plant or plant cell, such as, but not limited to, the signal peptide of the pollen PEX protein (Baumberger, et al., *Plant Physiol.* 131:1313-1326, 2003). Substances of interest can include, without limitation, plant hormones, explosives, chemical agents, products of industrial manufacturing, metabolites of biological organism(s), environmental pollutants including all currently listed environmental pollutants on the Environmental Protection Agency (EPA) superfund site, halogenated hydrocarbons, or degradation products, metal ions such as zinc, a heavy metal, a sugar, neurotransmitter, herbicides, pathogenic products, or an amino acid. The ability to computationally design the PBP, partially or entirely, expands this list of detectable substances to most molecules.

When the target substance of interest is bound to the sensor protein or receptor, there is an interaction with the protein that transmits a signal from the exterior of the plant to the interior of the plant by autophosphorylation and activation of the histidine kinase. Upon binding of the target substance of interest, there is an interaction between or within the sensor protein or receptor and the transmembrane protein (which contains the histidine kinase domain). This interaction causes autophosphorylation of a histidine residue located on the interior portion of the transmembrane protein. The phosphoryl group is then transferred (a mechanism called phosphor-relay or phosphotransfer) to a shuttling protein or transcription activator protein domain, allowing it to translocate to the nucleus or otherwise initiate a response. The phosphorylated protein, protein domain or secondary protein then binds a DNA recognition sequence present in a promoter of a gene (or genes) in the nucleus, which can be a genetically engineered gene, with the result that transcriptional expression of that gene occurs.

The transmembrane protein can be genetically engineered as a translational fusion consisting of plant and/or bacterial proteins, derived from one or more bacterial or plant proteins, derived from one or more proteins containing histidine kinase-like features, or synthetically synthesized features, or computationally designed features, provided that it functions in plants in conjunction with a protein or protein domain to transmit the signal to a response unit. The intracellular receptive protein or protein domain can be a plant protein, a bacterial protein or a synthetically designed protein, with the proviso that it receives the signal from the transmembrane protein. The receptive protein can either transmit the signal to another protein that initiates a response, or translocate to the nucleus in response to the signal. In one example, the signal receptive protein itself moves to the nucleus, binds DNA and activates gene expression. Specific examples include a plant histidine phosphotransferase or a bacterial protein such as the *E. coli* proteins OmpR or PhoB. Where the signal receptive protein is also a transcriptional activation protein, PhoB, the DNA recognition sequence is CTGTCATAYAYCTGTCACAYYN (SEQ ID NO:47), and it can occur from 2 to 12 times, for example 4 or 8 times in the region upstream of the transcription start site, and includes a plant transcriptional start site such as defined by a minimal transcriptional promoter.

The sequence that is expressed in response to detection of, or the presence of, a target substance of interest in the plant environment can be a protein coding sequence or it can be a functional nucleic acid sequence (such as a RNA interfering molecule, diRNA or an antisense RNA to inhibit synthesis of a related coding sequence) or it can be a combination of these. The associated expressed sequence can be a plant gene that is, in nature, expressed constitutively or in a tissue or condition specific fashion, but in the present disclosure, it is expressed when the target substance of interest or substance that binds to the sensing protein or sensing proteins is present or after the target substance of interest is present. The expressed sequence can be virtually any sequence of interest: a detectable marker such as green or yellow fluorescent protein or another fluorescent protein, β-glucuronidase or β-glucosidase, among others, a positive regulator of flowering or a sterility protein preferably selectively expressed in the appropriate tissue, a bioremediation coding sequence such as mercury reductase, a phytochelatin or metal sequestering protein, an enzyme for detoxifying a contaminant or harmful material, and the production of a specific nutritive or pharmaceutical substance, among others. The expressed sequence can also be a functional nucleic acid (antisense or diRNA to inhibit expression of a related nucleic acid sequence). There can be more than one target substance-regulated gene within a single cell or plant and more than one readout or response in a single cell or plant.

In an embodiment of the present disclosure, the sensing circuitry can be used to control features of interest, such as the timing of flowering of a plant or ripening of a fruit such that harvesting is more synchronized, coordination of crops such as cotton, soybean and corn and hence an ability to predict harvest time, and thus, make harvesting more efficient and economical or so that plants are in flower for a particular occasion. Such a gene or response unit is operably linked to a promoter containing the recognition sequence of the specific sensing system or systems. In another embodiment, the target substance of interest-dependent transcription regulatory system can be used to render plants exposed to the target substance sterile, when a sterility inducing protein is expressed under the regulatory control of the control system of the present disclosure.

Within the scope of the present disclosure are one or more DNA constructs containing a plant operable sensor protein as described above, a plant transmembrane protein, a plant operable signal reception and/or transcription activation protein that is activated by the histidine kinase portion of the sensing circuit (via an intermediary endogenous protein, or directly by the membrane bound kinase), and a plant operable sequence operably linked to transcription regulatory sequences, which include the recognition sequence of the particular transcription activating protein of the disclosure. Similarly, the present disclosure provides transgenic plant cells, transgenic plant parts, transgenic plant tissue and transgenic plants containing one or more constructs of the present disclosure.

The present disclosure provides transgenic (sentinel) plants useful for environmental monitoring and for detecting particular biological and chemical agents, environmental pollutants, and/or a specific substance such as herbicides or trigger compounds. Trigger compounds are substances that bind to the natural or computationally designed sensor proteins and thereby increase the sensor proteins affinity for an extracellular protein domain (for example Trg). In a specific embodiment, the plants disclosed herein lose green color within hours of exposure to particular target biological/chemical agents or environmental pollutants. The loss of green color (or a change in the fluorescence of chlorophyll or a change in photosynthetic electron transport, or other types of responses) in plants are easily detectable, either by direct observation, with simple hand-held machines, or remotely by aircraft, satellite, or other varieties of sensors, including webcams and high altitude platforms. The sentinel plants of the present disclosure comprise genetically engineered DNA constructs that direct the expression of both the input and output circuits, as described herein, with the result that the plants lose color, or otherwise respond, when they "sense" the presence of the target substance of interest. An important advantage of the degreening system in these sentinel plants is that they are capable of regreening. They either regreen naturally or at an enhanced rate with treatment of hormones, i.e., the sentinels can be reset for renewed surveillance for the target substance to which they respond. In one aspect of the present disclosure a transgenic plant wherein degreening has occurred due to the presence of a target substance of interest is able to regreen after removal of the external target substance of interest. Other responses or readouts allow rapid response time or ability to detect signals remotely with webcams or high altitude platforms.

The transgenic plants (sentinel plants) of the present disclosure can be indoor plants, for example, any of a number of species that are commonly used as decorative accent plants, such as peace lily (Spathiphyllum), philodendron, pothos (Epipremnum), spider plant (Chlorophytum), Tradescantia and Dracaena, and the like. In addition, the sentinel plants can be crop plants such as corn, wheat, soy, cotton, soybeans and others, or they can be grasses or trees, either deciduous (poplars, aspens, maple, oak, cottonwood, and the like) or evergreen (pines, spruce, junipers and the like) or they can be annuals or perennials used in various types of plantings, or they can be a variety of native species, or they can be aquatic plants including, but not limited to, algae. Nearly all plants and/or plant cells can be readily transformed and transformed seed directly formed or plants produced from the transformed cells, as is well known to the art. The sentinel plants of the present disclosure can provide a warning of current presence of a target substance of interest or they can provide notice to responders to a scene to allow for appropriate protective measures and/or to prevent exposure to a dangerous condition. In addition, the sentinel plants provide the ability to remotely monitor for the presence of substances. Moreover, the sentinel plants allow for continuous environmental monitoring over extremely large scales (e.g., hundreds or thousands of square kilometers) that is not currently possible with any other publicly known method.

The sentinel plants of the present disclosure contain a genetically engineered signaling pathway consisting of two functional parts referred to herein as "input" and "output" wherein one embodiment of the output is the "degreening" circuit". The input gene circuit is a natural or genetically engineered system, or computationally designed system, that recognizes a biological or chemical agent, explosive, or an environmental pollutant or target substance of interest specifically and selectively, then activates an output gene circuit that results in the desired response. In the case of a plant sentinel, one example of an output gene circuit is the degreening circuit, so that the degreening phenotype i.e., white plants, are produced in response to an agent or pollutant. The degreening can be visually detected as a loss of green color or it can be detected as a change in chlorophyll fluorescence or in photosynthetic electron transport or it can be detected with a variety of spectroscopic methods such as hyper-spectral imaging and other methods. Other responses or readouts allow rapid response time or ability to detect signals remotely with webcams or high altitude platforms.

The output and input circuits of the present disclosure are generated by expressing DNA constructs specifically designed to provide a functional system. Examples of methodologies well-known to people in the field include CRISPR-Cas9 methods, where the endogenous genes can be changed to produce plants with these properties. The input circuit is a system comprising a receptor or a binding protein designed to recognize (e.g., by binding) a signal (e.g., analyte or ligand), and this binding event ultimately activates a response, one of which is transcription of a gene of the output (degreening) circuit to produce a plant sentinel. Thus, the specificity and selectivity of a given response is determined by the input circuit. An example of the input circuit is a receptor or binding protein (sensor protein) that specifically binds a particular explosive, chemical agent or a pollutant, or pathogen or pathogen product, the target substance of interest, which, upon binding of such explosive, agent or pollutant, or pathogen or pathogen product, can transmit a signal via the transmembrane protein to activate transcription of a gene(s) in the output circuit. As specifically exemplified the sensor protein:target substance complex interacts with the exterior domain of the transmembrane protein, with the result that the histidine kinase becomes active.

In one method, the response system (output, as exemplified by degreening) circuit is generated by transforming a plant with DNA constructs (i.e., expression vectors) comprising one or more nucleic acids encoding, or complementary to, a nucleic acid encoding key enzymes or functional fragments thereof in chlorophyll biosynthesis and/or degradation pathway under the control of a promoter that responds to a signal from the input circuit. The term "functional fragment" as used herein, is intended to indicate that the product (i.e., enzyme) can be a truncated protein as long as it retains its enzymatic activity to cause degreening (chlorophyll degradation). One skilled in the art would know that a truncated protein may be able to maintain enzyme activity. Examples of chlorophyll degradation enzymes include, but are not limited to, RCCR, PaO and chlorophyllase. The output/degreening circuit can also comprises a target-substance-regulated inhibition of chlorophyll biosynthesis. As specifically exemplified, this is achieved by expression of either antisense, or preferably, interfering RNA molecule (such as diRNA, siRNA) sequences specific to a coding sequence for an enzyme in the chlorophyll biosynthetic pathway. These interfering RNA molecules are examples of functional nucleic acids, and in the context of inhibition of gene expression, a functional fragment of a coding sequence or gene is one that specifically interacts with a transcript of the coding sequence or gene so as to reduce expression of the product of that gene or coding sequence. Examples of the enzymes involved in chlorophyll biosynthesis include, but are not limited to, protochlorophyllide oxidoreductase (POR), GUN4, other GUN genes (genome uncoupling), Mg chelatase and chlorophyll synthetase. It is understood that other targets in the chlorophyll synthesis or degradation pathway can be substituted for those specifically set forth. It is further understood that the input system allows a wide variety of outputs, responses or readouts, as long as the output, response or readout is operationally linked to the input. These include rapid response time or ability to detect signals remotely with webcams or high altitude platforms.

The DNA construct for transforming the readout or degreening gene circuit into a plant or plant cell typically contains a nucleic acid encoding at least one chlorophyll degradation enzyme (or a fragment thereof that functions to effect chlorophyll degradation) and/or desirably also a nucleic acid whose expression product inhibits chlorophyll synthesis operably linked to a promoter with transcription regulatory sequences that bind a transcription activator protein that receives the signal from the input gene circuit. Typically it can be a transcriptional activator protein that solely receives the signal from the transmembrane histidine kinase and shuttles to the nucleus or a nuclear localized transcriptional activator protein that receives the signal from the transmission protein that relays the signal from the transmembrane histidine kinase and shuttles to the nucleus. The exterior component of the transmembrane histidine kinase has bound the sensor protein substance complex therefore relaying an input signal generated by an explosive, a chemical or biological agent, a pollutant, a pathogen or pathogen product, or a specific substance. In response to the input signal, this dual modulation, i.e., inhibition of synthesis and stimulation of degradation of chlorophyll ensures loss of green color in plants when exposed to a variety of chemical agents or environmental pollutants. As described herein, chlorophyll synthesis can be inhibited by producing interfering RNA or antisense RNA derived from at least one of the genes encoding chlorophyll synthetic enzymes.

Accordingly, a transgenic plant containing the input and output circuits disclosed herein loses its green color when exposed to a substance in the environment that activates the input circuit by binding to a specific receptor site (i.e., sensor protein) outside the plant. The substance can be, for example, a chemical agent, mercury, lead, arsenic, uranium, cadmium, selenium, polycyclic aromatic hydrocarbon, a benzene, a toluene, a xylene, or a halogenated (chloro, fluoro, and chlorofluoro) hydrocarbon, a by-product of industrial manufacturing, a metabolite of biological organisms, explosives, any substance listed on the EPA superfund website, specific compounds involved in manufacture of compounds of interest, a pathogen or pathogen product, or a trigger substance to bring about a desired change in the plant or crop. It is also possible to wire the genetic circuitry to enable detection of multiple substances. In addition, the target substance that binds to a specifically engineered sensor protein and input circuit via the extracellular receptor could be an explosive such as trinitrotoluene, other types of explosives, or a degradation product of one of the foregoing compounds specifically bound by the sensor protein, including computationally designed sensor proteins.

The sensing and response system of this disclosure is modular in that it can be coupled with a variety of input circuits (sensor proteins) to provide specificity and selectivity for a particular chemical agent and/or other environmental factor of interest that is recognized by an available sensor protein that effectively interacts with the exterior domain of the transmembrane protein when the target substance is bound. Likewise, the input circuits can be combined with Logic Gates (e.g., AND, OR, NOT gates organized, for example, as detect substance "a" AND detect substance "b"; detect substance "a" OR substance "b"; detect substance "a" OR substance "b" but NOT substance "c," etc.) to further increase the present technology's uses. Similarly, the readout gene that is expressed via the histidine kinase system or systems of this disclosure can be selected for a desired result, with the proviso that it is operably linked to a promoter and associated control sequences that interact positively with a transcription regulatory protein activated directly or indirectly by the histidine kinase and/or PhoB or OmpR, described herein. Specifically, receptors that are engineered to bind site specifically to the target substance of interest (including but not limited to heavy metals, chemical agents, explosives and certain degradation products thereof, environmental pollutants such as MTBE, herbicides such as glyphosate and the like. The sensing circuit further includes the transmembrane protein with an external binding domain that interacts with the sensing protein-target substance complex and an intracellular portion which directs the phosphorylation of a transcriptional activator protein, as specifically exemplified by PhoB and/or modified and/or an adapted version of the PhoB protein. PhoB can also be phosphorylated by an endogenous plant histidine phosphotransferase. The phosphorylated PhoB (activated form) then binds to the PhoB cognate binding sequences which are part of the synthetic promoter operably liked to a chlorophyll degradation enzyme coding sequence (such as chlorophyllase). The transcriptional activator protein can also be a hybrid protein including, but not limited to, PhoB:VP64 translational fusion protein and it is expressed in a transgenic plant expressing its coding sequence operably linked to a plant expressible promoter, which can be constitutive or which can include sequences for tissue-specific or condition-specific expression. The activator protein can be any eukaryotic transcriptional activator including, but not limited to, VP16, VP64 and GAL4. The signal-dependent nuclear translocating PhoB protein could also be fused to synthetic repressors, including LexA-EAR (LEAR) or Gal4-EAR (GEAR) (U.S. Patent Application Publication Number 2018/0105825), or OfpX (Wang, et al., *PLoS One* 6:e23896, 2011).

Histidine Kinase Signal Transduction System

Two component histidine kinase signal transduction systems are conserved between plants and bacteria, and this conservation was the basis of forming a functional input (sensing) circuit. In bacteria, sensitive chemotactic sensors exist to direct motile bacteria to nutrients, e.g., ribose. When a periplasmic binding protein such as the ribose binding protein binds its ligand, it develops a high affinity for the extracellular domain of bacterial chemotactic receptors such as Trg. Upon binding of the ligand/binding protein complex, a cytoplasmic histidine kinase is activated. Normally in the bacterium, this results in chemotaxis toward the food source. Hybrid histidine kinases have been expressed in bacteria where the cell surface PBP binding domain of Trg has been combined with the interior histidine kinase domain from proteins such as EnvZ. This hybrid protein activates transcription via phosphorylated transcription activator proteins. In the hybrid histidine kinases, the target substance is bound by the sensor protein, and the substance:protein complex binds to the interacting domain of the hybrid histidine kinase at the exterior side of the cell membrane, and that initiates activation of the histidine kinase (HK). The HK starts a phospho-relay (phosphorylation relay) through a bacteria response regulator (e.g., OmpR or PhoB) to activate transcription of bacterial genes. The phospho-relay always goes His→Asp→His, etc. In addition, at least some transcription activator proteins are phosphorylated (activated) by that same kinase domain.

Chemotactic binding proteins (periplasmic binding proteins) have been redesigned using computer-run computational design methods so that instead of binding substances such as ribose or galactose or maltose, the engineered proteins specifically bind a target substance of interest such as TNT, chemical agents, heavy metals, or other environmental pollutants or harmful substances.

Plants also use a two-component or histidine kinase signaling system that responds to cytokinin (a plant hormone). Plant signal transduction is more complex. The histidine kinases are "hybrid types". The plant HKs in *Arabidopsis* are known as AHKs. Upon sensing cytokinin, plant HKs phosphorylate an internal histidine kinase and initiate a phospho-relay internally to an aspartate residue located in the receiver domain of the same protein. The receiver domain transfers the phosphate group to an independent protein. The independent protein moves into the plant cell nucleus upon phosphorylation and then transfers the phosphate group to a nuclear localized protein, ARR Type B, transcription factors that then initiate transcription of ARR Type A genes. Examples of ARR type A genes useful in the present disclosure include, but are not limited to, ARR5 and ARR7, or any Type A ARR gene. Other functionally equivalent sequences may also be used in the systems described herein.

Computer design enables the design of sensor proteins to bind with great specificity and sensitivity, a variety of compounds or substances. In bacteria, the engineered receptors were targeted to the periplasmic space to sense various substances of interest. In plant cells, it is necessary to add (desirably at the N-terminus) a secretory sequence functional in plant cells so that the sensor protein is at the exterior of the cell and can bind the particular target substance of interest and it is necessary to delete the bacterial periplasmic targeting leader. The starting point is the engineered periplasmic binding protein, and the ending point is a detectable change resulting from a transcriptional response in the nucleus; computer-designed sensor proteins and molecular biological techniques allows for the combination. Hybrids at both the starting point and ending point allowed functional signaling.

To obtain information from outside the plant cell and transmit a signal to the nucleus of the plant cell, specifically engineered target sensing receptors were positioned outside of plant cells. Receptors that have been computationally designed include, but are not limited to, the periplasmic binding proteins RBP, MBP (maltose binding protein) and GBP (galactose binding protein). Importantly, at least in part because the system is modular, PCR or DNA synthesis can be used to change the receptor/sensor protein portion from a receptor/sensor protein specific for TNT to a target substance of interest (explosives, chemical agents, zinc, heavy metal, environmental pollutant).

Plant Extracellular Space

Plants are not known to have a functional periplasmic space. However, evidence indicates that there is a functional space between the plant plasma membrane and the outside. Small proteins can freely move and/or diffuse in the plant cell wall, better understood as a complex matrix, and even move and/or diffuse in the plant cuticle, the waxy coating that is found outside some plant organs. In bacteria, the periplasmic binding protein contains a leader peptide portion that targets the protein to the periplasm. In plants, proteins are targeted to the extra-cellular space by way of the endoplasmic reticulum. Because of the different targeting mechanisms, a plant extracellular targeting sequence is needed and the bacterial periplasmic targeting leader must be removed.

Genetically Engineered Plants Capable of Losing Green Color

The present disclosure also provides genetically engineered plants capable of losing green color in response to a signal (analyte or ligand) by simultaneously controlling expression of genes involved in chlorophyll biosynthesis and/or degradation. These plants are capable of receiving input from cytoplasmic and extracellular analytes and linking these components to the degreening circuit resulting in the loss of green color. Thus, the plants of this disclosure serve as a simple and easily detectable biomarker for adverse environmental input.

The degreening circuit is assembled in a "plug and play" manner. Hence, the sensor protein for TNT, which initiates the input, can be replaced by a different computationally designed sensor protein allowing the degreening circuit to respond to a specific target substance or target substances of interest. The model plant species *Arabidopsis*, which allows rapid optimization of the degreening circuit and its response, can be used in the presently disclosed compositions and methods. However, the circuits described herein are readily introduced into other plant species such as those typical of shopping malls, office buildings, landscapes, forested areas, cropland or aquatic systems.

The plants of this disclosure that lose their green color in response to a target substance can serve as untiring sentinels reporting on adverse input from the environment (e.g., chemical weapons or pollutants). Plant sentinels would be unthreatening to the general public and can be deployed in shopping malls and office buildings and at special events where most people can recognize a loss of green color and security personnel could easily detect the changes within a short period with inexpensive hand-held machines. In addition, loss of green color or other disruption of chlorophyll, such as chlorophyll fluorescence, or photosystem electron transport or hyper-spectral imaging can be rapidly quantified by authorities with either portable hand-held equipment or simple laboratory equipment (spectrophotometers). In vast geographic areas, detector systems could be introduced into plants typical for landscapes and aquatic systems, allowing satellites to identify adverse environments.

The degreening circuit of the present disclosure induces genes that are involved in chlorophyll breakdown and synthetic genes for inhibiting chlorophyll synthesis. Simultaneous expression of the genes that initiate chlorophyll breakdown and inhibit new chlorophyll biosynthesis would yield the most efficient degreening phenotype. For this reason, the degreening circuit can be created using three genes, two in the chlorophyll degradation pathway and one inhibitory gene in the chlorophyll biosynthesis pathway. A person of ordinary skill in the art understands that other combinations of the genes that are known to be involved in chlorophyll synthesis and degradation can be used to obtain the degreening phenotype demonstrated herein. In addition, a person of ordinary skill in the art understands that the reactive oxygen species (ROS) generated in the chloroplast could be used to initiate and generate the degreening within plastids.

The degreening circuit of the present disclosure can respond in two different ways; it can respond to target substances within the cytoplasm as well as those that are extracellular. To test the ability of the degreening circuit to function with cytoplasmic input in plants, a synthetic cytoplasmic receptor is linked to the circuit. In response to binding an analyte, the cytoplasmic receptor is transported to the nucleus where it activates synthetic transcriptional promoter(s) fused to genes whose products degrade chlorophyll while preventing new chlorophyll biosynthesis. To test the ability of the degreening circuit to function with input from outside the plant, an input circuit containing a chimeric receptor or binding protein can be linked to the degreening circuit. In response to binding an analyte, the extracellular receptor initiates a signal transduction pathway and activates a signal receptive synthetic transcriptional promoter fused to genes whose products degrade chlorophyll while preventing new chlorophyll biosynthesis.

Normal time periods for notable loss of green color in plants varies widely from days to weeks depending on whether the loss is triggered from environmental changes, development (e.g., flower petals) or stress (e.g., pathogens). To develop a system that can lose green color rapidly in response to a signal, both the chlorophyll biosynthesis and chlorophyll breakdown pathways were modified to construct a "degreening circuit". In addition to genes involved in chlorophyll metabolism, a redundant marker, green fluorescent protein (GFP) can be included in the degreening circuit as a control. The GFP marker is similarly (optionally) linked to the input part of the circuit and serves to eliminate false positives that might arise.

To ensure that the degreening phenotype appears rapidly, two genes (for example, chlorophyllase and RCCR) were used in the degreening circuit exemplified herein. Although it was not measured, the turnover in chlorophyll is strongly believed to have stimulated feedback induction of new chlorophyll biosynthesis. To prevent this from occurring in the degreening circuit, expression of the protochlorophyllide oxidoreductase (POR) gene, the rate-limiting enzyme in chlorophyll biosynthesis, was inhibited.

One approach to prevent expression of (silence) a specific gene involves the production of an interfering RNA molecule that contains a sequence identical to the gene of interest. Typically, the plants are genetically engineered to express inverted repeats (500-700 bp) to the gene of interest. The resulting double-stranded RNA is homologous to an endogenous transcript. Transgenic plants containing diRNA show high turnover rates of the homologous transcript and complete silencing of the endogenous gene expression. An interfering RNA molecule has been shown to be more efficient than antisense RNA in blocking the expression of a desired gene with silencing frequency between 90-100%. Thus the initial degreening circuit was generated using double stranded RNAs to silence the POR gene in a transgenic plant and hence prevent the de novo synthesis of chlorophyll after input from an analyte. A series of convenient *Arabidopsis* vectors for making dsRNA constructs are publicly available. These vectors contain a cassette for cloning a desired gene or gene portion in the sense and antisense orientations. The cassette has two pairs of unique restriction enzyme recognition sites flanking a 335 base pair GUS (β-glucuronidase) fragment that separates sense and antisense regions of the inverted repeat and facilitates formation of the dsRNA. The vectors are a series of plasmids that replicate in both *E. coli* and *Agrobacterium tumefaciens* allowing easy cloning and plant transformation, respectively. Vectors are available carrying the Bar or NptII genes, the plants containing the introduced genes can be selected with the herbicide BASTA (glufosinate ammonium) or the antibiotic kanamycin, respectively. A chloamphenicol or spectinomycin gene provides bacterial selection. For example, the conserved region of protochlorophyllide oxidoreductase (POR) gene can be cloned in the sense and antisense direction to produce the diRNA molecule specific for the POR genes. The vectors are designed to direct expression of the diRNA molecule with a strong constitutive promoter (CaMV 35S). To place the diRNA vector in the degreening circuit, this promoter, which is flanked with unique restriction sites, is replaced with promoters that place expression under control of perception of cytoplasmic or extracellular analytes for example, using the Pho promoter described.

Assembly and Testing of Degreening Gene Circuits

In many biological responses, sensing of a specific substance leads to a transcriptional response. The synthetic sensing system for plant sentinels links input to transcriptional output, hence, a test readout system was created that is triggered by a transcriptional response (signal-regulated induction of gene expression). Numerous transcriptional induction systems are available that provide a model in which to test the chlorophyll reporter system. A synthetically designed, steroid inducible system was modified to function in plants. In the presence of a synthetic steroid (4-hydroxytamoxifen, 4-OHT), a chimeric transcriptional regulator relocates to the nucleus and induces expression of a promoter made up of specific response elements and the −46 region of the CaMV35S promoter, designated 10XN1P. The 4-OHT induction system is essentially analogous to other transcriptional inducible systems.

In order to use plants to monitor large areas for pollution or terrorist agents, a reporter or readout system is needed. Prior gene reporter systems were developed for laboratory use and do not provide characteristics needed for a plant sentinel. A synthetic degreening circuit was developed that allows the green pigment chlorophyll to be used as a biosensor readout system. Induction of the degreening circuit allows remote detection, displays a rapid response, provides a reset capacity, and results in a phenotype readily recognized by the general public. Because the degreening circuit produces a white phenotype, it is easy to distinguish it from plants stressed from biotic or abiotic conditions, which produce yellow (or other color) phenotypes via senescence-related pathways. The inability to reset biosensors has been the major limitation to their use. The degreening circuit provides a simple capacity to be reset. Plants regreened after removal of the inducer, and this regreening was enhanced by a brief cytokinin treatment. Because the transcriptional inducer used (4-OHT) is relatively stable, the degreening circuit may not fully switch to an "off" position immediately following removal of the inducer, and the regreening process may not start until the inducer within the plant degrades. Hence, it should be possible to substantially reduce the time needed for regreening, currently about 3 days.

The degreening circuit, combining "stop-synthesis" with an "initiate breakdown" function, caused loss of chlorophyll with unprecedented speed. When each function was introduced separately, plants did not visibly degreen in the 48 hour timeframe except in the cotyledons. Expression of the "initiate degradation" circuits (CHLASE and PAO, or CHLASE and RCCR) failed to produce rapid degreening, suggesting that plants can enhance chlorophyll biosynthesis when needed. Likewise, the "stop synthesis" circuits (diRNA specific to POR or GUN4) failed to produce rapid degreening, supporting the concept of a large amount of metabolically stable chlorophyll within the plant. The rational combination of these two functions in one T-DNA construct produced a synthetic "degreening circuit". The designed gene circuit is successful with respect to signal responsiveness, as indicated by three types of data: response of excised leaves to dark-induced senescence, distinctive ultrastructural changes, and microarray data showing a difference in genes regulated by the degreening circuit and normal chlorophyll loss in senescence.

Light was shown to be important for the rapid degreening process to occur, as induced plants incubated in the dark failed to turn white, even after 72 hours of induction. When induced plants were transferred to light, degreening proceeded at an enhanced rate. These results suggest that the degreening circuit is poised to respond in darkness, but not able to initiate rapid degreening without light. Chlorophyll biosynthesis and breakdown intermediates are potentially phototoxic. Because the degreening circuit interferes with the normal balance of chlorophyll and likely its metabolic intermediates, it is possible that, upon light exposure, these molecules cause photo-oxidation of pigments. A similar light requirement for degreening was observed for detached leaves. Under standard light conditions degreening induction caused detached leaves to fully degreen within 48 hours. However, darkness failed to induce full degreening in detached leaves, even after 72 hours of induction. Because darkness has been shown to induce senescence in *Arabidopsis* detached leaves, these results suggest that chlorophyll loss from the degreening circuit is distinct from senescence.

The degreening circuit provides an effective means to control chlorophyll levels in plants. The trigger for the degreening circuit is a specific input, resulting from sensing of the binding of a target substance of interest outside the plant, with signal transduction via histidine kinase within the cell and nuclear transcription activation. The steroid-inducible 10XN1P promoter used with the degreening circuit as a model can be replaced with other promoter elements, such as those responsive to signal transduction or the synthetic PlantPho promoter, as readily understood in the art. By combining the controlled chlorophyll loss as a reporting element with a sensing system such as computationally designed receptors or sensor proteins that provide input via transmembrane histidine kinases, plants are produced to serve as inexpensive monitors for terrorist agents, environmental pollutants or other target substances of interest. Degreening indicating presence of the target substance can be observed visually at close range or detected from a distance by remote sensing, as known to the art.

All DNA constructs, transgenic plant cells, tissue and plants, and methods for detecting a target substance of interest or for obtaining gene expression in response to the presence of the target substance of interest are within the scope of the present disclosure. It is further understood that other evolutionarily conserved signal transduction components and systems, and transcription regulatory components can be substituted for those recited herein, provided that there are functional input and/or output circuits responsive to the presence of a target substance.

Definitions

In general the terms and phrases used herein have their art-recognized meaning, which can be found by reference to standard texts, journal references and contexts known to those skilled in the art. The following definitions are provided to clarify their specific use in the context of the present disclosure.

The term "transgenic plant" is used herein to indicate a plant, or photosynthetic organism including algae, that has been genetically modified to contain exogenous or heterologous DNA to obtain a desired phenotype. Examples of the exogenous DNA molecules that have been transformed into the plants of the present disclosure include those encoding segments of DNA encoding the sensor protein, the transmembrane protein, a shuttling and/or response protein, and a receptive promoter, collectively known as the response circuits and/or those encoding segments of chlorophyll biosynthetic and/or complete degradation enzymes and a promoter that is responsive to a signal.

The term, "plant," as used in the present disclosure, is intended to cover any plant, vascular or nonvascular, aquatic or terrestrial; algae, and organisms formally and informally recognized as algae now more properly known as cyanobacteria are included within this definition.

The term "non-plant organism" includes, but is not limited to, Archea, bacteria, fungi including yeast and cyanobacteria and the like and other organisms containing two-component signaling systems.

The term "degreening," also referred to as a "loss of green color," is intended to indicate a loss of chlorophyll and photosynthetic pigments in the transgenic plants that is distinguishable from normal plants (non-transgenic plants). The degreening can be detected visibly, or with a variety of instruments that measure properties including, but not limited to, chlorophyll fluorescence, hyper-spectral imaging, infra-red and near-infra-red imaging, multi-spectral imaging, photosynthetic properties and properties related to reactive oxygen species and their damage. The measurement instruments can be hand-held, or instruments that function at a distance, the distance being from aircraft or satellites.

The term "external signal," or "environmental signal," or "target substance of interest," is intended to mean a signal typically in the form of an analyte or ligand that triggers the signaling pathway in the transgenic plants of the present disclosure and results in the degreening phenotype and/or a change such as induction of gene expression of interest. In this sense, the signal can be any biological or chemical agent including environmental pollutants. The substance can be, for example, sugars, herbicides, a poison, a pollutant, a toxin, heavy metals such as mercury, lead, arsenic, uranium, cadmium, selenium, polycyclic aromatic hydrocarbon, a benzene, a toluene, a xylene, or a halogenated (chloro, fluoro, and chlorofluoro) hydrocarbon, a steroid or other hormone. In addition, the target substance that binds to a specifically engineered input circuit via the extracellular receptor could be an explosive such as TNT (trinitrotoluene) or other explosive, or a degradation product of one of the foregoing compounds recognized by the input circuit via specific receptor site binding by the sensor protein. Any target substance for which a sensor protein can be computationally designed (Looger, et al., *Nature* 423:185-190, 2003; Dwyer, et al., *Curr. Opin. Struct. Biol.* 14:495-504, 2004) can serve as an external signal in the context of the present disclosure.

The term "detectable marker" is a change brought about in a plant that is perceivable or capable of being sensed by humans, other organisms such as, but not limited to, dogs, and/or machines. The change can be visible or invisible to humans. The sensing can involve non-destructive (for example, multi-spectral imaging) or destructive methods (for example, analysis of protein, DNA, RNA or metabolic product).

The term "response regulator domain" is a protein or portion of a protein that contains conserved amino acids collectively functioning to perceive a phosphor-relay from an activated histidine kinase. The conserved domain may contain a phosphor-accepting Asp or His residue, or it may contain other residues that can be made capable of accepting the activated phosphate.

The term "response gene" is a gene whose expression is linked to input from the sensor protein or proteins.

The term "sensor protein" is used interchangeably with "receptor."

The term "transmembrane protein" is used interchangeably with "histidine kinase".

The terms "expression construct" or "DNA construct" are used interchangeably herein and indicate a DNA construct comprising particular sequences necessary for transcription of an associated downstream sequence. An expression vector is a plasmid containing an expression construct. If appropriate and desired for the associated sequence, the term expression also encompasses translation (protein synthesis) of the transcribed RNA. The particular sequences contained in the expression vector include a promoter, enhancer, termination signal, transcriptional block and the like. To prevent transcriptional interference from multiple transgenes, a transcriptional block can be placed between appropriate genes on a plant transformation plasmid. A promoter is a DNA region that includes sequences sufficient to cause transcription of an associated (downstream) sequence. The promoter may be regulated, i.e., not constitutively acting to cause transcription of the associated sequence. If inducible, there are sequences present therein that mediate regulation of expression so that the associated sequence is transcribed only when an inducer molecule is present. In the present context, the inducer molecule is analogous to the signal transmitted by an input circuit.

The term "derived from" includes genes, nucleic acids, and proteins when they include fragments or elements assembled in such a way that they produce a functional unit. The fragments or elements can be assembled from multiple organisms provided that they retain evolutionarily conserved function. Elements or domains could be assembled from various organisms and/or synthesized partially or entirely, provided that they retain evolutionarily conserved function, elements or domains. In some cases the derivation could include changes so that the codons are optimized for expression in a particular organism.

"Expression control sequences" are DNA sequences involved in any way in the control of transcription or translation. Suitable expression control sequences and methods of making and using them are well-known in the art. The expression control sequences must include a promoter. The promoter may be any DNA sequence that shows transcriptional activity in the chosen organism, plant cells, plant parts, or plants. The promoter may be inducible or constitutive. It may be naturally-occurring, may be composed of portions of various naturally-occurring promoters, or may be partially or totally synthetic. Also, the location of the promoter relative to the transcription start may be optimized. Many suitable promoters for use in plants are well-known in the art as are nucleotide sequences that enhance expression of an associated expressible sequence.

The term "RNA interfering molecule" includes, but is not limited to, diRNA, siRNA miRNA, or an antisense RNA to inhibit synthesis of a related coding sequence. It is part of a mechanism for RNA-guided regulation of gene expression in which double-stranded ribonucleic acid (RNA) inhibits the expression of genes with complementary nucleotide sequences.

The DNA constructs of the present disclosure can be used to transform any type of cell, plant or plant cell. A genetic marker can be used for selecting transformed cells ("a selection marker"). Selection markers typically allow transformed cells to be recovered by negative selection (i.e., inhibiting growth of cells that do not contain the selection marker) or by screening for a product encoded by the selection marker.

EXAMPLES

The following examples are included to demonstrate preferred embodiments of the present disclosure. It should be appreciated by those of skill in the art that the techniques disclosed in the examples, which follow represent techniques discovered by the inventors to function well in the practice of the present disclosure, and thus can be considered to constitute preferred modes for its practice. However, those of skill in the art should, in light of the present disclosure, appreciate that many changes can be made in the specific embodiments, which are disclosed and still obtain a like or similar result without departing from the spirit and scope of the present disclosure.

Example 1: Using the N-Terminal End of the Signal Dependent Histidine Kinase Activation Region to Engineer Novel Receptor Histidine Kinase Fusions Most of the reported functional chimeric receptor/HK fusions utilize a common signaling domain, the HAMP domain, which is found in chemotactic receptors and some HKs. The first reported chimeric receptor/HK fusion was made by fusing a chemotactic receptor Tar to the HK EnvZ at the shared HAMP domain. However, there are a large number of receptors and HKs that lack a HAMP domain. PhoR lacks a HAMP domain which made determining a functional fusion point (functional=off in the absence of ligand and on in presence of the ligand) with previous knowledge and technology difficult. Previous fusions of Trg to PhoR showed a high basal activity (kinase on) in the absence of signaling.

Figure 3A:
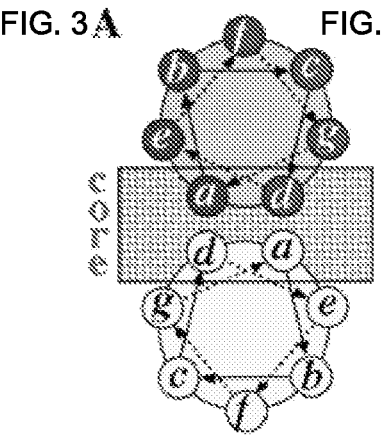
FIG. 3A, FIG. 3B and FIG. 3C. Interaction between the two α-helices in the tropomyosin coiled-coil. Each α-helix is shown with seven residues (a-g) in two turns.
Figure 3B:
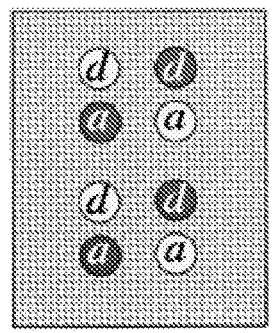
Figure 3C:
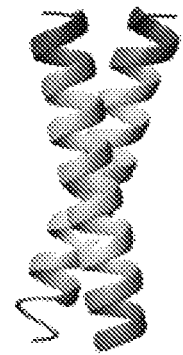

A computational learning algorithm can be used to show a protein structural feature, a coiled-coil like element, in the dimerization and histidine phosphorylation (DHP) domain of HKs (Singh, et al., *Proc. Natl. Acad. Sci. USA* 95:2738-2743). As diagramed in FIG. 3, coiled-coils result from protein-protein interactions between 2 or more alpha helices somewhat resembling the coiled strands in a springs. There are seven amino acids per coiled coil alpha helix and the amino acids are designated A-G. The interfaces between helices of coiled coils are characterized by interactions of the residues located at the A position of one helix with the D position of a second helix. The interface of the two helices typically has hydrophobic residues at the A and D positions.

When the alpha helices interact to form a coiled coil, residues from one helix occupy the spaces between corresponding residues from the second helix, producing a "knobs in holes" packing.

Figure 5:
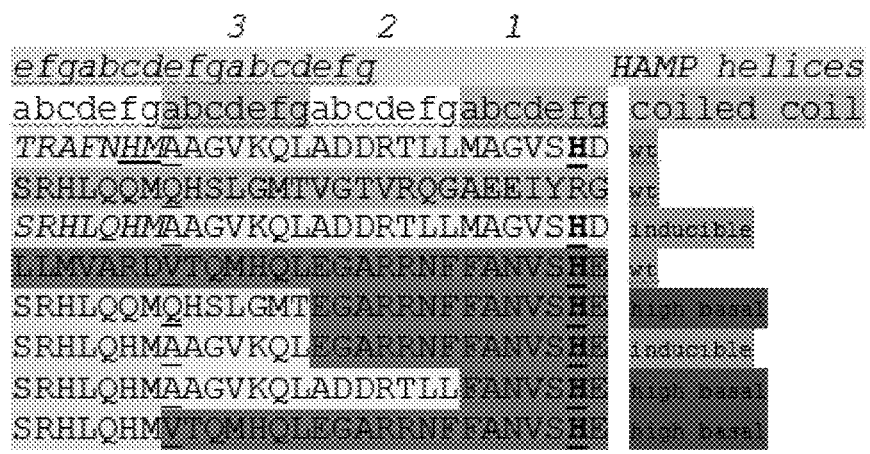
FIG. 5. Predicted coiled coil and fusions junctions from coiled coil test constructs. Proteins used in the fusions (EnvZ—SEQ ID NO:50; Trg—SEQ ID NO:51; Trz—SEQ ID NO:52; PhoR—SEQ ID NO:53) highlighted in blue. Sequence junctions from the 4 coiled coil test constructs (Trg"CC"Pho—SEQ ID NO:54; TrzEnvZCC—SEQ ID NO:55; TrzEnvZcc2&3—SEQ ID NO:56; TrgPhoRcc3—SEQ ID NO:57) are shown along with the signaling phenotype. The autophosphorylated Histidine from the DHP domain is shown in bold. The position of the HAMP helices, if found in the protein, are shown above the alignments.
Figure 6:
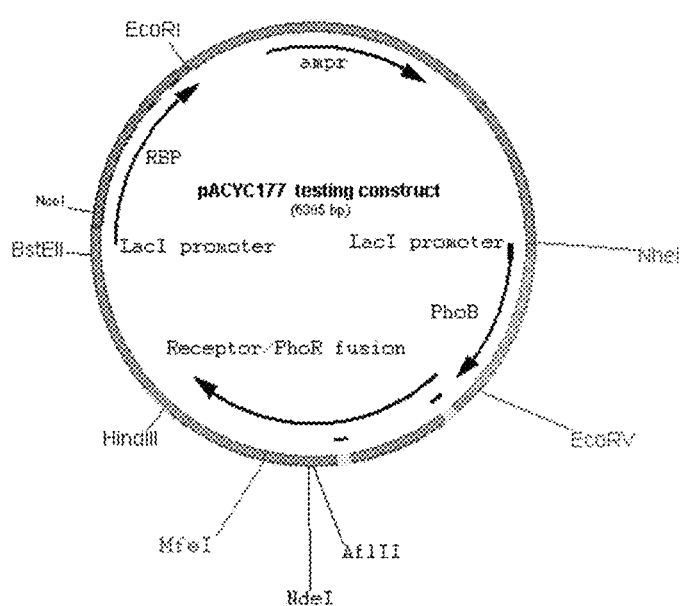
FIG. 6. pACYC177 based fusion testing plasmid.

The inventors reasoned that because this coiled-coil like element was a common motif in histidine kinases it would be possible to make fusions utilizing this element. In addition to strict fusions between Trg and PhoR, coiled coil elements were also incorporated from a functional fusion between Trg and EnvZ (Trz) with the idea that it may contain structural elements that allow proper HAMP signaling activation of an HK whereas PhoR, which lacks a HAMP domain, may not be able to be properly activated in the absence of these elements. The sequences of PhoR and Trz fusion were submitted to the HK coiled coil prediction program (groups.csail.mit.edu/cb/learncoil/cgi-bin/learncoil.cgi) (FIG. 4). Fusions incorporating the coiled-coil helices from Trz were designed as well as a fusion using the PhoR coiled-coil and the equivalent region of Trg which lacks the HK coiled coil (FIG. 5). These fusions were tested in *E. coli*. An expression plasmid was constructed in the plasmid pACYC177 with a LacI promoter driving RBP and a LacI promoter driving an operon consisting of the PhoB response regulator and the chimeric receptor:PhoR fusion to be tested. The operon was modeled after the naturally occurring PhoB/PhoR operon (FIG. 6). The expression constructs were transformed into the *E. coli* cell line BW23423, which has a PhoB responsive promoter driving a β-galactosidase reporter gene. The functionality of the fusions was tested by a split plate assay with X-Gal present to monitor β-galactosidase activity. One side of the split plate contained medium with maltose as a control; the other side of the split plate had medium containing ribose, the ligand being used to test functionality. A functional fusion should show no signaling on maltose (white colonies) whereas colonies growing on ribose should be blue. The blue color indicates the ligand activates the HK receptor fusion, which then transfers a phosphoryl group to PhoB leading to the activation of the β-galactosidase reporter gene. Three of the coiled coil based fusions showed high basal activity, but the fusion incorporating a coiled coil heptad of EnvZ (heptad repeat 3) was functional.

Figure 7:
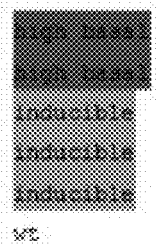
FIG. 7. Refining the TrzPhoR functional fusion point. Proteins used in the fusions are Trg (SEQ ID NO:51); EnvZ (SEQ ID NO:50); Trg"cc1"PhoR (SEQ ID NO:54); and PhoR (SEQ ID NO:53). TrzHAMP+VK (SEQ ID NO:60) recapitulates the original coiled coil based TrzPhoR fusion (SEQ ID NO:58). Residues efg of the Trg HAMP domain (QHS vs AAG in EnvZ) can functionally substitute for the EnvZ efg residues from the original TrzHAMP fusion as seen in TrgHAMP+V (SEQ ID NO:61) and TrzHAMP+V PhoR (SEQ ID NO:59).
Figure 9A:
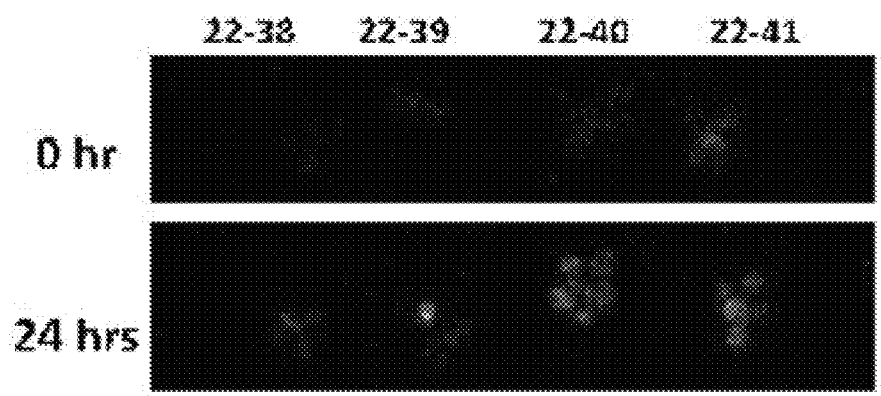

Functional analysis within the 7 amino acids of the EnvZ coiled-coil element revealed the key point of the fusion wasn't the first amino acid of the seven amino acids of the EnvZ coiled coil region (residue A) but the $4^{th}$ amino acid (residue D), a valine (FIG. 7). Because the ground state of a histidine kinase is such that the kinase is active, "kinase on" and the predominate signaling phenotype seen in non-functional fusions is "kinase on," the inventors reasoned that the valine at the D position is essential in maintaining the "kinase off" state in the absence of ligand dependent signaling. Fusions where the D position valine is replaced by alanine, glycine (the two hydrophobic amino acids smaller than valine) or a methionine (the D position residue of PhoR) results in constitutive activation (FIG. 8). *E. coli* has 10 HKs, including EnvZ, with HAMP domains adjacent to the HK coiled coil (FIG. 8). EnvZ is the only HK with a valine in the A/D position. There are 4 other amino acids, glutamate, isoleucine, leucine and threonine that occupy the A/D position in the 9 other *E. coli* HKs with a HAMP/HK coiled coil A/D overlap. Fusions testing whether any of these amino acids can functionally substitute for the valine were produced. All fusions resulted in the high basal phenotype or "kinase on" suggesting that the valine at the D position is essential in creating functional receptor/PhoR fusions. The A/D position represents the point at which the signal from the receptor acts to initiate histidine kinase activity. This position defines the N-terminal end of the signal dependent histidine kinase activation region. The functional TrzPhoR fusion represents an improvement in the synthetic signaling system that enables detector plants allowing for a cleaner signaling system. In addition, the TrzPhoR fusion has been introduced into the plant detector system and it was shown to be highly functional (FIG. 9).

Figure 10:
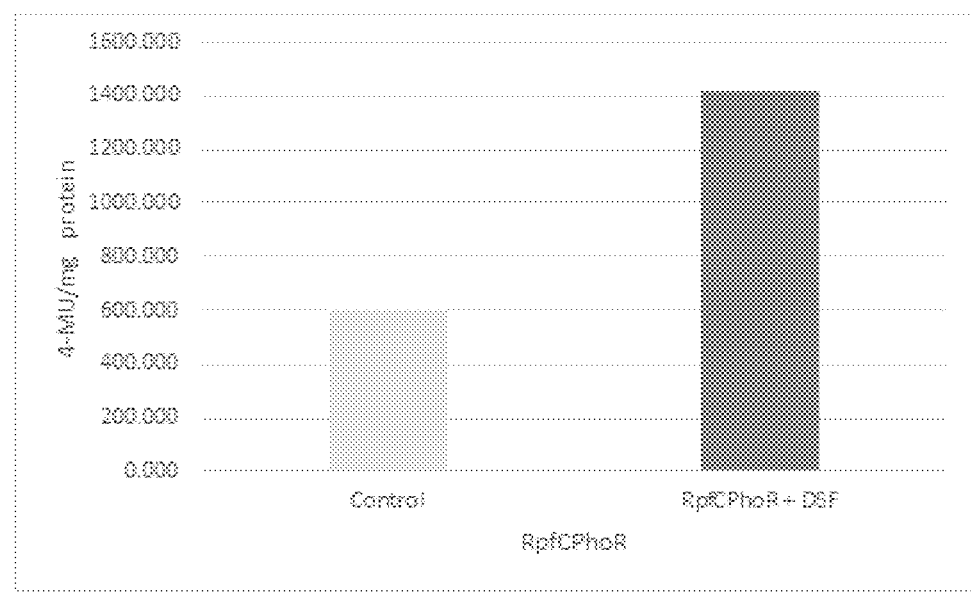
FIG. 10. β-galactosidase assay showing diffusible signaling factor signaling via the RpfCPhoR fusion. Yellow=control, Blue=DSF.
Figure 11A:
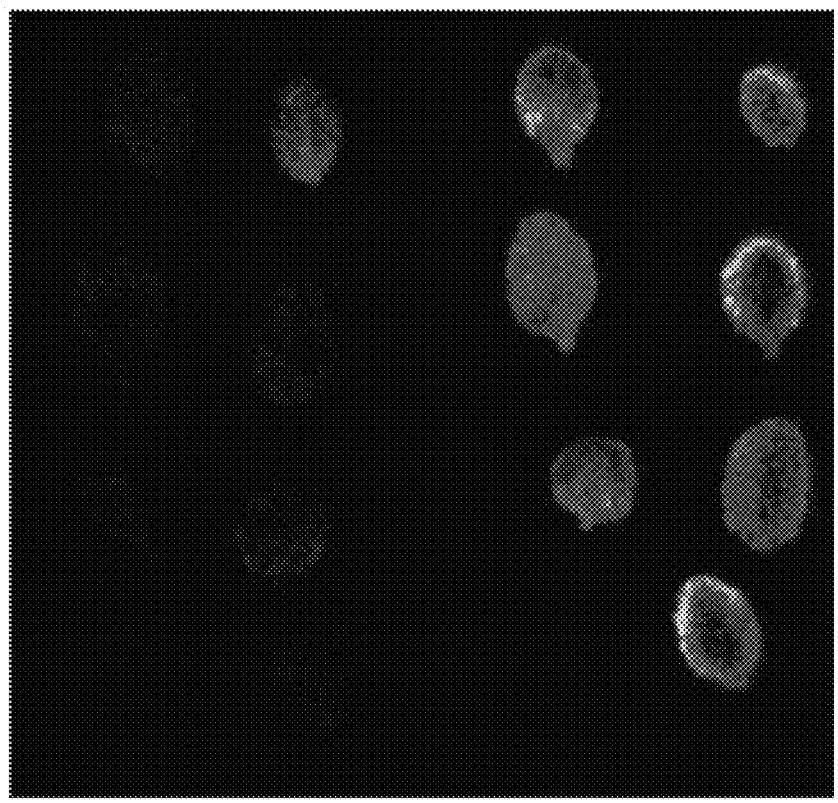
FIG. 11A and FIG. 11B.
Figure 11B:
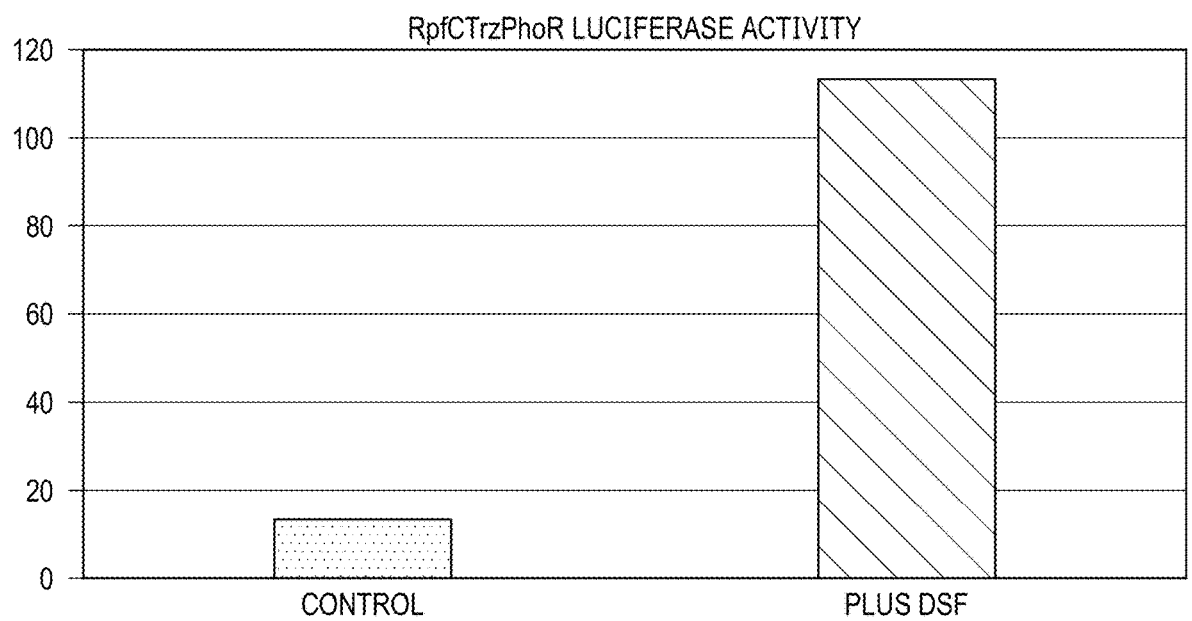
Figure 12A:
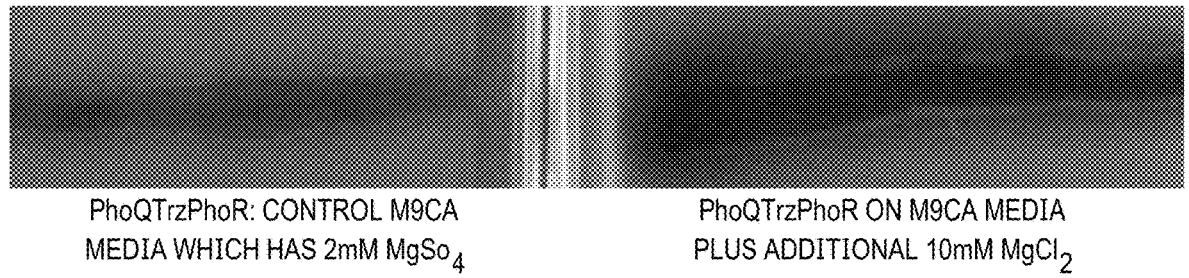
FIG. 12A and FIG. 12B.
Figure 12B:
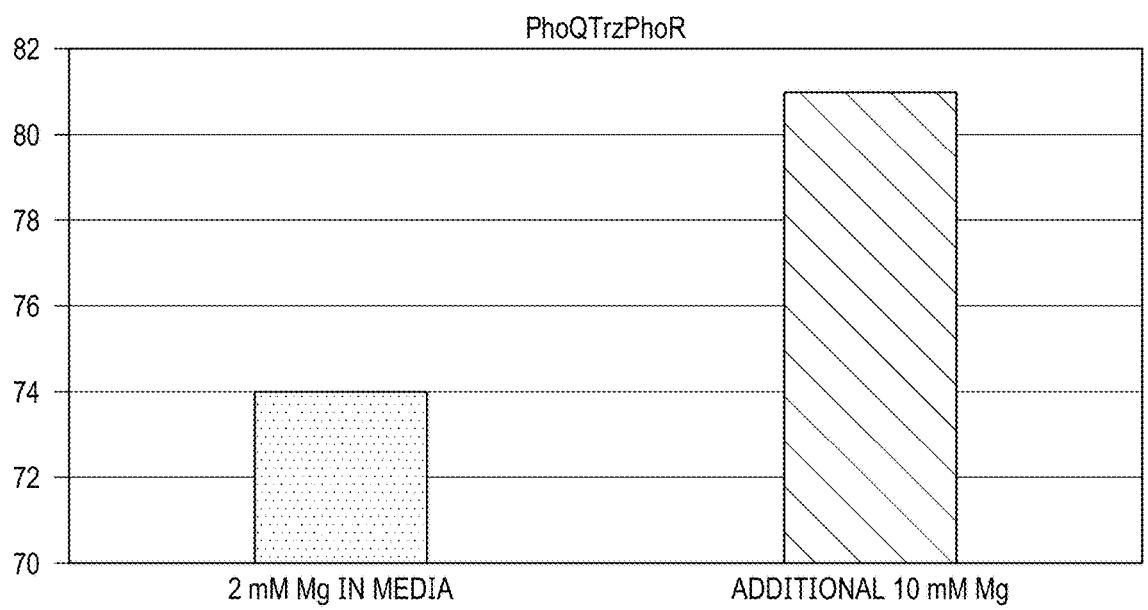

To test the utility of the A/D position as a fusion point for engineering novel receptor/histidine kinase fusions, a fusion between the RpfC receptor and PhoR was made. RpfC is a sensor HK involved in quorum sensing found in many species of *Xylella* and *Xanthomonas* that are bacterial pathogens of plants (Chatterjee, et al., *Proc. Natl. Acad. Sci. USA* 105:2670-2675, 2008). RpfC senses Diffusible Signaling Factor (DSF) mediating the control of virulence factor synthesis, and hence start the virulence response. RpfC does not have a HAMP domain only a cytoplasmic linker between the final transmembrane helix and the DHp domain. RpfC has a predicted HK coiled coil in the same register as the one predicted for PhoR. The RpfC DSF sensor and cytoplasmic linker was fused to PhoR at the A/D position. Both the D position of wild-type PhoR and the TrzPhoR fusion D position were used. The RpfCPhoR D position fusion containing a methionine at the D position had a high basal phenotype. The RpfCTrzPhoR D position fusion containing a valine at the D position showed inducible signaling in the presence of DSF extract (FIG. 10). This result showed the efficacy of using the A/D position as a fusion point for receptor/histidine kinase fusions. These results also showed how important the amino acid occupying the A/D position is in obtaining a functional fusion. In addition, when the RpfCTrzPhoR D position fusion was expressed in transgenic *Arabidopsis* plants, the presence of DSF was detected using a luciferase reporter gene readout (FIG. 11A and FIG. 11B). An additional test of the D position fusion point was implemented by fusing the PhoQ receptor to PhoR. PhoQ is a $Mg^{2+}$ responsive receptor histidine kinase that mediates adaptation to $Mg^{2+}$ limiting environments (Groisman, *J. Bacteriol.* 183:1835-1842, 2001). PhoQ also lacks a cytoplasmic HAMP domain. FIG. 12 demonstrates PhoQTrzPhoR showing an increase in $Mg^{2+}$ signaling (above that seen from the $Mg^{2+}$ already present in the media) with exposure to additional $Mg^{2+}$.

Figure 13A:
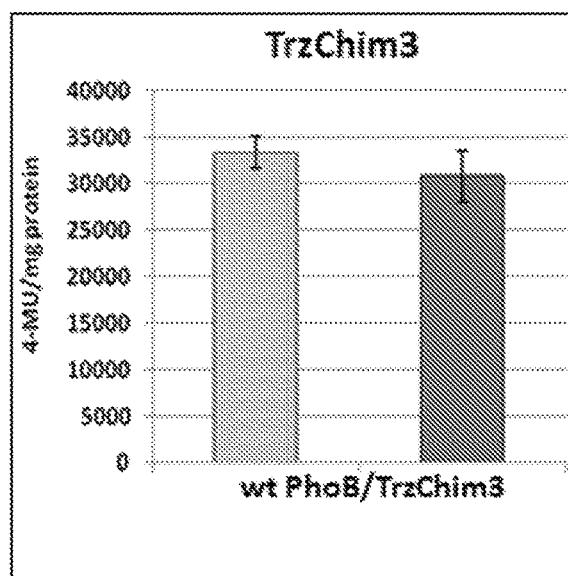
FIG. 13A and FIG. 13B. β-galactosidase activity of TrzChim3 and the TrzChim3 ADD→EGA mutant.
Figure 13B:
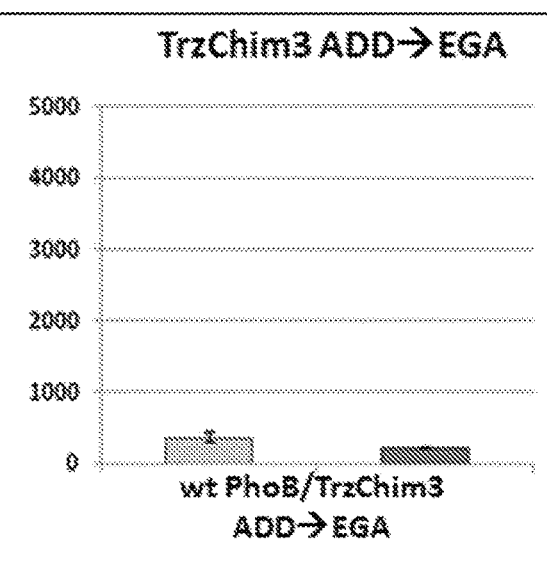

Example 2: Using the C-Terminal End of the Signal Dependent Histidine Kinase Activation Region to Engineer Inducible Kinase Activity in Non-Functional Receptor/Histidine Kinase Fusions An engineered an EnvZ variant that interacts with PhoB was previously engineered by substituting twenty-eight amino acids from the helix-loop-helix region of the PhoR DHp domain into the corresponding positions of the EnvZ DHp domain. This version of EnvZ, called Chim3, was able to phosphorylate PhoB in an in vitro assay (Skerker, et al., *Cell* 133:1043-1054, 2008). The changes in EnvZ that allowed it to interact with PhoB were incorporated into the Trg receptor EnvZ fusion Trz (Baumgartner, et al., *J. Bacteriol.* 176:1157-1163, 1994). This chimeric version of Trz was named TrzChim3. When TrzChim3 was tested in-vivo for the ability to signal through PhoB, high basal activity was found and no evidence of induction (FIG. 13A). This is termed as a kinase "locked-ON" phenotype. PhoR and EnvZ differ in three amino acids that are located directly upstream from a conserved arginine found in the DHp domain of both PhoR and EnvZ. The conserved arginine is in a region proposed to be involved in the interaction between the CA domain and the DHp domain in the kinase OFF/phosphatase ON state. The inventors reasoned that this area was important in activating histidine kinase activity and that this region of TrzChim3, which evolved to control EnvZ kinase activation, was unable to control the activity of the chimeric EnvZ/PhoR. In EnvZ the three amino acids are alanine, aspartate and aspartate (ADD) (residues 275-277, FIG. 14), while in PhoR the amino acids are glutamate, glycine and alanine (EGA) (see PhoR alignment with Trz, FIG. 14). A version of TrzChim3 was constructed with EGA substituting for ADD. This substitution allowed for the determination of whether the three residues have a function in controlling the CA/DHp interaction involved in the kinase off/phosphatase on state. Replacing the three putative CA interaction region EnvZ amino acids with those of PhoR did not restore ligand inducible function (FIG. 13B). However, the substitution did result in a change from a kinase "locked ON" phenotype to a kinase "locked OFF" phenotype, suggesting that this region could indeed be involved in the signal inducible activation of kinase activity.

Figure 15:
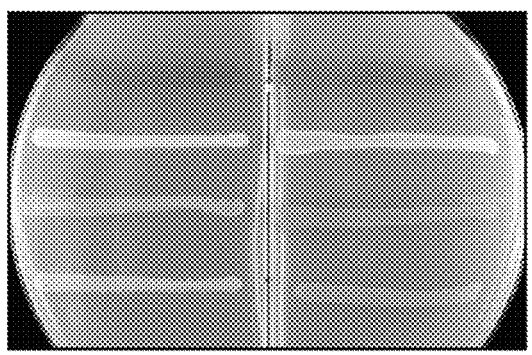
FIG. 15. Split plate assay showing ribose induction of the TrzChim variants 8 and 10. Left side=control, right side=ribose.
Figure 16:
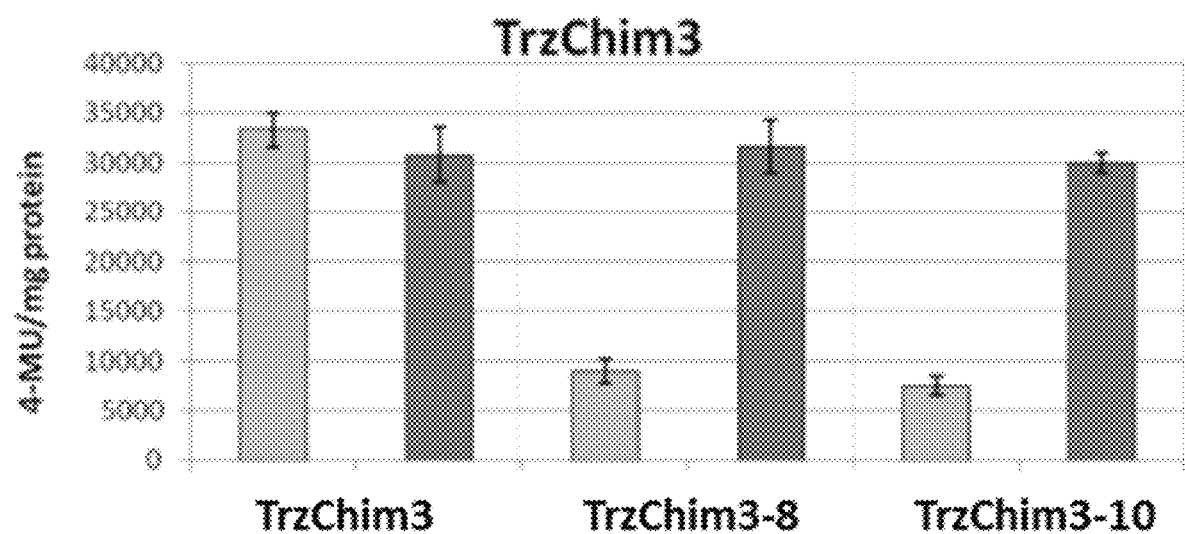
FIG. 16. β-galactosidase activity of TrzChim3, TrzChim3-8 and TrzChim3-10. Yellow=control, Blue=ribose.

The inventors reasoned that the chimeric nature of the DHp helix-loop-helix region in TrzChim3 results in a structure that does not correctly position the CA domain in the same way that the native EnvZ or PhoR CA domains are positioned. Further alterations to the putative CA interaction region were tested to determine if these could provide a functional HK. All three amino acid positions were randomly mutagenized and screened for functionality by plating on media with the ribose ligand and X-gal. Blue colonies were selected and re-tested for ribose inducibility on the split plates. Two mutants were isolated, TrzChim3-8 and TrzChim3-10, that showed ligand inducible signaling with the split plate assay (FIG. 15). The mutants were sequenced and it was found that the putative CA domain interaction region amino acids were mutated from EGA to RGV in TrzChim3-8 and EGA to AGG in TrzChim3-10. FIG. 16 shows quantification of the kinase function for TrzChim3, TrzChim3-8 and TrzChim3-10. The ability to restore in vivo inducibility to TrzChim3 suggests that the original TrzChim3 kinase "locked-ON" phenotype is due to a perturbation of the CA/DHp domain interaction. This experiment allowed for the identification and manipulation of the C-terminal end of the signal dependent histidine kinase activation region.

Example 3—Development of a Maltose Inducible Tar HK Fusion

In *E. coli*, the chemotactic receptor Tar mediates chemotaxis towards the amino acid aspartate and the disaccharide sugar maltose via an interaction between Tar and Maltose Binding Protein (MBP). When Tar is fused to the histidine kinase EnvZ to form Taz, the fusion retains the ability to be induced by aspartate, however it no longer shows a response to maltose. Trg was replaced with Tar in either the TrzPhoR fusion to form TazPhoR or in TrzChim3-8 to form Tac8. When TazPhoR or Tac8 was tested with maltose no maltose inducibility was observed. However, aspartate inducibility of both fusions was observed. In *E. coli*, aspartate mediates a stronger chemotactic response than maltose. The inventors reasoned that the transmembrane signal mediated by Tar when it binds aspartate is strong enough to activate histidine kinase activity in a Tar/HK fusion but the transmembrane signal mediated by Tar when it interacts with MBP is not strong enough to activate histidine kinase activity. Based on the ability to manipulate histidine kinase activity in TrzChim3, the inventors reasoned that targeting the same three amino acids in TazPhoR or Tac8 may results in variants whose kinase activation threshold is lowered enough to be activated by maltose. Amino acids 265, 266 and 267 in both Tac8 and TazPhoR were mutagenized by site directed mutagenesis. The site directed mutagenesis libraries were screened using fluorescent activated cell sorting (FACS). Initial sorting for Tac and TazPhoR functionality showed populations of cells with significant maltose ligand induction. From this screen two TazPhoR variants (TazPhoR 61 and 86; FIG. 17A) and one Tac8 variant (Tac40; FIG. 17B) were selected for further testing and development. This is the first reported example of MBP/maltose signaling via a TarHK fusion.

Figure 18:
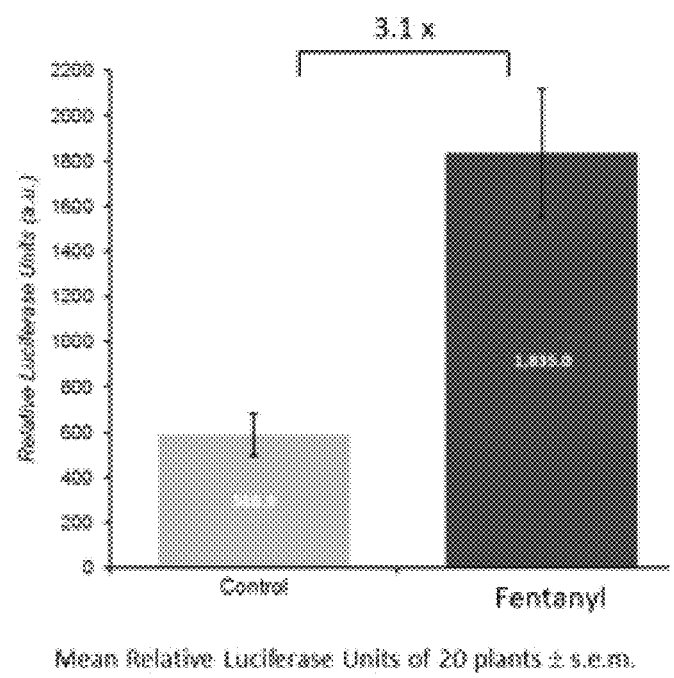
FIG. 18. Data showing function of computationally designed protein to fentanyl with histidine kinase fusions and synthetic signal transduction system. Pl
Figure 19:
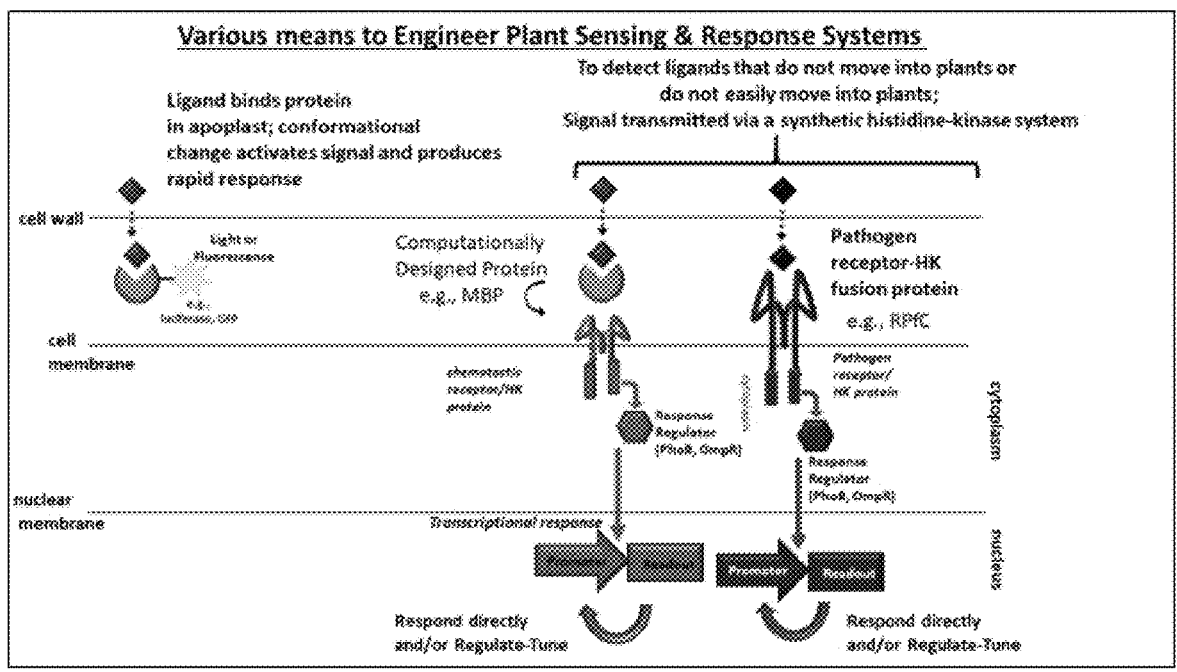
Figure 20:
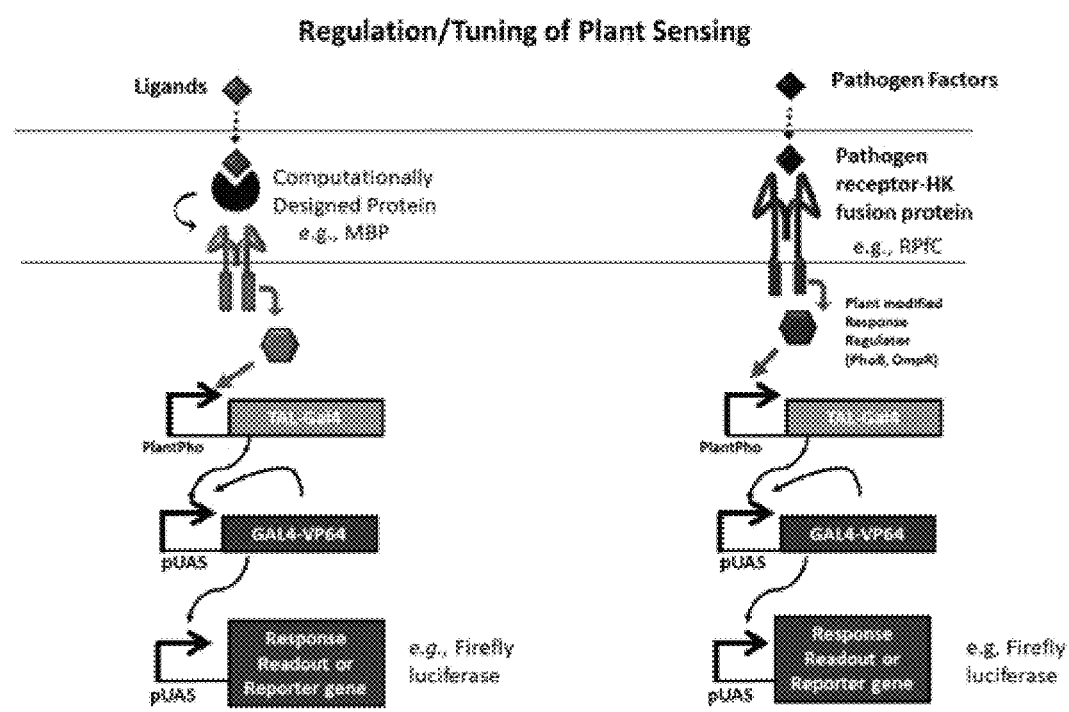

Example 4—Using TazPhoR61 and a Maltose Binding Protein with a Computationally Designed Binding Pocket to Detect a Fentanyl Ligand The ability to computationally design proteins partially or entirely, including the ligand binding pockets of several Periplasmic Binding Proteins, e.g., Maltose Binding Protein, Ribose Binding Protein, and Glucose Binding Protein, offers powerful means to produce new types of protein sensors and enable them in plants to serve as plant sentinels. Because previous TarHK fusions (Tar/EnvZ and Tar/PhoR) were unresponsive to maltose signaling through MBP it was not possible to test whether MBPs with computationally redesigned binding pockets could use HK signaling to report the presence of a ligand of interest. Using an MBP redesigned to bind a Fentanyl ligand, the inventors tested whether the maltose inducible TazPhoR61 could be used to detect the presence of Fentanyl in the environment. Two genetic circuits were used in this experiment. A Fentanyl Detection circuit consisting of the redesigned Maltose Binding Protein (MBP 6.1-5), TazPhoR61 and PhoB was co-transformed with a PhoB Signal Amplifying circuit consisting of a PhoB responsive promoter driving a Tal transcription factor engineered to bind Gal4 binding sites, a Gal4 responsive promoter driving a Gal4VP64 transcription factor (Gal4VP64 can bind its own promoter resulting in a positive feedback) and a Gal4 responsive promoter driving a luciferase reporter gene. Transformed plants were exposed to 500 µM Fentanyl and responded by inducing expression of luciferase (FIG. 18). The system described above is diagrammed in FIG. 19 with the quantitative controllers (positive feedback system) shown in FIG. 20.

The term "about" is used herein to indicate that a value includes the standard deviation of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or." When not used in conjunction closed wording in the claims or specifically noted otherwise, the words "a" and "an" denote "one or more."

The terms "comprise," "have," and "include" are open-ended linking verbs. Any forms or tenses of one or more of these verbs, such as "comprises," "comprising," "has," "having," "includes," and "including," are also open-ended. For example, any method that "comprises," "has" or "includes" one or more steps is not limited to possessing only those one or more steps and also covers other unlisted steps. Similarly, any cell that "comprises," "has" or "includes" one or more traits is not limited to possessing only those one or more traits and covers other unlisted traits.

While the disclosure has been described in connection with specific embodiments thereof, it will be understood that the present disclosure is capable of further modifications by one of skill in the art. It is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible. The present disclosure is therefore intended to encompass any variations, uses, or adaptations of the invention following, in general, the principles of the invention and including such departures from the present disclosure as come within known or customary practice within the art to which the invention pertains and as may be applied to the essential features herein before set forth.

All of the compositions and/or methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

All publications, patents, and patent publications cited are incorporated by reference herein in their entirety for all purposes.

What is claimed is:

1. A fusion protein comprising a receptor protein selected from the group consisting of a chemotactic receptor, a quorum sensing receptor, a histidine kinase receptor, and a computationally designed receptor, operably linked to a histidine kinase protein at the A/D fusion point wherein the A/D fusion point is a hydrophobic amino acid located at the overlapping interface between a coiled coil alpha helix of an extracellular receptor signal transmission domain of said receptor and an N-terminal coiled coil alpha helix of the internal dimerization and histidine phosphorylation (DHP) domain of said histidine kinase, wherein the fusion of said receptor and histidine kinase at the A/D fusion point results in inducible histidine kinase activity, and wherein said fusion protein further comprises a kinase activation region that has been engineered to activate said inducible histidine kinase activity through ligand binding.

2. The fusion protein of claim 1, wherein the chemotactic receptor protein is Trg, Tar, Tap or Tsr or a computationally redesigned receptor.

3. The fusion protein of claim 1, wherein the receptor involved in quorum sensing is the Xylella DSF receptor RpfC or the LuxPQ receptor LuxP or a computationally redesigned receptor.

4. The fusion protein of claim 1, wherein the histidine kinase protein is PhoR or EnvZ.

5. The fusion protein of claim 1, wherein the histidine kinase protein is a EnvZ/PhoR chimera.

6. The fusion protein of claim 1, wherein the histidine kinase protein is activated when the chemotactic receptor protein or the receptor involved in quorum sensing binds to a sensor protein, or a computationally designed receptor bound to a target substance.

7. The fusion protein of claim 6, wherein the target substance is a chemical agent, a heavy metal, a poison, a pollutant, a toxin, an herbicide, a polycyclic aromatic hydrocarbon, a benzene, a toluene, a xylene, a halogenated hydrocarbon, a steroid or other hormone, an explosive, or a degradation product of one of the foregoing compounds.

8. The fusion protein of claim 1, further comprising a plasma membrane targeting signal sequence operably linked to an N-terminus of the chemotactic receptor protein or receptor involved in quorum sensing, or a computationally designed receptor.

9. The fusion protein of claim 1, wherein the kinase activation region comprises a maltose binding protein and maltose is the ligand which activates the inducible histidine kinase activity.

10. A DNA construct comprising a nucleic acid segment that encodes the fusion protein of claim 1.

11. The DNA construct of claim 10, wherein the nucleic acid segment is operably linked to a promoter.

* * * * *